US011739386B2

(12) United States Patent
Lai-Goldman et al.

(10) Patent No.: US 11,739,386 B2
(45) Date of Patent: Aug. 29, 2023

(54) METHODS FOR DETERMINING RESPONSE TO PARP INHIBITORS

(71) Applicants: GeneCentric Therapeutics, Inc., Research Triangle Park, NC (US); The University of North Carolina at Chapel Hill, Chapel Hill, NC (US)

(72) Inventors: Myla Lai-Goldman, Durham, NC (US); Hawazin Faruki, Durham, NC (US); Greg Mayhew, Durham, NC (US); Charles Perou, Carrboro, NC (US); David Neil Hayes, Chapel Hill, NC (US)

(73) Assignees: GeneCentric Therapeutics, Inc., Durham, NC (US); The University of North Carolina at Chapel Hill, Chapel Hill, NC (US)

( * ) Notice: Subject to any disclaimer, the term of this patent is extended or adjusted under 35 U.S.C. 154(b) by 285 days.

(21) Appl. No.: 16/632,006

(22) PCT Filed: Jul. 20, 2018

(86) PCT No.: PCT/US2018/043086
§ 371 (c)(1),
(2) Date: Jan. 17, 2020

(87) PCT Pub. No.: WO2019/018764
PCT Pub. Date: Jan. 24, 2019

(65) Prior Publication Data
US 2020/0232042 A1 Jul. 23, 2020

Related U.S. Application Data

(60) Provisional application No. 62/578,065, filed on Oct. 27, 2017, provisional application No. 62/535,617, filed on Jul. 21, 2017.

(51) Int. Cl.
*C12Q 1/6886* (2018.01)
*C12N 9/10* (2006.01)

(52) U.S. Cl.
CPC ......... *C12Q 1/6886* (2013.01); *C12N 9/1077* (2013.01); *C12Q 2600/106* (2013.01); *C12Q 2600/158* (2013.01); *C12Y 204/0203* (2013.01); *G01N 2800/52* (2013.01)

(58) Field of Classification Search
None
See application file for complete search history.

(56) References Cited

U.S. PATENT DOCUMENTS

| | | |
|---|---|---|
| 4,683,202 A | 7/1987 | Mullis |
| 4,843,155 A | 6/1989 | Chomczynski |
| 5,384,261 A | 1/1995 | Winkler et al. |
| 5,445,934 A | 8/1995 | Fodor et al. |
| 5,677,195 A | 10/1997 | Winkler et al. |
| 5,708,153 A | 1/1998 | Dower et al. |
| 5,744,305 A | 4/1998 | Fodor et al. |
| 5,770,358 A | 6/1998 | Dower et al. |
| 5,770,722 A | 6/1998 | Lockhart et al. |
| 5,789,162 A | 8/1998 | Dower et al. |
| 5,800,992 A | 9/1998 | Fodor et al. |
| 5,854,033 A | 12/1998 | Lizardi |
| 5,856,174 A | 1/1999 | Lipshutz et al. |
| 5,874,219 A | 2/1999 | Rava et al. |
| 5,922,591 A | 7/1999 | Anderson et al. |
| 6,020,135 A | 2/2000 | Levine et al. |
| 6,033,860 A | 3/2000 | Lockhart et al. |
| 6,040,138 A | 3/2000 | Lockhart et al. |
| 6,040,193 A | 3/2000 | Winkler et al. |
| 7,473,767 B2 | 1/2009 | Dimitrov |
| 8,492,094 B2 | 7/2013 | Dimitrov et al. |
| 10,793,914 B2 * | 10/2020 | Skog .................... C12Q 1/6886 |
| 2009/0275608 A1 | 11/2009 | Ossovskaya et al. |

FOREIGN PATENT DOCUMENTS

WO   WO 2015/164586 A1   10/2015

OTHER PUBLICATIONS

Cobb et al (Crit Care Med 2002 vol. 30 p. 2711) (Year: 2002).*
Enard et al. (Science 2002 vol. 296 p. 340) (Year: 2002).*
International Search Report issued by the International Searching Authority for Application No. PCT/US18/43086, dated Dec. 14, 2018, 15 pages.
Barany, "Cloning, overexpression and nucleotide sequence of a thermostable DNA ligase-encoding gene," Proc. Natl. Acad. Sci. USA 88:189-193 (1991).
Bibikova et al., "Quantitative gene expression profiling in formalin-fixed, paraffin-embedded tissues using universal bead arrays," Am J. Pathol 165:1799-1807 (2004).
Brenner et al., "Gene expression analysis by massively parallel signature sequencing (MPSS) on microbead arrays," Nat. Biotech. 18:630-34, 2000.
Broomhead DS, Jones R, King GP., "Comment on Singular-value decomposition and embedding dimension," Phys Rev A Gen Phys. Jun. 2015;37(12):5004-5005 (1988).

(Continued)

*Primary Examiner* — Katherine D Salmon
(74) *Attorney, Agent, or Firm* — Cooley LLP

(57) ABSTRACT

Methods and compositions are provided for determining whether an adenocarcinoma or squamous cell carcinoma patient is likely to respond to PARP inhibitor treatment. Specifically, a method of assessing whether a patient's adenocarcinoma (AD) lung cancer subtype is terminal respiratory unit (TRU), proximal inflammatory (PI), or proximal proliferative (PP) or a patient's squamous cell carcinoma (SQ) is primitive, classical, secretory or basal is provided herein. The method entails detecting the levels of classifier biomarkers at the nucleic acid level, in an AD or SQ lung cancer sample obtained from the patient. Based in part on the levels of the classifier biomarkers, the AD lung cancer sample is classified as a TRU, PI, or PP AD sample or the SQ lung cancer sample is classified as primitive, classical, secretory or basal and a determination of whether the patient is likely to respond to PARP inhibitor treatment can be made.

9 Claims, 14 Drawing Sheets

(56) References Cited

OTHER PUBLICATIONS

Bryant et al. (2005) Specific killing of BRCA2-deficient tumours with inhibitors of poly(ADP-ribose) polymerase. Nature 434:913-917.
Cancer Genome Atlas Research Network. "Comprehensive genomic characterization of squamous cell lung cancers." Nature 489.7417 (2012): 519-525.
Clark et al., "Suppression of nonspecific binding of avidin-biotin complex (ABC) to proteins electroblotted to nitrocellulose paper," J Histochem Cytochem 34:1509-1512 (1986).
Collisson E.et al., "Comprehensive Molecular Profiling of Lung Adenocarcinoma," Nature 511(7511):543-550 (2014).
Cronin et al., "Measurement of gene expression in archival paraffin-embedded tissues: development and performance of a 92-gene reverse transcriptase-polymerase chain reaction assay," Am. J Pathol. 164(1):35-42 (2004).
Dabney, "Classification of microarrays to nearest centroids," Bioinformatics 21(22):4148-4154 (2005).
Daemen et al., "Cross-platform pathway-based analysis identifies markers of response to the PARP inhibitor olaparib.," Breast Cancer Res Treat 135(2):505-517 (2012).
Fan et al., "A Versatile Assay for High-Throughput Gene Expression Profiling on Universal Array Matrices," Genome Res. 14:878-885 (2004).
Fishel and Kaufman et al., "Meta-analysis of gene expression data: a predictor-based approach," Bioinformatics 23(13): 1599-606 (2007).
Fong et al., "Poly(ADP}-Ribose Polymerase Inhibition: Frequent Durable Responses in BRCA Carrier Ovarian Cancer Correlating With Platinum-Free Interval," Journal of Clinical Oncology 28(15):2512-2519 (2010).
Fox et al., "Formaldehyde Fixation," J Histochem Cytochem 33:845-853 (1985).
Friedman et al., "Regularization Paths for Generalized Linear Models via Coordinate Descent,"Journal of statistical software 33(1): 1-22 (2010).
Geiss et al., "Direct multiplexed measurement of gene expression with color-coded probe pairs," Nat. Biotechnol. 26:317-325 (2008).
Guatelli et al., "Isothermal, in vitro amplification of nucleic acids by a multienzyme reaction modeled after retroviral replication," Proc Natl Acad Sci USA. 87(5):1874-1878 (1990).
Irizarry et al., "Exploration, normalization, and summaries of high density oligonucleotide array probe level data," Biostatistics April 4(2): 249-64 (2003).
Konstantinopoulos et al., "Gene expression profile of BRCAness that correlates with responsiveness to chemotherapy and with outcome in patients with epithelial ovarian cancer," JClin Oncol 28(22):3555-3561 (2010).
Kwoh et al., "Transcription-based amplification system and detection of amplified human immunodeficiency virus type 1 with a bead-based sandwich hybridization format (TI RNA polymerase/in vitro nucleic acid amplification)," Proc. Natl. Acad. Sci. USA, 86:1173-1177 (1989).
Landegren et al., "A ligase-mediated gene detection technique," Science, 241(4869):1077-1080 (1988).
Lee ESet al., "Prediction of recurrence-free survival in postoperative non-small cell lung cancer patients by using an integrated model of clinical information and gene expression." Clinical Cancer Research 14(22):7397-7404 (2008).
Lim et al., VEGFR3 Inhibition Chemosensitizes Ovarian Cancer Stemlike Cells through Down-Regulation ofBRCA1 and BRCA2. Neoplasia 16(4):343-353 (2014).
McGhee and von Hippel, "Formaldehyde as a probe of DNA structure. II. Reaction with endocyclic imino groups of DNA bases," Biochemistry 14:1281-1296 (1975).
McGrail et al., "Improved prediction of PARP inhibitor response and identification of synergizing agents through use of a novel gene expression signature generation algorithm," Systems Biology and Applications. 3(8):1-12 (2017).
Meyer D., "Support vector machines: the interface to libsvm in package el071," 2014, 8 pages (dated Jul. 23, 2018).
Mullins et al., "Agreement in breast cancer classification between microarray and quantitative reverse transcription PCR from fresh-frozen and formalin-fixed, paraffin-embedded tissues," Clin Chem. 53(7):1273-1279 (2007).
Nielsen, "A comparison of PAM50 intrinsic subtyping with immunohistochemistry and clinical prognostic factors in tamoxifen-treated estrogen receptor-positive breast cancer," Clin Cancer Res. Nov. 1, 2010;16(21):5222-32 (2010).
Niki et al., "Expression of Vascular Endothelial Growth Factors A, B, C, and D and Their Relationships to Lymph Node Status in Lung Adenocarcinoma," Clinical Cancer Research 6(6):2431-2439 (2000).
Parzen, "On Estimation of a Probability Density Function and Mode," Stanford University, 1065-1076 (1962).
Patel et al. "Nonhomologous end joining drives poly(ADP-ribose) polymerase (PARP) inhibitor lethality in homologous recombination-deficient cells" PNAS 108 (8) 3406-3411 (2011).
Prat et al., Genomic Analyses across Six Cancer Types Identify Basal-like Breast Cancer as a Unique Molecular Entity. Scientific Reports. 3(3544): 1-12 (2013).
Quinlan, "Induction of Decision Trees," Machine Learning 1(1):81-106 (1986).
Raponi et al. "Gene expression signatures for predicting prognosis of squamous cell and adenocarcinomas of the lung," Cancer Res 66(7): 466-472 (2006).
Robin etai., "pROC: an open source package for R and S+ to analyze and compare ROC curves," BMC bioinformatic 12:77 (2011), 8 pages.
Rouskin et al., "Genome-wide probing of RNA structure reveals active unfolding of mRNA structures in vivo," Nature 505, pp. 701-705 (2014).
Rupp G and Locker J., University of Pittsburgh School of Medicine, "Purification and analysis of RNA from paraffin embedded tissues," BioTechniques 6(1):56-60 (1988).
Shedden et al., "Gene expression-based survival prediction in lung adenocarcinoma: a multi-site, blinded validation study: director's challenge consortium for the molecular classification of lung adenocarcinoma," Nat Med 14(8): 822-827 (2008).
Smyth Limma: linear models for microarray data. In: Bioinformatics and Computational Biology Solutions using Rand Bioconductor, R. Gentleman, V. Carey, S. Dudoit, R.Irizarry, W. Huber (eds.), Springer, New York, pp. 397-420 (2005).
Smyth, "Linear Models and Empirical Bayes Methods for Assessing Differential Expression in Microarray Experiments," Stat. Appi. Genet. Mol. Biol. 3: Article 3 (2004), 28 pages.
Sourisseau et al., "Aurora-A expressing tumour cells are deficient for homology-directed DNA double strand-break repair and sensitive to PARP inhibition," EMBO Mol Med 2:130-142 (2010).
Suykens JAK, Vandewalle J., "Least Squares Support Vector Machine Classifiers," Neural Processing Letters 9(3): 293-300 (1999).
Szumilas, "Explaining odds ratios," J. Can. Acad. Child Adolesc. Psychiatry 19(3): 227-229 (2010).
The Cancer Genome Atlas Research Network) Comprehensive molecular profiling of lung adenocarcinoma. Nature 511:543-550 and p. 546 (2014).
Tibshirani et al., "Diagnosis of multiple cancer types by shrunken centroids of gene expression," Proc. Natl. Acad. Sci. USA 99(10):6576-6572 (2002).
Tomida et al., "Relapse-related molecular signature in lung adenocarcinomas identifies patients with dismal prognosis," J Clin Oncol 27(17): 2793-2799 (2009).
Trapnell et al., "Transcript assembly and quantification by RNA-Seq reveals unannotated transcripts and isoform switching during cell differentiation," Nature biotechnology 28(5):511-515 (2010).
Trapnell et al., "TopHat: discovering splice junctions with RNA-Seq.," Bioinformatics 25(9):1105-11 (2009).
Velculescu et al., "Characterization of the yeast transcriptome," Cell 88(2):243-251 (1997).
Velculescu et al., "Serial analysis of gene expression," Science 270(5235):484-487 (1995).
Wilkerson et al., Lung Squamous Cell Carcinoma mRNA Expression Subtypes are Reproducible, Clinically Important and Correspond to Different Normal Cell Types. Clinical Clin Cancer Res 16(19):4864-4875 (2010).

(56) References Cited

OTHER PUBLICATIONS

Wilkerson et al., "Differential pathogenesis of lung adenocarcinoma subtypes involving sequence mutations, copy number, chromosomal instability, and methylation," PLoS One. 2012; 7(5) e36530. Doi:10.1371/journal.pone.0036530, 13 pages.

Wold, H. "Estimation of Principal Components and Related Models by Iterative Least Squares," in Multivariate Analysis, ed. P. R. Krishnaiah, New York:Academic Press, 391-420 (1966).

Wu and Wallace, "The ligation amplification reaction (LAR)—amplification of specific DNA sequences using sequential rounds of template dependent ligation.," Genomics, 4(4):560-569 (1989).

\* cited by examiner

METHODS FOR DETERMINING RESPONSE TO PARP INHIBITORS

CROSS-REFERENCE TO RELATED APPLICATIONS

This application is a U.S. national stage application of International Application No. PCT/US2018/043086, filed Jul. 20, 2018, which claims the benefit of priority to U.S. Provisional Application No. 62/535,617 filed Jul. 21, 2017, and U.S. Provisional Application No. 62/578,065 filed Oct. 27, 2017, each of which is incorporated by reference herein in its entirety for all purposes.

BACKGROUND OF THE INVENTION

Lung cancer is the leading cause of cancer death in the United States and over 220,000 new lung cancer cases are identified each year. Lung cancer is a heterogeneous disease with subtypes generally determined by histology (small cell, non-small cell, carcinoid, adenocarcinoma, and squamous cell carcinoma). Differentiation among various morphologic subtypes of lung cancer is essential in guiding patient management and additional molecular testing is used to identify specific therapeutic target markers. Variability in morphology, limited tissue samples, and the need for assessment of a growing list of therapeutically targeted markers pose challenges to the current diagnostic standard. Studies of histologic diagnosis reproducibility have shown limited intra-pathologist agreement and inter-pathologist agreement.

Accordingly, new methods are needed to further define populations that might be likely to respond to PARP inhibitors. The present invention addresses this and other needs.

SUMMARY OF THE INVENTION

In one aspect, provided herein is a method of determining whether an adenocarcinoma or squamous cell carcinoma patient is likely to respond to PARP inhibitor treatment, the method comprising, determining the adenocarcinoma subtype or the squamous cell carcinoma subtype of a lung tissue sample from the patient, wherein the adenocarcinoma subtype is selected from the group consisting of squamoid (proximal inflammatory), bronchoid (terminal respiratory unit) and magnoid (proximal proliferative), and the squamous cell carcinoma subtype is selected from the group consisting of primitive, classical, secretory and basal; and based on the subtype, assessing whether the patient is likely to respond to PARP inhibitor treatment. In some cases, the patient is initially determined to have adenocarcinoma or squamous cell carcinoma via a histological analysis of a sample. In some cases, the patient's adenocarcinoma molecular subtype is selected from squamoid (proximal inflammatory), bronchoid (terminal respiratory unit) or magnoid (proximal proliferative), and is determined via a histological analysis of a sample obtained from the patient. In some cases, the patient's squamous cell carcinoma subtype is selected from primitive, classical, secretory or basal, and is determined via a histological analysis of a sample obtained from the patient. In some cases, the sample is a formalin-fixed, paraffin-embedded (FFPE) lung tissue sample, fresh or a frozen tissue sample, an exosome, or a bodily fluid obtained from the patient. In some cases, the bodily fluid is blood or fractions thereof, urine, saliva, or sputum. In some cases, the determining the adenocarcinoma subtype or the squamous cell carcinoma subtype comprises determining expression levels of a plurality of classifier biomarkers. In some cases, the determining the expression levels of the plurality of classifier biomarkers is at a nucleic acid level by performing RNA sequencing, reverse transcriptase polymerase chain reaction (RT-PCR) or hybridization based analyses. In some cases, the plurality of classifier biomarkers for determining the adenocarcinoma subtype is selected from a publically available lung adenocarcinoma dataset. In some cases, the publically available lung adenocarcinoma dataset is TCGA Lung AD RNAseq dataset. In some cases, the plurality of classifier biomarkers for determining the squamous cell carcinoma subtype is selected from a publically available lung squamous cell carcinoma dataset. In some cases, the publically available lung squamous cell carcinoma dataset is TCGA Lung SQ RNAseq dataset. In some cases, the plurality of classifier biomarkers for determining the adenocarcinoma subtype is selected from Table 1. In some cases, the RT-PCR is quantitative real time reverse transcriptase polymerase chain reaction (qRT-PCR). In some cases, the RT-PCR is performed with primers specific to the plurality of classifier biomarkers of Table 1; comparing the detected levels of expression of the plurality of classifier biomarkers of Table 1 to the expression of the plurality of classifier biomarkers of Table 1 in at least one sample training set(s), wherein the at least one sample training set comprises expression data of the plurality of classifier biomarkers of Table 1 from a reference adenocarcinoma TRU sample, expression data of the plurality of classifier biomarkers of Table 1 from a reference adenocarcinoma PP sample, expression data of the plurality of classifier biomarkers of Table 1 from a reference adenocarcinoma PI sample, or a combination thereof; and classifying the first sample as TRU, PP, or PI based on the results of the comparing step. In some cases, the comparing step comprises applying a statistical algorithm which comprises determining a correlation between the expression data obtained from the sample and the expression data from the at least one training set(s); and classifying the sample as a TRU, PP, or PI subtype based on the results of the statistical algorithm. In some cases, the plurality of the classifier biomarkers comprise each of the classifier biomarkers set forth in Table 1. In some cases, the plurality of classifier biomarkers for determining the squamous cell carcinoma subtype is selected from Table 3. In some cases, the RT-PCR is quantitative real time reverse transcriptase polymerase chain reaction (qRT-PCR). In some cases, the RT-PCR is performed with primers specific to the plurality of classifier biomarkers of Table 3; comparing the detected levels of expression of the plurality of classifier biomarkers of Table 3 to the expression of the plurality of classifier biomarkers of Table 3 in at least one sample training set(s), wherein the at least one sample training set comprises expression data of the plurality of classifier biomarkers of Table 3 from a reference squamous cell carcinoma basal sample, expression data of the plurality of classifier biomarkers of Table 3 from a reference squamous cell carcinoma classical sample, expression data of the plurality of classifier biomarkers of Table 3 from a reference squamous cell carcinoma primitive sample, expression data of the plurality of classifier biomarkers of Table 3 from a reference squamous cell carcinoma secretory sample or a combination thereof; and classifying the first sample as basal, classical, primitive or secretory based on the results of the comparing step. In some cases, the comparing step comprises applying a statistical algorithm which comprises determining a correlation between the expression data obtained from the sample and the expression data from the at least one training set(s); and classifying the sample as a basal, classical, primitive or secretory subtype based on the results of the statistical algorithm. In some cases, the plurality of the classifier biomarkers comprise each of the classifier biomarkers set forth in Table 3.

In another aspect, provided herein is a method for selecting an adenocarcinoma or squamous cell carcinoma patient for PARP inhibitor treatment, the method comprising, determining an adenocarcinoma subtype or squamous cell carcinoma subtype of a lung tissue sample from the patient, based on the subtype; and selecting the patient for PARP inhibitor treatment. In some cases, the patient is initially determined to have adenocarcinoma or squamous cell carcinoma via a histological analysis of a sample. In some cases, the patient's adenocarcinoma molecular subtype is selected from squamoid (proximal inflammatory), bronchoid (terminal respiratory unit) or magnoid (proximal proliferative), and is determined via a histological analysis of a sample obtained from the patient. In some cases, the patient's squamous cell carcinoma subtype is selected from primitive, classical, secretory or basal, and is determined via a histological analysis of a sample obtained from the patient. In some cases, the sample is a formalin-fixed, paraffin-embedded (FFPE) lung tissue sample, fresh or a frozen tissue sample, an exosome, or a bodily fluid obtained from the patient. In some cases, the bodily fluid is blood or fractions thereof, urine, saliva, or sputum. In some cases, the determining the adenocarcinoma subtype or the squamous cell carcinoma subtype comprises determining expression levels of a plurality of classifier biomarkers. In some cases, the determining the expression levels of the plurality of classifier biomarkers is at a nucleic acid level by performing RNA sequencing, reverse transcriptase polymerase chain reaction (RT-PCR) or hybridization based analyses. In some cases, the plurality of classifier biomarkers for determining the adenocarcinoma subtype is selected from a publically available lung adenocarcinoma dataset. In some cases, the publically available lung adenocarcinoma dataset is TCGA Lung AD RNAseq dataset. In some cases, the plurality of classifier biomarkers for determining the squamous cell carcinoma subtype is selected from a publically available lung squamous cell carcinoma dataset. In some cases, the publically available lung squamous cell carcinoma dataset is TCGA Lung SQ RNAseq dataset. In some cases, the plurality of classifier biomarkers for determining the adenocarcinoma subtype is selected from Table 1. In some cases, the RT-PCR is quantitative real time reverse transcriptase polymerase chain reaction (qRT-PCR). In some cases, the RT-PCR is performed with primers specific to the plurality of classifier biomarkers of Table 1; comparing the detected levels of expression of the plurality of classifier biomarkers of Table 1 to the expression of the plurality of classifier biomarkers of Table 1 in at least one sample training set(s), wherein the at least one sample training set comprises expression data of the plurality of classifier biomarkers of Table 1 from a reference adenocarcinoma TRU sample, expression data of the plurality of classifier biomarkers of Table 1 from a reference adenocarcinoma PP sample, expression data of the plurality of classifier biomarkers of Table 1 from a reference adenocarcinoma PI sample, or a combination thereof; and classifying the first sample as TRU, PP, or PI based on the results of the comparing step. In some cases, the comparing step comprises applying a statistical algorithm which comprises determining a correlation between the expression data obtained from the sample and the expression data from the at least one training set(s); and classifying the sample as a TRU, PP, or PI subtype based on the results of the statistical algorithm. In some cases, the plurality of the classifier biomarkers comprise each of the classifier biomarkers set forth in Table 1. In some cases, the plurality of classifier biomarkers for determining the squamous cell carcinoma subtype is selected from Table 3. In some cases, the RT-PCR is quantitative real time reverse transcriptase polymerase chain reaction (qRT-PCR). In some cases, the RT-PCR is performed with primers specific to the plurality of classifier biomarkers of Table 3; comparing the detected levels of expression of the plurality of classifier biomarkers of Table 3 to the expression of the plurality of classifier biomarkers of Table 3 in at least one sample training set(s), wherein the at least one sample training set comprises expression data of the plurality of classifier biomarkers of Table 3 from a reference squamous cell carcinoma basal sample, expression data of the plurality of classifier biomarkers of Table 3 from a reference squamous cell carcinoma classical sample, expression data of the plurality of classifier biomarkers of Table 3 from a reference squamous cell carcinoma primitive sample, expression data of the plurality of classifier biomarkers of Table 3 from a reference squamous cell carcinoma secretory sample or a combination thereof; and classifying the first sample as basal, classical, primitive or secretory based on the results of the comparing step. In some cases, the comparing step comprises applying a statistical algorithm which comprises determining a correlation between the expression data obtained from the sample and the expression data from the at least one training set(s); and classifying the sample as a basal, classical, primitive or secretory subtype based on the results of the statistical algorithm. In some cases, the plurality of the classifier biomarkers comprise each of the classifier biomarkers set forth in Table 3.

In yet another aspect, provided herein is a method of treating lung cancer in a subject, the method comprising: measuring the expression level of at least one biomarker nucleic acid in a lung cancer sample obtained from the subject, wherein the at least one biomarker nucleic acid is selected from a set of biomarkers listed in Table 1 or Table 3, wherein the presence, absence and/or level of the at least one biomarker indicates a subtype of the lung cancer; and administering a PARP inhibitor treatment based on the subtype of the lung cancer. In some cases, the lung cancer sample is an adenocarcinoma lung cancer sample, and wherein the set of biomarkers is Table 1. In some cases, the at least one biomarker nucleic acid selected from the set of biomarkers comprises, consists essentially of or consists of at least two biomarker nucleic acids, at least 8 biomarker nucleic acids, at least 16 biomarker nucleic acids, at least 32 biomarker nucleic acids, or all 48 biomarker nucleic acids of Table 1. In some cases, the lung tissue sample was previously diagnosed as being adenocarcinoma. In some cases, the lung cancer sample is a squamous cell carcinoma sample, and wherein the set of biomarkers is Table 3. In some cases, the at least one biomarker nucleic acid selected from the set of biomarkers comprises, consists essentially of or consists of at least two biomarker nucleic acids, at least 10 biomarker nucleic acids, at least 20 biomarker nucleic acids, at least 30 biomarker nucleic acids, at least 40 biomarker nucleic acids, at least 50 biomarker nucleic acids, at least 60 biomarker nucleic acids, at least 70 biomarker nucleic acids or all of the biomarker nucleic acids of Table 3. In some cases, the lung tissue sample was previously diagnosed as being squamous cell carcinoma. In some cases, the previous diagnosis was by histological examination. In some cases, the method further comprises measuring the expression of at least one biomarker from an additional set of biomarkers. In some cases, the additional set of biomarkers comprise one or more homologous recombination (HR) related genes. In some cases, the one or more HR-related genes are selected from ATM, ATR, BRCA1, BRCA2, BRIP1 (FANCJ), CDK12, CHEK1, CHEK2, FANCA, FANCI, FANCD2, MRE11A, RAD51L1 (RAD51B), RAD51C, PTEN or a combination thereof. In some cases, the measuring the expression level is conducted using an amplification, hybridization and/or sequencing assay. In some cases, the amplification, hybridization and/or sequencing assay comprises performing quantitative real time reverse transcriptase polymerase chain reaction (qRT-PCR), RNAseq, microarrays, gene chips, nCounter Gene Expression Assay, Serial Analysis of Gene Expression (SAGE), Rapid Analysis of Gene Expression (RAGE), nuclease protection assays, Northern blotting, or any other equivalent gene expression detection techniques. In some cases, the expression level is detected by performing qRT-PCR. In some cases, the sample is a formalin-fixed, paraffin-embedded (FFPE) lung tissue sample, fresh or a frozen tissue sample, an exosome, wash fluids, cell pellets, or a bodily fluid obtained from the patient. In some cases, the bodily fluid is blood or fractions thereof, urine, saliva, or sputum. In some cases, the patient's adenocarcinoma subtype is selected from squamoid (proximal inflammatory), bronchoid (terminal respiratory unit) or magnoid (proximal proliferative). In some cases, the patient's squamous cell carcinoma subtype is selected from primitive, classical, secretory or basal.

In a still further aspect, provided herein is a method for determining regulation of homologous recombination (HR) in an adenocarcinoma (AD) or squamous cell carcinoma (SQ) lung cancer patient comprising detecting the expression of one or a plurality of homologous recombination (HR) related genes in a sample obtained from the lung AD or SQ lung cancer patient. In some cases, the one or more HR-related genes are selected from ATM, ATR, BRCA1, BRCA2, BRIP1 (FANCJ), CDK12, CHEK1, CHEK2, FANCA, FANCI, FANCD2, MRE11A, RAD51L1 (RAD51B), RAD51C, PTEN or a combination thereof. In some cases, the method further comprises determining the lung AD or SQ subtype of the sample obtained from the patient. In some cases, the method further comprises determining an association between the expression of the one or plurality of HR-related genes to the lung AD or SQ subtype.

DETAILED DESCRIPTION OF THE INVENTION

Figure 1:
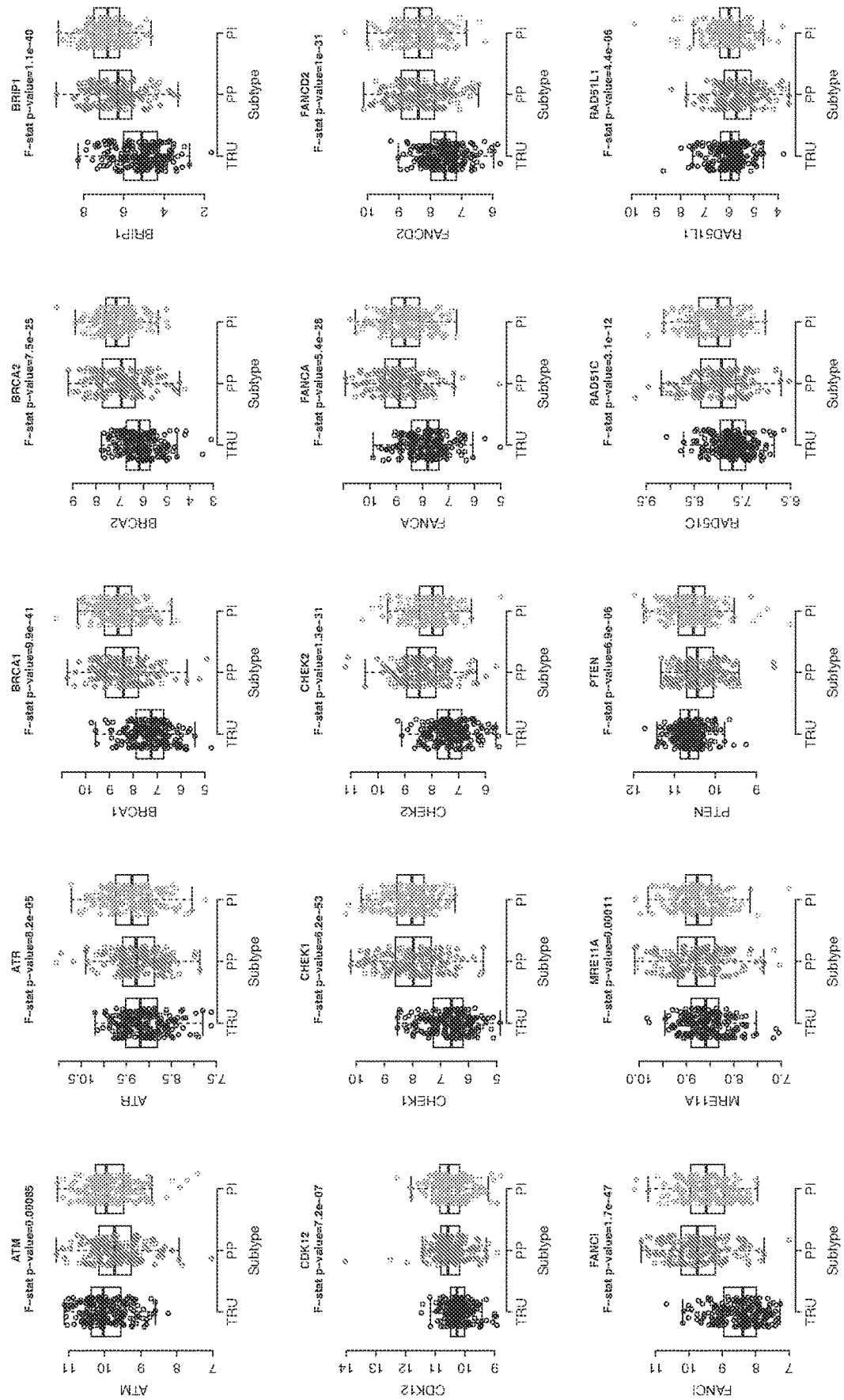
FIG. 1 illustrates marked differences in gene expression patterns of 15 recognized homologous recombination (HR) related genes for AD subtypes. AD subtyping was performed using the 506 gene gold standard sub-typer described in Example 1.

Gene expression based lung cancer subtyping has been shown to classify adenocarcinoma (AD) tumors into 3 biologically distinct subtypes (Terminal Respiratory Unit (TRU; formerly referred to as Bronchioid), Proximal Inflammatory (PI; formerly referred to as Squamoid), and Proximal Proliferative (PP; formerly referred to as Magnoid)) and squamous cell carcinoma (SQ) tumors into 4 biologically distinct subtypes (Primitive, Classical, Secretory, Basal). For AD, the three subtypes vary in their prognosis, in their distribution of smokers vs. nonsmokers, in their prevalence of EGFR alterations, ALK rearrangements, TP53 mutations, and in their angiogenic features, while the three subtypes of AD and 4 subtypes of SQ different in their level of immune activation, loss of RB1, KEAP/NFE2L2 oxidative stress alterations, and NF alterations. The present invention addresses the need in the field for determining the variable expression of underlying homologous recombination (HR) related genes in lung cancer subtypes (e.g., AD and SQ) and for determining patient populations likely to respond to therapeutics such as, for example, poly (ADP-ribose) polymerase (PARP) inhibitors based in part on the lung cancer subtype (e.g., Terminal Respiratory Unit (TRU), Proximal Inflammatory (PI), Proximal Proliferative (PP) or Primitive, Classical, Secretory, Basal) of the patient.

In one embodiment, provided herein is a method for determining regulation of homologous recombination (HR) in an adenocarcinoma (AD) or squamous cell carcinoma (SQ) lung cancer patient by determining or detecting the expression of one or a plurality of homologous recombination (HR) related genes in a sample obtained from the lung AD or SQ lung cancer patient. The determination or detection of the expression of the one or plurality of HR related genes can be performed using any of the methods known in the art and/or provided herein. In one embodiment, the method further comprises determining the lung AD or SQ subtype of a sample obtained from the patient. The sample used to determine the expression of the one or plurality of HR-related genes can be the same sample used to determine the lung AD or SQ subtype. The determination of the AD or SQ subtype of the sample obtained from the patient can be performed using any method for subtyping AD or SQ known in the art and/or provided herein. A change in expression of one or a plurality of HR related genes can be indicative of the state or level of activation or regulation of HR related pathways in a subject. The change in expression can be a change in the expression level or abundance of the one or plurality of HR related genes. In some cases, the lowering of the expression level or abundance of the one or plurality of HR related genes can affect the subsequent activity level or functioning of the one or plurality of HR related genes. In some cases, a reduction in or lowering of the expression of one or a plurality of HR related genes in a subject can indicate that one or more of said subject's HR related pathways has a reduced level of activity or function or is HR-deficient. In some embodiments, an association between the expression of said one or a plurality of HR-related genes to the lung AD or SQ subtype can be determined.

In another embodiment, provided herein is a method for determining whether an adenocarcinoma (AD) or squamous cell carcinoma (SQ) lung cancer patient is likely to respond to treatment with poly (ADP-ribose) polymerase (PARP) inhibitors by determining the subtype of AD or SQ of a sample obtained from the patient and, based on the AD or SQ lung cancer subtype, assessing whether the patient is likely to respond to PARP inhibitor treatment. The assessing of whether the patient is likely to respond to one or more PARP inhibitors can entail detecting the expression of one or more homologous recombination (HR) related genes in a lung AD or SQ subtype and determining an association between the expression of said one or more HR-related genes to the lung AD or SQ subtype. Further, another aspect of the methods provided herein can be that assessment of whether the patient is likely to respond to PARP inhibitor treatment based on the methods provided herein can also correlate with or be predictive of said patients response or sensitivity to one or more chemotherapeutic agents. The one or more chemotherapeutic agents can be any chemotherapeutic agents known in the art.

In yet another embodiment, provided herein is a method of selecting a patient suffering from AD or SQ for PARP inhibitor treatment by determining an AD or SQ subtype of a sample from the patient and, based on the AD or SQ subtype, selecting the patient for PARP inhibitor treatment. The AD or SQ can be lung cancer AD or SQ. Each lung cancer AD or SQ subtype may show a differential response to PARP inhibitor treatment. Further to this embodiment, the method can further comprise determining the variable expression of one or more underlying HR related genes in a lung cancer AD or SQ subtype and determining an association between the expression of said one or more underlying HR-related genes to the lung AD or SQ subtype.

Further to the methods provided herein, specific lung cancer AD subtypes can show levels of expression of one or a plurality of HR related genes that differ as compared to other lung cancer AD subtypes or a control. Specific lung cancer SQ subtypes can show levels of expression of one or a plurality of HR related genes that differ as compared to other lung cancer SQ subtypes or a control. In one embodiment, the TRU subtype of AD shows reduced expression of one or a plurality of HR related genes as compared to other lung cancer AD subtypes or a control. In a separate embodiment, the basal or secretory subtypes of SQ show reduced expression of one or a plurality of HR related genes as compared to other lung cancer SQ subtypes or a control. The control can be a sample from a healthy subject or a subject that is not suffering from lung cancer.

As discussed herein, a change in expression of one or a plurality of HR related genes can be indicative of the state or level of activation of HR related pathways in a subject. The change in expression can be a change in the expression level or abundance of the one or plurality of HR related genes. In some cases, the lowering of the expression level or abundance of the one or plurality of HR related genes can affect the subsequent activity level or functioning of the one or plurality of HR related genes. In some cases, a reduction in or lowering of the expression of one or a plurality of HR related genes in a subject can indicate that one or more of said subject's HR related pathways has a reduced level of activity or function or is HR-deficient. A subject with one or more deficient HR related pathways or with one or more HR related pathways with reduced activity or function may have an increased likelihood of responding favorably to treatment with a PARP inhibitor. The sensitivity of HR-deficient cells/tumors to PARP Inhibitors has been described in at least Patel et al. "Nonhomologous end joining drives poly (ADP-ribose) polymerase (PARP) inhibitor lethality in homologous recombination-deficient cells" PNAS Feb. 22, 2011. 108 (8) 3406-3411, Sourisseau T, et al. (2010) Aurora-A expressing tumour cells are deficient for homology-directed DNA double strand-break repair and sensitive to PARP inhibition. EMBO Mol Med 2:130-142 and Bryant H E, et al. (2005) Specific killing of BRCA2-deficient tumours with inhibitors of poly(ADP-ribose) polymerase. Nature 434:913-917, each of which is herein incorporated by reference. The PARP inhibitor can be any PARP inhibitor known in the art and/or provided herein. In some cases, a subject with a TRU subtype of AD may be a candidate for PARP inhibitor treatment. In some cases, a subject with a basal or secretory subtype of SQ may be a candidate for PARP inhibitor treatment.

The HR-related genes for any method provided herein can be ATM Serine/Threonine Kinase (ATM), ATR Serine/Threonine Kinase (ATR), BRCA1, DNA Repair Associated (BRCA1), BRCA2, DNA Repair Associated (BRCA2), BRCA1 Interacting Protein C-Terminal Helicase 1 (BRIP1 (FANCJ)), Cyclin Dependent Kinase 12 (CDK12), Checkpoint Kinase 1 (CHEK1), Checkpoint Kinase 2 (CHEK2), Fanconi Anemia Complementation Group A (FANCA), Fanconi Anemia Complementation Group I (FANCI), Fanconi Anemia Complementation Group D2 (FANCD2), MRE11 Homolog, Double Strand Break Repair Nuclease (MRE11A), RAD51 Paralog B (RAD51L1 (RAD51B)), RAD51 Paralog C (RAD51C), Phosphatase And Tensin Homolog (PTEN) or any combination thereof.

In any method provided herein, the association between an HR-related gene and lung AD or SQ subtype as determined using any method provided herein can be adjusted by using one or more BRCAness/PARP inhibitor response signatures and a proliferation score. The one or more BRCAness/PARP inhibitor response signatures can be any BRCAness/PARP inhibitor response signature known in the art such as, for example, the BRCAness/PARP inhibitor response signatures developed in ovarian and/or breast cancer (Konstantinopoulos et al. PMID 20547991, Daemen et al. PMID 22875744 and McGrail et al. PMID 28649435). The proliferation score can be a PAM50 proliferation score or pscore such as for example, the pscore disclosed in Nielsen et al. Clin Cancer Res. 2010 Nov. 1; 16(21): 5222-5232.

The determination of the AD or SQ subtype of the sample obtained from the patient in any method provided herein can be performed using any method for subtyping AD or SQ known in the art. In one embodiment, the sample obtained from the patient has been previously diagnosed as being AD, and the methods provided herein are used to determine the AD subtype of the sample. In one embodiment, the sample obtained from the patient has been previously diagnosed as being SQ, and the methods provided herein are used to determine the SQ subtype of the sample. The previous diagnosis can be based on a histological analysis. The histological analysis can be performed by one or more pathologists. In one embodiment, the AD or SQ subtyping is performed via gene expression analysis of a set or panel of biomarkers or subsets biomarkers or subsets thereof in order to generate an expression profile. The gene expression analysis can be performed on a lung cancer sample (e.g., lung cancer AD sample or lung cancer SQ sample) obtained from a patient in order to determine the presence, absence or level of expression of one or more biomarkers selected from a publically available lung cancer database described herein and/or Table 1 or 3 provided herein. The AD subtype is selected from the group consisting of squamoid (proximal inflammatory), bronchoid (terminal respiratory unit) and magnoid (proximal proliferative), while the SQ subtype is selected from the group consisting of primitive, classical, secretory and basal.

The PARP inhibitor for use in any method provided herein can be any PARP inhibitor known in the art. The PARP inhibitor can be selected from olaparib, rucaparib, niraparib, iniparib, talazoparib, veliparib, CEP 9722, Eisai's E7016, BGB-290 or 3-aminobenzamide.

As used herein, an "expression profile" comprises one or more values corresponding to a measurement of the relative abundance, level, presence, or absence of expression of a discriminative gene. An expression profile can be derived from a subject prior to or subsequent to a diagnosis of lung cancer, can be derived from a biological sample collected from a subject at one or more time points prior to or following treatment or therapy, can be derived from a biological sample collected from a subject at one or more time points during which there is no treatment or therapy (e.g., to monitor progression of disease or to assess development of disease in a subject diagnosed with or at risk for lung cancer), or can be collected from a healthy subject. The term subject can be used interchangeably with patient or individual. The patient can be a human patient.

As used herein, the term "determining an expression level" or "determining an expression profile" or "detecting an expression level" or "detecting an expression profile" as used in reference to a biomarker or classifier means the application of a biomarker specific reagent such as a probe, primer or antibody and/or a method to a sample, for example a sample of the subject or patient and/or a control sample, for ascertaining or measuring quantitatively, semi-quantitatively or qualitatively the amount of a biomarker or biomarkers, for example the amount of biomarker polypeptide or mRNA (or cDNA derived therefrom). For example, a level of a biomarker can be determined by a number of methods including for example immunoassays including for example immunohistochemistry, ELISA, Western blot, immunoprecipitation and the like, where a biomarker detection agent such as an antibody for example, a labeled antibody, specifically binds the biomarker and permits for example relative or absolute ascertaining of the amount of polypeptide biomarker, hybridization and PCR protocols where a probe or primer or primer set are used to ascertain the amount of nucleic acid biomarker, including for example probe based and amplification based methods including for example microarray analysis, RT-PCR such as quantitative RT-PCR (qRT-PCR), serial analysis of gene expression (SAGE), Northern Blot, digital molecular barcoding technology, for example Nanostring Counter Analysis, and TaqMan quantitative PCR assays. Other methods of mRNA detection and quantification can be applied, such as mRNA in situ hybridization in formalin-fixed, paraffin-embedded (FFPE) tissue samples or cells. This technology is currently offered by the QuantiGene ViewRNA (Affymetrix), which uses probe sets for each mRNA that bind specifically to an amplification system to amplify the hybridization signals; these amplified signals can be visualized using a standard fluorescence microscope or imaging system. This system for example can detect and measure transcript levels in heterogeneous samples; for example, if a sample has normal and tumor cells present in the same tissue section. As mentioned, TaqMan probe-based gene expression analysis (PCR-based) can also be used for measuring gene expression levels in tissue samples, and this technology has been shown to be useful for measuring mRNA levels in FFPE samples. In brief, TaqMan probe-based assays utilize a probe that hybridizes specifically to the mRNA target. This probe contains a quencher dye and a reporter dye (fluorescent molecule) attached to each end, and fluorescence is emitted only when specific hybridization to the mRNA target occurs. During the amplification step, the exonuclease activity of the polymerase enzyme causes the quencher and the reporter dyes to be detached from the probe, and fluorescence emission can occur. This fluorescence emission is recorded and signals are measured by a detection system; these signal intensities are used to calculate the abundance of a given transcript (gene expression) in a sample.

The "biomarkers" or "classifier biomarkers" of the invention include genes and proteins, and variants and fragments thereof. Such biomarkers include DNA comprising the entire or partial sequence of the nucleic acid sequence encoding the biomarker, or the complement of such a sequence. The biomarker nucleic acids also include any expression product or portion thereof of the nucleic acid sequences of interest. A biomarker protein is a protein encoded by or corresponding to a DNA biomarker of the invention. A biomarker protein comprises the entire or partial amino acid sequence of any of the biomarker proteins or polypeptides. The biomarker nucleic acid can be extracted from a cell or can be cell free or extracted from an extracellular vesicular entity such as an exosome.

A "biomarker" is any gene or protein whose level of expression in a tissue or cell is altered compared to that of a normal or healthy cell or tissue. The detection, and in some cases the level, of the biomarkers of the invention permits the differentiation of samples.

The biomarker panels and methods provided herein are used in various aspects, to assess whether a patient's lung cancer (adenocarcinoma) sample is proximal inflammatory (squamoid), proximal proliferative (magnoid) or terminal respiratory unit (bronchioid). In one embodiment, as described herein, the methods provided herein are used in various aspects, to assess, whether a patient's lung cancer (squamous) sample as Primitive, Classical, Secretory, or Basal. In a further embodiment, the methods provided herein are used to determine the likelihood of a patient responding to PARP inhibitor treatment based on the AD or SQ subtype determined by the biomarker panels and methods described herein. The PARP inhibitor treatment can be any PARP inhibitor treatment provided herein.

A biomarker capable of reliable classification can be one that is upregulated (e.g., expression is increased) or downregulated (e.g., expression is decreased) relative to a control. The control can be any control as provided herein.

In one embodiment, the biomarkers panels, or subsets thereof, are those disclosed in any publically available AD and/or SQ gene expression datasets. In one embodiment, the lung cancer is AD and the biomarker panel or subset thereof is, for example, the cancer genome atlas (TCGA) lung AD RNAseq gene expression dataset (n=515). In one embodiment, the lung cancer is AD and the biomarker panel or subset thereof is, for example, the AD gene expression dataset (n=442) disclosed in Shedden et al. (Nat Med 2008; 14(8): 822-827), the contents of which are herein incorporated by reference in its entirety. In one embodiment, the lung cancer is AD and the biomarker panel or subset thereof is, for example, the AD gene expression dataset (n=117) disclosed in Tomida et al. (J Clin Oncol 2009; 27(17):2793-2799), the contents of which are herein incorporated by reference in its entirety. In one embodiment, the lung cancer is AD and the biomarker panel or subset thereof is, for example, the AD gene expression dataset (n=116) disclosed in Wilkerson et al. (PLoS One 2012; 7(5):e36530), the contents of which are herein incorporated by reference in its entirety. In one embodiment, the lung cancer is AD and the biomarker panel or subset thereof is, for example, the AD gene expression dataset disclosed in Table 1. In one embodiment, the lung cancer is AD and the biomarker panel or subset thereof is, for example, the AD gene expression dataset disclosed in Table 1 in combination with one or more biomarkers from a publically available AD expression dataset. In Table 2, the first column of the table represents the biomarker list for distinguishing Terminal Respiratory Unit (TRU). The middle column of the table represents the biomarker list for distinguishing Proximal Proliferative (PP). The last column of the table represents the biomarker list for distinguishing Proximal Inflammatory (PI). In some cases, as shown in Table 2, a total of 48 biomarkers can be used for AD subtype determination. For each AD subtype, 8 of the 16 biomarkers can be negatively correlated genes, while 8 can be positively correlated genes which can be selected as the gene signature of a specific AD subtype.

In one embodiment, the lung cancer is SQ and the biomarker panel or subset thereof is, for example, TCGA lung SQ RNAseq gene expression dataset (n=501). In one embodiment, the lung cancer is SQ and the biomarker panel or subset thereof is, for example, the SQ gene expression dataset (n=75) disclosed in Lee et al. (Cancer Res 2008; 14(22): 7397-7404), the contents of which are herein incorporated by reference in its entirety. In one embodiment, the lung cancer is SQ and the biomarker panel or subset thereof is, for example, the SQ gene expression dataset (n=130) disclosed in Raponi et al. (Cancer Res 2006: 66(7): 466-472), the contents of which are herein incorporated by reference in its entirety. In one embodiment, the lung cancer is SQ and the biomarker panel or subset thereof is, for example, the SQ gene expression dataset (n=56) disclosed in Wilkerson et al. (Clin Cancer Res 2010; 16(19):4864-4875), the contents of which are herein incorporated by reference in its entirety. In one embodiment, the lung cancer is SQ and the biomarker panel or subset thereof is, for example, the SQ gene expression dataset disclosed in Table 3. In one embodiment, the lung cancer is SQ and the biomarker panel or subset thereof is, for example, the SQ gene expression dataset disclosed in Table 3 in combination with one or more biomarkers from a publically available SQ expression dataset. In Table 4, the first column of the table represents the biomarker list for distinguishing basal. The second column of the table represents the biomarker list for classical. The third column of the table represents the biomarker list for distinguishing primitive. The last column of the table represents the biomarker list for distinguishing secretory. In some cases, as shown in Table 4, a total of 80 biomarkers can be used for SQ subtype determination. For each SQ subtype in Table 4, 10 of the 20 biomarkers can be negatively correlated genes, while 10 can be positively correlated genes which can be selected as the gene signature of a specific SQ subtype.

In general, the methods provided herein are used to classify a lung cancer sample as a particular lung cancer subtype (i.e., subtype of adenocarcinoma or squamous cell carcinoma). In one embodiment, the lung cancer sample obtained from the patient has been previously diagnosed as being AD, and the methods provided herein are used to determine the AD subtype of the lung cancer sample. In one embodiment, the lung cancer sample obtained from the patient has been previously diagnosed as being SQ, and the methods provided herein are used to determine the SQ subtype of the lung cancer sample. In one embodiment, the method comprises detecting or determining an expression level of at least five of the classifier biomarkers of an AD or SQ biomarker set provided herein. In one embodiment, the sample is an AD lung sample obtained from the patient, and the biomarker set is selected from Table 1. In one embodiment, the sample is an SQ lung sample obtained from the patient, and the biomarker set is selected from Table 3. In one embodiment, the detecting step is at the nucleic acid level by performing RNA-seq, a reverse transcriptase polymerase chain reaction (RT-PCR) or a hybridization assay with oligonucleotides that are substantially complementary to portions of cDNA molecules of the at least five classifier biomarkers of a biomarker set provided herein (e.g., Table 1 for an AD lung sample and/or Table 3 for a SQ lung sample) under conditions suitable for RNA-seq, RT-PCR or hybridization and obtaining expression levels of the at least five classifier biomarkers based on the detecting step. The expression levels of the at least five of the classifier biomarkers can then be compared to reference expression levels of the at least five of the classifier biomarkers of a biomarker set provided herein (e.g., Table 1 and/or Table 3) from at least one sample training set. The at least one sample training set can comprise, (i) expression levels(s) of the at least five biomarkers from a sample that overexpresses the at least five biomarkers, or overexpresses a subset of the at least five biomarkers, (ii) expression levels from a reference squamoid (proximal inflammatory), bronchoid (terminal respiratory unit) or magnoid (proximal proliferative) sample, (iii) expression levels from a reference primitive, classical, secretory or basal sample, (iii) expression levels from an adenocarcinoma free lung sample, or (iv) expression levels from a squamous cell carcinoma free lung sample and classifying the lung tissue sample as a squamoid (proximal inflammatory), bronchoid (terminal respiratory unit) a magnoid (proximal proliferative) subtype or a primitive, classical, secretory, or basal subtype. The lung cancer sample can then be classified as a bronchioid, squamoid, or magnoid subtype of adenocarcinoma or primitive, classical, secretory or basal subtype of squamous cell carcinoma based on the results of the comparing step. In one embodiment, the comparing step can comprise applying a statistical algorithm which comprises determining a correlation between the expression data obtained from the lung tissue or cancer sample and the expression data from the at least one training set(s) provided herein; and classifying the lung tissue or cancer sample as a squamoid (proximal inflammatory), bronchoid (terminal respiratory unit) or a magnoid (proximal proliferative) subtype or primitive, classical, secretory or basal subtype based on the results of the statistical algorithm.

In one embodiment, the method comprises probing the levels of at least five of the classifier biomarkers of a biomarker set provided herein (e.g., Table 1 for an AD lung sample and/or Table 3 for a SQ lung sample) at the nucleic acid level, in a lung cancer sample (e.g. AD or SQ lung cancer sample) obtained from the patient. The probing step, in one embodiment, comprises mixing the sample with five or more oligonucleotides that are substantially complementary to portions of cDNA molecules of the at least five classifier biomarkers of the biomarker set provided herein (e.g., Table 1 for an AD lung sample and/or Table 3 for a SQ lung sample) under conditions suitable for hybridization of the five or more oligonucleotides to their complements or substantial complements; detecting whether hybridization occurs between the five or more oligonucleotides to their complements or substantial complements; and obtaining hybridization values of the at least five classifier biomarkers based on the detecting step. The hybridization values of the at least five classifier biomarkers are then compared to reference hybridization value(s) from at least one sample training set. For example, the at least one sample training set comprises hybridization values from a reference squamoid (proximal inflammatory), bronchoid (terminal respiratory unit) or magnoid (proximal proliferative) sample or from a reference primitive, classical, secretory or basal sample. The lung cancer sample is classified, for example, as squamoid (proximal inflammatory), bronchoid (terminal respiratory unit) or magnoid (proximal proliferative) sample or a primitive, classical, secretory or basal sample based on the results of the comparing step.

The sample can be any sample isolated from a human subject or patient. For example, in one embodiment, the analysis is performed on lung biopsies that are embedded in paraffin wax. In one embodiment, the sample can be a fresh frozen lung tissue sample. In another embodiment, the sample can be a bodily fluid obtained from the patient. The bodily fluid can be blood or fractions thereof (i.e., serum, plasma), urine, saliva, sputum or cerebrospinal fluid (CSF). The sample can contain cellular as well as extracellular sources of nucleic acid for use in the methods provided herein. The extracellular sources can be cell-free DNA and/or exosomes. In one embodiment, the sample can be a cell pellet or a wash. This aspect of the invention provides a means to improve current diagnostics by accurately identifying the major histological types, even from small biopsies. The methods of the invention, including the RT-PCR methods, are sensitive, precise and have multianalyte capability for use with paraffin embedded samples. See, for example, Cronin et al. (2004) Am. J Pathol. 164(1):35-42, herein incorporated by reference.

Formalin fixation and tissue embedding in paraffin wax is a universal approach for tissue processing prior to light microscopic evaluation. A major advantage afforded by formalin-fixed paraffin-embedded (FFPE) specimens is the preservation of cellular and architectural morphologic detail in tissue sections. (Fox et al. (1985) J Histochem Cytochem 33:845-853). The standard buffered formalin fixative in which biopsy specimens are processed is typically an aqueous solution containing 37% formaldehyde and 10-15% methyl alcohol. Formaldehyde is a highly reactive dipolar compound that results in the formation of protein-nucleic acid and protein-protein crosslinks in vitro (Clark et al. (1986) J Histochem Cytochem 34:1509-1512; McGhee and von Hippel (1975) Biochemistry 14:1281-1296, each incorporated by reference herein).

Methods are known in the art for the isolation of RNA from FFPE tissue. In one embodiment, total RNA can be isolated from FFPE tissues as described by Bibikova et al. (2004) American Journal of Pathology 165:1799-1807, herein incorporated by reference. Likewise, the High Pure RNA Paraffin Kit (Roche) can be used. Paraffin is removed by xylene extraction followed by ethanol wash. RNA can be isolated from sectioned tissue blocks using the MasterPure Purification kit (Epicenter, Madison, Wis.); a DNase I treatment step is included. RNA can be extracted from frozen samples using Trizol reagent according to the supplier's instructions (Invitrogen Life Technologies, Carlsbad, Calif.). Samples with measurable residual genomic DNA can be resubjected to DNaseI treatment and assayed for DNA contamination. All purification, DNase treatment, and other steps can be performed according to the manufacturer's protocol. After total RNA isolation, samples can be stored at −80° C. until use.

General methods for mRNA extraction are well known in the art and are disclosed in standard textbooks of molecular biology, including Ausubel et al., ed., Current Protocols in Molecular Biology, John Wiley & Sons, New York 1987-1999. Methods for RNA extraction from paraffin embedded tissues are disclosed, for example, in Rupp and Locker (Lab Invest. 56:A67, 1987) and De Andres et al. (Biotechniques 18:42-44, 1995). In particular, RNA isolation can be performed using a purification kit, a buffer set and protease from commercial manufacturers, such as Qiagen (Valencia, Calif.), according to the manufacturer's instructions. For example, total RNA from cells in culture can be isolated using Qiagen RNeasy mini-columns. Other commercially available RNA isolation kits include MasterPure™ Complete DNA and RNA Purification Kit (Epicentre, Madison, Wis.) and Paraffin Block RNA Isolation Kit (Ambion, Austin, Tex.). Total RNA from tissue samples can be isolated, for example, using RNA Stat-60 (Tel-Test, Friendswood, Tex.). RNA prepared from a tumor can be isolated, for example, by cesium chloride density gradient centrifugation. Additionally, large numbers of tissue samples can readily be processed using techniques well known to those of skill in the art, such as, for example, the single-step RNA isolation process of Chomczynski (U.S. Pat. No. 4,843,155, incorporated by reference in its entirety for all purposes).

In one embodiment, a sample comprises cells harvested from a lung tissue sample, for example, an adenocarcinoma or squamous cell carcinoma sample. Cells can be harvested from a biological sample using standard techniques known in the art. For example, in one embodiment, cells are harvested by centrifuging a cell sample and resuspending the pelleted cells. The cells can be resuspended in a buffered solution such as phosphate-buffered saline (PBS). After centrifuging the cell suspension to obtain a cell pellet, the cells can be lysed to extract nucleic acid, e.g, messenger RNA. All samples obtained from a subject, including those subjected to any sort of further processing, are considered to be obtained from the subject.

The sample, in one embodiment, is further processed before the detection of the biomarker levels of the combination of biomarkers set forth herein. For example, mRNA in a cell or tissue sample can be separated from other components of the sample. The sample can be concentrated and/or purified to isolate mRNA in its non-natural state, as the mRNA is not in its natural environment. For example, studies have indicated that the higher order structure of mRNA in vivo differs from the in vitro structure of the same sequence (see, e.g., Rouskin et al. (2014). Nature 505, pp. 701-705, incorporated herein in its entirety for all purposes).

mRNA from the sample in one embodiment, is hybridized to a synthetic DNA probe, which in some embodiments, includes a detection moiety (e.g., detectable label, capture sequence, barcode reporting sequence). Accordingly, in these embodiments, a non-natural mRNA-cDNA complex is ultimately made and used for detection of the biomarker. In another embodiment, mRNA from the sample is directly labeled with a detectable label, e.g., a fluorophore. In a further embodiment, the non-natural labeled-mRNA molecule is hybridized to a cDNA probe and the complex is detected.

In one embodiment, once the mRNA is obtained from a sample, it is converted to complementary DNA (cDNA) in a hybridization reaction or is used in a hybridization reaction together with one or more cDNA probes. cDNA does not exist in vivo and therefore is a non-natural molecule. Furthermore, cDNA-mRNA hybrids are synthetic and do not exist in vivo. Besides cDNA not existing in vivo, cDNA is necessarily different than mRNA, as it includes deoxyribonucleic acid and not ribonucleic acid. The cDNA is then amplified, for example, by the polymerase chain reaction (PCR) or other amplification method known to those of ordinary skill in the art. For example, other amplification methods that may be employed include the ligase chain reaction (LCR) (Wu and Wallace, Genomics, 4:560 (1989), Landegren et al., Science, 241:1077 (1988), incorporated by reference in its entirety for all purposes, transcription amplification (Kwoh et al., *Proc. Natl. Acad. Sci. USA,* 86:1173 (1989), incorporated by reference in its entirety for all purposes), self-sustained sequence replication (Guatelli et al., *Proc. Nat. Acad. Sci. USA,* 87:1874 (1990), incorporated by reference in its entirety for all purposes), incorporated by reference in its entirety for all purposes, and nucleic acid based sequence amplification (NASBA). Guidelines for selecting primers for PCR amplification are known to those of ordinary skill in the art. See, e.g., McPherson et al., PCR Basics: From Background to Bench, Springer-Verlag, 2000, incorporated by reference in its entirety for all purposes. The product of this amplification reaction, i.e., amplified cDNA is also necessarily a non-natural product. First, as mentioned above, cDNA is a non-natural molecule. Second, in the case of PCR, the amplification process serves to create hundreds of millions of cDNA copies for every individual cDNA molecule of starting material. The number of copies generated are far removed from the number of copies of mRNA that are present in vivo.

In one embodiment, cDNA is amplified with primers that introduce an additional DNA sequence (e.g., adapter, reporter, capture sequence or moiety, barcode) onto the fragments (e.g., with the use of adapter-specific primers), or mRNA or cDNA biomarker sequences are hybridized directly to a cDNA probe comprising the additional sequence (e.g., adapter, reporter, capture sequence or moiety, barcode). Amplification and/or hybridization of mRNA to a cDNA probe therefore serves to create non-natural double stranded molecules from the non-natural single stranded cDNA, or the mRNA, by introducing additional sequences and forming non-natural hybrids. Further, as known to those of ordinary skill in the art, amplification procedures have error rates associated with them. Therefore, amplification introduces further modifications into the cDNA molecules. In one embodiment, during amplification with the adapter-specific primers, a detectable label, e.g., a fluorophore, is added to single strand cDNA molecules. Amplification therefore also serves to create DNA complexes that do not occur in nature, at least because (i) cDNA does not exist in vivo, (i) adapter sequences are added to the ends of cDNA molecules to make DNA sequences that do not exist in vivo, (ii) the error rate associated with amplification further creates DNA sequences that do not exist in vivo, (iii) the disparate structure of the cDNA molecules as compared to what exists in nature and (iv) the chemical addition of a detectable label to the cDNA molecules.

In some embodiments, the expression of a biomarker of interest is detected at the nucleic acid level via detection of non-natural cDNA molecules.

In some embodiments, the method for lung cancer subtyping (e.g., AD or SQ subtyping) includes detecting expression levels of a classifier biomarker set. The classifier biomarker set can be a set of biomarkers from a publically available database such as, for example, TCGA lung AD and/or SQ RNASeq gene expression dataset(s) or any other dataset provided herein. In some embodiments, the detecting includes all of the classifier biomarkers of Table 1, Table 3 or any other dataset provided herein at the nucleic acid level or protein level. In another embodiment, a single or a subset of the classifier biomarkers of Table 1, Table 3 or any other dataset provided herein are detected, for example, from about five to about twenty. In another embodiment, a single or a subset of the classifier biomarkers of Table 1 and/or any other dataset provided herein are detected, for example, from about 16 to about 48. In yet another embodiment, a single or a subset of the classifier biomarkers of Table 3 and/or any other dataset provided herein are detected, for example, from about 20 to about 80. In another embodiment, all of the classifier biomarkers of Table 1, Table 3 or any other dataset provided herein are detected. In another embodiment, at least one or all of the classifier biomarkers of Table 1 in combination with one or more classifier biomarkers of any other AD dataset provided herein are detected. In another embodiment, at least one or all of the classifier biomarkers of Table 3 in combination with one or more classifier biomarkers of any other SQ dataset provided herein are detected. The detecting can be performed by any suitable technique including, but not limited to, RNA-seq, a reverse transcriptase polymerase chain reaction (RT-PCR), a microarray hybridization assay, or another hybridization assay, e.g., a NanoString assay for example, with primers and/or probes specific to the classifier biomarkers, and/or the like.

The biomarkers described herein include RNA comprising the entire or partial sequence of any of the nucleic acid sequences of interest, or their non-natural cDNA product, obtained synthetically in vitro in a reverse transcription reaction. The term "fragment" is intended to refer to a portion of the polynucleotide that generally comprise at least 10, 15, 20, 50, 75, 100, 150, 200, 250, 300, 350, 400, 450, 500, 550, 600, 650, 700, 800, 900, 1,000, 1,200, or 1,500 contiguous nucleotides, or up to the number of nucleotides present in a full-length biomarker polynucleotide disclosed herein. A fragment of a biomarker polynucleotide will generally encode at least 15, 25, 30, 50, 100, 150, 200, or 250 contiguous amino acids, or up to the total number of amino acids present in a full-length biomarker protein of the invention.

In some embodiments, overexpression, such as of an RNA transcript or its expression product, is determined by normalization to the level of reference RNA transcripts or their expression products, which can be all measured transcripts (or their products) in the sample or a particular reference set of RNA transcripts (or their non-natural cDNA products). Normalization is performed to correct for or normalize away both differences in the amount of RNA or cDNA assayed and variability in the quality of the RNA or cDNA used. Therefore, an assay typically measures and incorporates the expression of certain normalizing genes, including well known housekeeping genes, such as, for example, GAPDH and/or β-Actin. Alternatively, normalization can be based on the mean or median signal of all of the assayed biomarkers or a large subset thereof (global normalization approach).

For example, in one embodiment, from about 1 to about 5, about 5 to about 10, from about 5 to about 15, from about 5 to about 20, from about 5 to about 25, from about 5 to about 30, from about 5 to about 35, from about 5 to about 40, from about 5 to about 45, from about 5 to about 50, from about 5 to about 55, from about 5 to about 60, from about 5 to about 65, from about 5 to about 70, from about 5 to about 75, or from about 5 to about 80, of the biomarkers in any of the AD or SQ gene expression datasets provided herein, including, for example, Table 1 for an AD lung sample or Table 3 for a SQ lung sample. In another embodiment, each of the biomarkers from any one of the AD or SQ gene expression datasets provided herein, including, for example, Table 1 for an AD lung sample or Table 3 for a SQ lung sample are detected in a method to determine the lung cancer subtype.

TABLE 1

Gene Centroids of 48 Classifier Biomarkers for the Lung Adenocarcinoma (AD) Subtypes

| Gene # | Gene Symbol | Gene Name | Terminal Respiratory Unit (TRU) | Proximal Proliferative (PP) | Proximal Inflammatory (PI) | GenBank Acession Number* |
|---|---|---|---|---|---|---|
| 1 | FIGF | C-fos-induced growth factor | 2.129901586 | −1.173222174 | −1.545843019 | AY874421.1 |
| 2 | CTSH | Cathepsin H | 1.099895637 | −0.797376345 | −0.531006607 | NM_004390.4 |
| 3 | SCTR | Secretin receptor | 2.043898366 | −1.911062476 | −1.836386831 | NM_002980.2 |
| 4 | CYP4B1 | Cytochrome P450 family 4 subfamily B member 1 | 2.462733828 | −1.447070454 | −1.481195844 | NM_001319161.1 |
| 5 | GPR116 | G protein-coupled receptor 116 | 1.289460077 | −0.972597916 | −0.731487829 | AY140958.1 |
| 6 | ADH1B | Alcohol dehydrogenase 1B (class I) | 2.013525076 | −1.580299515 | −1.094580574 | NM_001286650.1 |
| 7 | CBX7 | Chromobox 7 | 0.728027298 | −0.698222051 | −0.243583657 | NM_175709.3 |
| 8 | HLF | Hepatic leukemia factor | 1.479193357 | −1.28826965 | −1.018563422 | M95585.1 |
| 9 | CEP55 | Centrosomal protein 55 | −1.524932169 | 0.5743319 | 0.580921528 | NM_018131.4 |
| 10 | TPX2 | Tpx2, Microtubule-associated | −1.704080763 | 0.587761579 | 0.583674937 | NM_012112.4 |
| 11 | BUB1B | BUB1 mitotic checkpoint serine/threonine kinase B | −1.531514951 | 0.769199954 | 0.543731288 | AF107297.1 |
| 12 | KIF4A | Kinesin family member 4A | −1.794045266 | 0.570328759 | 0.599399471 | NM_012310.4 |
| 13 | CCNB2 | Cyclin B2 | −1.442466223 | 0.602807712 | 0.526093335 | NM_004701.3 |
| 14 | KIF14 | Kinesin family member 14 | −1.66445145 | 0.762295222 | 0.543132477 | NM_014875.2 |
| 15 | MELK | Maternal embryonic leucine zipper kinase | −1.685012297 | 0.584181432 | 0.694064307 | NM_014791.3 |
| 16 | KIF11 | Kinesin family member 11 | −1.183768087 | 0.693181955 | 0.481955763 | NM_004523.3 |
| 17 | FGL1 | Fibrinogen like 1 | −0.978882607 | 4.89751413 | −1.958269455 | NM_004467.3 |
| 18 | PBK | PDZ binding kinase | −1.407694417 | 1.278522857 | 0.404652088 | NM_018492.3 |
| 19 | HSPD1 | Heat shock protein family D (Hsp60) member 1 | −0.469703958 | 0.624572377 | 0.111400174 | NM_002156.4 |
| 20 | TDG | Thymine DNA glycosylase | −0.351189471 | 0.60348929 | 0.076442589 | NM_003211.4 |
| 21 | PRC1 | Protein regulator of cytokinesis 1 | −1.159074285 | 0.797575854 | 0.461100041 | NM_003981.3 |
| 22 | DUSP4 | Dual specificity phosphatase 4 | −0.704273045 | 1.933259798 | −0.283343923 | NM_001394.6 |
| 23 | GTPBP4 | GTP binding protein 4 | −0.467281005 | 0.543583167 | 0.038904486 | NM_012341.2 |
| 24 | ZWINT | ZW10 interacting kinetochore protein | −1.062801846 | 0.741405035 | 0.418738839 | NM_007057.3 |
| 25 | TLR2 | Toll like receptor 2 | 0.672774085 | −1.389004155 | 0.098176794 | NM_001318787.1 |
| 26 | CD74 | CD74 molecule | 0.689011729 | −1.365243826 | 0.239872217 | NM_001025159.2 |
| 27 | HLA-DPB1 | Major histocompatibility complex, class II, DP beta 1 | 0.70548523 | −1.431001558 | 0.157288388 | M83664.1 |
| 28 | HLA-DPA1 | Major histocompatibility complex, class II, DP alpha 1 | 0.620746458 | −1.622212879 | 0.206805676 | NM_033554.3 |
| 29 | HLA-DRA | Major histocompatibility complex, class II, DR alpha | 0.47615106 | −1.517000712 | 0.209882138 | NM_019111.4 |
| 30 | ITGB2 | Integrin subunit beta 2 | 0.227015125 | −1.489015066 | 0.473986644 | NM_000211.4 |
| 31 | FAS | Fas cell surface death receptor | 0.120924174 | −1.244937359 | 0.608312102 | KM114217.1 |
| 32 | HLA-DRB1 | Major histocompatibility complex, class II, DR beta 1 | 0.561088415 | −1.639812592 | 0.272965507 | NM_002124.3 |
| 33 | PLAU | Plasminogen actuator, urokinase | −0.723116671 | −0.71054832 | 1.628730403 | NM_002658.4 |

TABLE 1-continued

Gene Centroids of 48 Classifier Biomarkers for the Lung Adenocarcinoma (AD) Subtypes

| Gene # | Gene Symbol | Gene Name | Terminal Respiratory Unit (TRU) | Proximal Proliferative (PP) | Proximal Inflammatory (PI) | GenBank Acession Number* |
|---|---|---|---|---|---|---|
| 34 | GBP1 | Guanylate binding protein 1 | −0.302372654 | −0.688857626 | 1.204326606 | NM_002053.2 |
| 35 | DSE | Dermatan sulfate epimerase | −0.101374419 | −0.602077696 | 0.748133278 | NM_013352.3 |
| 36 | CCDC109B | Coiled-coil domain containing 109B | −0.13855818 | −0.703783616 | 0.7964386 | BC002633.2 |
| 37 | TGFBI | Transforming growth factor beta induced | −0.328357044 | −0.746331889 | 1.164873128 | NM_000358.2 |
| 38 | CXCL10 | C-X-C motif chemokine ligand 10 | −0.434345777 | −0.62067894 | 1.70756508 | NM_001565.3 |
| 39 | LGALS1 | Lectin, galactoside binding soluble 1 | −0.291230377 | −0.549722715 | 0.957730776 | NM_002305.3 |
| 40 | TUBB6 | Tubulin beta 6 class V | 0.153163739 | −0.328431543 | 0.781293298 | M_032525.2 |
| 41 | GJB1 | Gap junction protein beta 1 | 1.567852415 | 0.672938467 | −3.61601989 | NM_001097642.2 |
| 42 | RAP1GAP | RAP1 GTPase activating protein | 1.019990653 | 0.138302482 | −1.426817837 | NM_001145658.1 |
| 43 | CACNA2D2 | Calcium voltage-gated channel auxiliary subunit alpha2delta 2 | 1.610819757 | −0.126189977 | −2.357279793 | NM_001005505.2 |
| 44 | SELENBP1 | Selenium binding protein 1 | 1.0475958 | −0.331350331 | −1.209058454 | NM_003944.3 |
| 45 | TFCP2L1 | Transcription factor CP2-like 1 | 0.218606218 | 0.952552471 | −1.320932951 | NM_014553.2 |
| 46 | SORBS2 | Sorbin and SH3 domain containing 2 | 0.603086366 | 0.462888705 | −1.412139816 | NM_001270771.1 |
| 47 | UNC13B | Unc-13 homolog B | 0.293706669 | 0.418115853 | −0.978505828 | NM_006377.3 |
| 48 | TACC2 | Transforming acidic coiled-coil containing protein 2 | 0.206302979 | 0.928437713 | −0.822332116 | AF220152.2 |

*Each GenBank Accession Number is a representative or exemplary GenBank Accession Number for the listed gene and is herein incorporated by reference in its entirety for all purposes. Further, each listed representative or exemplary accession number should not be construed to limit the claims to the specific accession number.

TABLE 2

Classifier Biomarkers for Terminal Respiratory Unit, Proximal Proliferative, and Proximal Inflammatory

| Terminal Respiratory Unit (TRU) | Proximal Proliferative (PP) | Proximal Inflammatory (PI) |
|---|---|---|
| CEP55 | TLR2 | GJB1 |
| TPX2 | CD74 | RAP1GAP |
| BUB1B | HLA-DPB1 | CACNA2D2 |
| KIF4A | HLA-DPA1 | SELENBP1 |
| CCNB2 | HLA-DRA | TFCP2L1 |
| KIF14 | ITGB2 | SORBS2 |
| MELK | FAS | UNC13B |
| KIF11 | HLA-DRB1 | TACC2 |
| HLF | ZWINT | TUBB6 |
| CBX7 | GTPBP4 | LGALS1 |
| ADH1B | DUSP4 | CXCL10 |
| GPR116 | PRC1 | TGFBI |
| CYP4B1 | TDG | CCDC109B |
| SCTR | HSPD1 | DSE |
| CTSH | PBK | GBP1 |
| FIGF | FGL1 | PLAU |

TABLE 3

Gene Centroids of the 80 Classifier Biomarkers for the Lung Squamous Cell Carcinoma (SQ) Subtypes

| Gene Number | Gene Symbol | Gene Name | basal | classical | primitive | secretory | GenBank Accession Number* |
|---|---|---|---|---|---|---|---|
| 1 | SERPINB4 | serpin family B member 4 | 15.1924 | −1.28178 | −10.0199 | −7.32845 | NM_002974.3 |
| 2 | CXCL1 | C-X-C motif chemokine ligand 1 | 14.47981 | −8.31954 | −8.37503 | 0.217875 | NM_001511.3 |
| 3 | S100A9 | S100 calcium binding protein A9 | 14.35103 | −5.8793 | −9.10206 | −1.88807 | NM_002965.3 |
| 4 | S100A8 | S100 calcium binding protein A8 | 14.00816 | −4.229 | −9.53669 | −3.08348 | NM_001319196.1 |
| 5 | SERPINB3 | serpin family B member 3 | 13.97538 | 1.502713 | −10.9279 | −8.54433 | NM_006919.2 |
| 6 | EPHA2 | EPHA2 | 12.36835 | −4.75069 | −8.27087 | −1.67711 | NM_004431.4 |

TABLE 3-continued

Gene Centroids of the 80 Classifier Biomarkers for the Lung Squamous Cell Carcinoma (SQ) Subtypes

| Gene Number | Gene Symbol | Gene Name | basal | classical | primitive | secretory | GenBank Accession Number* |
|---|---|---|---|---|---|---|---|
| 7 | S100A2 | S100 calcium binding protein A2 | 12.02474 | 2.060853 | −9.93545 | −7.83677 | NM_005978.3 |
| 8 | MMP10 | matrix metallopeptidase 10 | 11.70464 | −5.18263 | −3.79013 | −3.73457 | NM_002425.2 |
| 9 | IL4R | interleukin 4 receptor | 11.67838 | −11.2637 | −9.61741 | 7.418712 | NM_000418.3 |
| 10 | PDZK1IP1 | PDZK1-interacting protein 1 | 11.00384 | −9.67747 | −7.37829 | 4.707793 | NM_005764.3 |
| 11 | CDK5RAP2 | CDK5 regulatory subunit associated protein 2 | −13.3044 | 15.44094 | 0.582601 | −3.89079 | NM_018249.5 |
| 12 | FAM125B | family with sequence similarity 125, member B | −12.2853 | 4.665284 | 4.308726 | 4.558947 | BC028675.1 |
| 13 | CABC1 | chaperone activity of bc1 complex-like | −10.3757 | 4.343061 | 7.391224 | 0.672574 | AB073905.1 |
| 14 | ODC1 | ornithine decarboxylase 1 | −10.1908 | 15.84852 | 0.119301 | −7.30631 | NM_002539.2 |
| 15 | LPIN1 | lipin 1 | −10.134 | 3.748752 | 3.061368 | 4.230976 | NM_145693.2 |
| 16 | WASF1 | WAS protein family member 1 | −9.89134 | 18.55734 | 1.814068 | −11.9252 | NM_003931.2 |
| 17 | USP13 | ubiquitin specific peptidase 13 (isopeptidase T-3) | −9.17202 | 7.072314 | 7.133335 | −3.50892 | NM_003940.2 |
| 18 | NUP210 | nucleoporin 210 | −8.91997 | 5.496247 | 2.508106 | 1.366756 | NM_024923.3 |
| 19 | GLI2 | GLI Family Zinc Finger 2 | −8.58227 | 17.05556 | −5.643 | −6.1972 | NM_005270.4 |
| 20 | SPAG5 | sperm associated antigen 5 | −8.26995 | 8.478108 | 6.146636 | −5.34162 | NM_006461.3 |
| 21 | ME1 | malic enzyme 1 | −11.1058 | 21.38387 | −2.66141 | −10.605 | NM_002395.5 |
| 22 | TALDO1 | transaldolase 1 | −11.3472 | 21.05835 | −2.95802 | −9.76549 | NM_006755.1 |
| 23 | AKR1C3 | aldo-keto reductase family 1, member C3 | −6.34178 | 19.62236 | −6.31166 | −10.9917 | NM_003739.5 |
| 24 | TXN | thioredoxin | −7.28934 | 19.56185 | −6.64144 | −9.68306 | NM_003329.3 |
| 25 | ALDH3A1 | aldehyde dehydrogenase 3 family member A1 | −4.42445 | 19.16675 | −7.69158 | −11.4995 | NM_001135168.1 |
| 26 | CHST7 | carbohydrate sulfotransferase 7 | −6.70839 | 18.66004 | −5.80704 | −9.87835 | NM_019886.3 |
| 27 | ADAM23 | ADAM metallopeptidase domain 23 | −7.14726 | 18.4093 | −5.05087 | −9.67848 | NM_003812.3 |
| 28 | TUFT1 | tuftelin 1 | −6.31534 | 18.07229 | −4.12497 | −10.8461 | NM_020127.2 |
| 29 | FOXE1 | forkhead box E1 | −2.047 | 17.53642 | −9.74136 | −10.6746 | NM_004473.3 |
| 30 | ALDH3A2 | aldehyde dehydrogenase 3 family member A2 | −7.7634 | 15.83759 | −4.12228 | −6.78263 | NM_001031806.1 |
| 31 | PHC2 | polyhomeotic homolog 2 | 5.947711 | −19.3491 | 3.975339 | 12.79184 | NM_198040.2 |
| 32 | SLC43A3 | solute carrier family 43 member 3 | 2.164732 | −15.4786 | 4.435501 | 12.06209 | NM_014096.3 |
| 33 | CAPZB | capping actin protein of muscle Z-line beta subunit | 9.697325 | −15.4337 | −0.08505 | 7.331941 | NM_004930.4 |
| 34 | FAM46A | family with sequence similarity 46 member A | 9.050488 | −14.8822 | 0.551123 | 6.928165 | NM_017633.2 |
| 35 | PTP4A2 | protein tyrosine phosphatase type IVA, member 2 | 5.400389 | −14.838 | 1.837093 | 9.801226 | NM_080391.3 |
| 36 | DPYD | dihydropyrimidine dehydrogenase | 8.78203 | −14.5434 | −5.09695 | 10.92233 | NM_000110.3 |
| 37 | TRIM8 | tripartite motif containing 8 | 3.847394 | −14.5393 | −1.94247 | 13.84298 | NM_030912.2 |
| 38 | CD47 | CD47 molecule | 8.84354 | −14.3091 | −2.8533 | 8.964713 | NM_001777.3 |
| 39 | CRIP2 | cysteine rich protein 2 | 4.809366 | −14.1729 | 1.781357 | 9.711258 | NM_001312.3 |
| 40 | ST3GAL5 | ST3 beta-galactoside alpha-2,3-sialyltransferase 5 | 2.667885 | −13.865 | −1.29718 | 13.85595 | NM_003896.3 |
| 41 | HSF2 | heat shock transcription factor 2 | −5.79001 | 1.050968 | 11.39169 | −3.33599 | NM_004506.3 |
| 42 | MARCKSL1 | MARCKS like 1 | 1.317716 | −10.696 | 9.825417 | 3.621776 | NM_023009.6 |
| 43 | EFHD1 | EF-hand domain family member D1 | −2.47675 | −11.1247 | 9.620027 | 8.265181 | NM_025202.3 |
| 44 | CHKA | choline kinase alpha | −2.84869 | −7.08145 | 9.530024 | 4.135237 | NM_001277.2 |
| 45 | PLEKHB1 | pleckstrin homology domain containing B1 | −5.94374 | −6.54778 | 9.307835 | 6.960047 | NM_021200.2 |
| 46 | FNBP1L | formin binding protein 1 like | 2.207537 | −13.5657 | 9.226556 | 6.372445 | NM_001024948.2 |
| 47 | ZNF239 | zinc finger protein 239 | −2.61452 | −7.55963 | 8.698057 | 5.033708 | NM_005674.2 |
| 48 | ABI2 | Abelson interactor 2 | −8.51982 | 0.375002 | 8.621929 | 2.322745 | NM_001282925.1 |

TABLE 3-continued

Gene Centroids of the 80 Classifier Biomarkers for the Lung Squamous Cell Carcinoma (SQ) Subtypes

| Gene Number | Gene Symbol | Gene Name | basal | classical | primitive | secretory | GenBank Accession Number* |
|---|---|---|---|---|---|---|---|
| 49 | MYL6B | Myosin light chain 6B | −1.67839 | −4.74647 | 8.614632 | 0.913087 | NM_001199629.1 |
| 50 | TTLL4 | Tubulin Tyrosine Ligase Like 4 | −4.42597 | −4.4529 | 8.316108 | 3.698664 | NM_014640.4 |
| 51 | CLCA2 | Chloride Channel Accessory 2 | 11.3747 | 9.8531 | −13.5607 | −13.3641 | NM_006536.5 |
| 52 | GJB3 | Gap Junction Protein Beta 3 | 9.738857 | 1.975392 | −12.8741 | −3.19459 | NM_024009.2 |
| 53 | GPR87 | G Protein-Coupled Receptor 87 | 8.675319 | 3.714366 | −12.5406 | −4.28629 | NM_023915.3 |
| 54 | SFN | Stratifin | 9.34036 | 7.030931 | −12.0548 | −9.10453 | NM_006142.3 |
| 55 | CSTA | Cystatin A | 8.521125 | 6.642274 | −11.6462 | −8.09435 | NM_005213.3 |
| 56 | DSG3 | Desmoglein 3 | 8.011909 | 9.629873 | −11.4831 | −11.0649 | NM_001944.2 |
| 57 | ST6GALNAC2 | ST6 N-Acetylgalactosaminide Alpha-2,6-Sialyltransferase 2 | 3.15872 | 10.40711 | −11.4486 | −6.84553 | NM_006456.2 |
| 58 | GJB5 | Gap Junction Protein Beta 5 | 9.68863 | 5.741838 | −11.4122 | −8.47546 | NM_005268.3 |
| 59 | TMPRSS4 | Transmembrane Protease, Serine 4 | 7.421295 | 10.31518 | −10.907 | −11.6365 | NM_019894.3 |
| 60 | SDC1 | Syndecan 1 | 7.820035 | 8.717049 | −10.7889 | −10.3298 | NM_001006946.1 |
| 61 | FMNL1 | Formin Like 1 | −1.24826 | −12.3922 | −4.15625 | 18.39415 | NM_005892.3 |
| 62 | BIRC3 | Baculoviral IAP Repeat Containing 3 | 0.52973 | −12.5421 | −4.71506 | 17.09129 | NM_001165.4 |
| 63 | ARHGDIB | Rho GDP Dissociation Inhibitor Beta | 1.579196 | −12.7865 | −4.70303 | 16.25141 | NM_001175.6 |
| 64 | SH2B3 | SH2B Adaptor Protein 3 | −3.48062 | −9.12196 | −3.04569 | 16.23607 | NM_005475.2 |
| 65 | HLA-DPA1 | Major Histocompatibility Complex, Class II, DP Alpha 1 | −2.12031 | −9.65989 | −3.99607 | 16.09867 | NM_033554.3 |
| 66 | NCF4 | Neutrophil Cytosolic Factor 4 | 1.545361 | −11.6937 | −6.10253 | 16.0617 | NM_000631.4 |
| 67 | ACSL5 | Acyl-CoA Synthetase Long-Chain Family Member 5 | 1.654978 | −14.5012 | −1.66186 | 15.91216 | NM_016234.3 |
| 68 | CSF2RA | Colony Stimulating Factor 2 Receptor Alpha Subunit | −1.37456 | −10.508 | −2.90331 | 15.48108 | NM_006140.4 |
| 69 | LAPTM5 | Lysosomal Protein Transmembrane 5 | −1.16591 | −9.77656 | −4.28777 | 15.43442 | NM_006762.2 |
| 70 | ARL6IP5 | ADP-ribosylation like fator 6 interacting protein 5 | 3.195006 | −13.6479 | −4.55752 | 15.41665 | NM_006407.3 |
| 71 | ADH7 | Alcohol Dehydrogenase 7 (Class IV), Mu Or Sigma | 0.182052 | 20.14673 | −9.26939 | −16.3334 | NM_001166504.1 |
| 72 | ABCC5 | ATP Binding Cassette Subfamily C Member 5 | −1.26645 | 17.73313 | −4.3337 | −15.6431 | NM_005688.3 |
| 73 | SOX2 | SRY-Box 2 | −2.70147 | 15.71135 | 0.455164 | −15.3051 | NM_003106.3 |
| 74 | SLC9A3R1 | Solute Carrier Family 9, Subfamily A (NHE3, Cation Proton Antiporter 3), Member 3 Regulator 1 | 1.902295 | 17.71886 | −9.60834 | −15.1497 | NM_004252.4 |
| 75 | KLF5 | Kruppel-Like Factor 5 (Intestinal) | 4.456364 | 13.41893 | −8.16611 | −14.0138 | NM_001730.4 |
| 76 | GPX2 | Glutathione Peroxidase 2 | −2.8397 | 17.49375 | −3.93026 | −14.0021 | NM_002083.3 |
| 77 | PIR | Pirin | −4.58676 | 16.97955 | −1.18296 | −13.5651 | NM_003662.3 |
| 78 | TPD52L1 | Tumor Protein D52-Like 1 | 1.334706 | 10.49961 | 0.210322 | −13.4769 | NM_003287.3 |
| 79 | SLC6A8 | Solute Carrier Family 6 Member 8 | 3.006892 | 11.83057 | −4.32575 | −13.4647 | NM_005629.3 |
| 80 | SIAH2 | Siah E3 Ubiquitin Protein Ligase 2 | 1.897743 | 11.60785 | −2.92619 | −13.0552 | NM_005067.5 |

*Each GenBank Accession Number is a representative or exemplary GenBank Accession Number for the listed gene and is herein incorporated by reference in its entirety for all purposes. Further, each listed representative or exemplary accession number should not be construed to limit the claims to the specific accession number.

TABLE 4

Classifier Biomarkers Selected for Basal, Classical, Primitive and Secretory SQ Subtypes

| Basal | Classical | Primitive | Secretory |
|---|---|---|---|
| SERPINB4 | ME1 | HSF2 | FMNL1 |
| CXCL1 | TALDO1 | MARCKSL1 | BIRC3 |
| S100A9 | AKR1C3 | EFHD1 | ARHGD1B |
| S100A8 | TXN | CHKA | SH2B3 |
| SERPINB3 | ALDH3A1 | PLEKHB1 | HLA-DPA1 |
| EPHA2 | CHST7 | FNBP1L | NCF4 |
| S100A2 | ADAM23 | ZNF239 | ACSL5 |
| MMP10 | TUFT1 | AB12 | CSF2RA |
| IL4R | FOXE1 | MYL6B | LAPTM5 |
| PDZK1LP1 | ALDH3A2 | TTLL4 | ARL61P5 |
| CDK5RAP2 | PHC2 | CLCA2 | ADH7 |
| FAM125B | SLC43A3 | GJB3 | ABCC5 |
| CABC1 | CAPZB | GPR87 | SOX2 |
| CDC1 | FAM46A | SFN | SLC9A3R1 |
| LPIN1 | PTP4A2 | CSTA | KLF5 |
| WASF1 | DPYD | DSG3 | GPX2 |
| USP13 | TRIM8 | ST6GALNAC2 | PIR |
| NUP210 | CD47 | GJB5 | TPD52L1 |
| GL12 | CRIP2 | TMPRSS4 | SLC6A8 |
| SPAG5 | ST3GAL5 | SDC1 | SIAH2 |

Isolated mRNA can be used in hybridization or amplification assays that include, but are not limited to, Southern or Northern analyses, PCR analyses and probe arrays, NanoString Assays. One method for the detection of mRNA levels involves contacting the isolated mRNA or synthesized cDNA with a nucleic acid molecule (probe) that can hybridize to the mRNA encoded by the gene being detected. The nucleic acid probe can be, for example, a cDNA, or a portion thereof, such as an oligonucleotide of at least 7, 15, 30, 50, 100, 250, or 500 nucleotides in length and sufficient to specifically hybridize under stringent conditions to the non-natural cDNA or mRNA biomarker of the present invention.

As explained above, in one embodiment, once the mRNA is obtained from a sample, it is converted to complementary DNA (cDNA) in a hybridization reaction. Conversion of the mRNA to cDNA can be performed with oligonucleotides or primers comprising sequence that is complementary to a portion of a specific mRNA. Conversion of the mRNA to cDNA can be performed with oligonucleotides or primers comprising random sequence. Conversion of the mRNA to cDNA can be performed with oligonucleotides or primers comprising sequence that is complementary to the poly(A) tail of an mRNA. cDNA does not exist in vivo and therefore is a non-natural molecule. In a further embodiment, the cDNA is then amplified, for example, by the polymerase chain reaction (PCR) or other amplification method known to those of ordinary skill in the art. The product of this amplification reaction, i.e., amplified cDNA is necessarily a non-natural product. As mentioned above, cDNA is a non-natural molecule. Second, in the case of PCR, the amplification process serves to create hundreds of millions of cDNA copies for every individual cDNA molecule of starting material. The number of copies generated is far removed from the number of copies of mRNA that are present in vivo.

In one embodiment, cDNA is amplified with primers that introduce an additional DNA sequence (adapter sequence) onto the fragments (with the use of adapter-specific primers). The adaptor sequence can be a tail, wherein the tail sequence is not complementary to the cDNA. Amplification therefore serves to create non-natural double stranded molecules from the non-natural single stranded cDNA, by introducing barcode, adapter and/or reporter sequences onto the already non-natural cDNA. In one embodiment, during amplification with the adapter-specific primers, a detectable label, e.g., a fluorophore, is added to single strand cDNA molecules. Amplification therefore also serves to create DNA complexes that do not occur in nature, at least because (i) cDNA does not exist in vivo, (i) adapter sequences are added to the ends of cDNA molecules to make DNA sequences that do not exist in vivo, (ii) the error rate associated with amplification further creates DNA sequences that do not exist in vivo, (iii) the disparate structure of the cDNA molecules as compared to what exists in nature and (iv) the chemical addition of a detectable label to the cDNA molecules.

In one embodiment, the synthesized cDNA (for example, amplified cDNA) is immobilized on a solid surface via hybridization with a probe, e.g., via a microarray. In another embodiment, cDNA products are detected via real-time polymerase chain reaction (PCR) via the introduction of fluorescent probes that hybridize with the cDNA products. For example, in one embodiment, biomarker detection is assessed by quantitative fluorogenic RT-PCR (e.g., with TaqMan® probes). For PCR analysis, well known methods are available in the art for the determination of primer sequences for use in the analysis.

Biomarkers provided herein in one embodiment, are detected via a hybridization reaction that employs a capture probe and/or a reporter probe. For example, the hybridization probe is a probe derivatized to a solid surface such as a bead, glass or silicon substrate. In another embodiment, the capture probe is present in solution and mixed with the patient's sample, followed by attachment of the hybridization product to a surface, e.g., via a biotin-avidin interaction (e.g., where biotin is a part of the capture probe and avidin is on the surface). The hybridization assay, in one embodiment, employs both a capture probe and a reporter probe. The reporter probe can hybridize to either the capture probe or the biomarker nucleic acid. Reporter probes e.g., are then counted and detected to determine the level of biomarker(s) in the sample. The capture and/or reporter probe, in one embodiment contain a detectable label, and/or a group that allows functionalization to a surface.

For example, the nCounter gene analysis system (see, e.g., Geiss et al. (2008) Nat. Biotechnol. 26, pp. 317-325, incorporated by reference in its entirety for all purposes, is amenable for use with the methods provided herein.

Hybridization assays described in U.S. Pat. Nos. 7,473, 767 and 8,492,094, the disclosures of which are incorporated by reference in their entireties for all purposes, are amenable for use with the methods provided herein, i.e., to detect the biomarkers and biomarker combinations described herein.

Biomarker levels may be monitored using a membrane blot (such as used in hybridization analysis such as Northern, Southern, dot, and the like), or microwells, sample tubes, gels, beads, or fibers (or any solid support comprising bound nucleic acids). See, for example, U.S. Pat. Nos. 5,770,722, 5,874,219, 5,744,305, 5,677,195 and 5,445,934, each incorporated by reference in their entireties.

In one embodiment, microarrays are used to detect biomarker levels. Microarrays are particularly well suited for this purpose because of the reproducibility between different experiments. DNA microarrays provide one method for the simultaneous measurement of the expression levels of large numbers of genes. Each array consists of a reproducible pattern of capture probes attached to a solid support. Labeled RNA or DNA is hybridized to complementary probes on the array and then detected by laser scanning Hybridization intensities for each probe on the array are determined and converted to a quantitative value representing relative gene expression levels. See, for example, U.S. Pat. Nos. 6,040,138, 5,800,992 and 6,020,135, 6,033,860, and 6,344,316, each incorporated by reference in their entireties. High-density oligonucleotide arrays are particularly useful for determining the gene expression profile for a large number of RNAs in a sample.

Techniques for the synthesis of these arrays using mechanical synthesis methods are described in, for example, U.S. Pat. No. 5,384,261. Although a planar array surface is generally used, the array can be fabricated on a surface of virtually any shape or even a multiplicity of surfaces. Arrays can be nucleic acids (or peptides) on beads, gels, polymeric surfaces, fibers (such as fiber optics), glass, or any other appropriate substrate. See, for example, U.S. Pat. Nos. 5,770,358, 5,789,162, 5,708,153, 6,040,193 and 5,800,992, each incorporated by reference in their entireties. Arrays can be packaged in such a manner as to allow for diagnostics or other manipulation of an all-inclusive device. See, for example, U.S. Pat. Nos. 5,856,174 and 5,922,591, each incorporated by reference in their entireties.

Serial analysis of gene expression (SAGE) in one embodiment is employed in the methods described herein. SAGE is a method that allows the simultaneous and quantitative analysis of a large number of gene transcripts, without the need of providing an individual hybridization probe for each transcript. First, a short sequence tag (about 10-14 bp) is generated that contains sufficient information to uniquely identify a transcript, provided that the tag is obtained from a unique position within each transcript. Then, many transcripts are linked together to form long serial molecules, that can be sequenced, revealing the identity of the multiple tags simultaneously. The expression pattern of any population of transcripts can be quantitatively evaluated by determining the abundance of individual tags, and identifying the gene corresponding to each tag. See, Velculescu et al. Science 270:484-87, 1995; Cell 88:243-51, 1997, incorporated by reference in its entirety.

An additional method of biomarker level analysis at the nucleic acid level is the use of a sequencing method, for example, RNAseq, next generation sequencing, and massively parallel signature sequencing (MPSS), as described by Brenner et al. (Nat. Biotech. 18:630-34, 2000, incorporated by reference in its entirety). This is a sequencing approach that combines non-gel-based signature sequencing with in vitro cloning of millions of templates on separate 5 µm diameter microbeads. First, a microbead library of DNA templates is constructed by in vitro cloning. This is followed by the assembly of a planar array of the template-containing microbeads in a flow cell at a high density (typically greater than $3.0 \times 10^6$ microbeads/cm$^2$). The free ends of the cloned templates on each microbead are analyzed simultaneously, using a fluorescence-based signature sequencing method that does not require DNA fragment separation. This method has been shown to simultaneously and accurately provide, in a single operation, hundreds of thousands of gene signature sequences from a yeast cDNA library.

Another method if biomarker level analysis at the nucleic acid level is the use of an amplification method such as, for example, RT-PCR or quantitative RT-PCR (qRT-PCR). Methods for determining the level of biomarker mRNA in a sample may involve the process of nucleic acid amplification, e.g., by RT-PCR (the experimental embodiment set forth in Mullis, 1987, U.S. Pat. No. 4,683,202), ligase chain reaction (Barany (1991) Proc. Natl. Acad. Sci. USA 88:189-193), self-sustained sequence replication (Guatelli et al. (1990) Proc. Natl. Acad. Sci. USA 87:1874-1878), transcriptional amplification system (Kwoh et al. (1989) Proc. Natl. Acad. Sci. USA 86:1173-1177), Q-Beta Replicase (Lizardi et al. (1988) Bio/Technology 6:1197), rolling circle replication (Lizardi et al., U.S. Pat. No. 5,854,033) or any other nucleic acid amplification method, followed by the detection of the amplified molecules using techniques well known to those of skill in the art. Numerous different PCR or qRT-PCR protocols are known in the art and can be directly applied or adapted for use using the presently described compositions for the detection and/or quantification of expression of discriminative genes in a sample. See, for example, Fan et al. (2004) Genome Res. 14:878-885, herein incorporated by reference. Generally, in PCR, a target polynucleotide sequence is amplified by reaction with at least one oligonucleotide primer or pair of oligonucleotide primers. The primer(s) hybridize to a complementary region of the target nucleic acid and a DNA polymerase extends the primer(s) to amplify the target sequence. Under conditions sufficient to provide polymerase-based nucleic acid amplification products, a nucleic acid fragment of one size dominates the reaction products (the target polynucleotide sequence which is the amplification product). The amplification cycle is repeated to increase the concentration of the single target polynucleotide sequence. The reaction can be performed in any thermocycler commonly used for PCR.

Quantitative RT-PCR (qRT-PCR) (also referred as real-time RT-PCR) is preferred under some circumstances because it provides not only a quantitative measurement, but also reduced time and contamination. As used herein, "quantitative PCR (or "real time qRT-PCR") refers to the direct monitoring of the progress of a PCR amplification as it is occurring without the need for repeated sampling of the reaction products. In quantitative PCR, the reaction products may be monitored via a signaling mechanism (e.g., fluorescence) as they are generated and are tracked after the signal rises above a background level but before the reaction reaches a plateau. The number of cycles required to achieve a detectable or "threshold" level of fluorescence varies directly with the concentration of amplifiable targets at the beginning of the PCR process, enabling a measure of signal intensity to provide a measure of the amount of target nucleic acid in a sample in real time. A DNA binding dye (e.g., SYBR green) or a labeled probe can be used to detect the extension product generated by PCR amplification. Any probe format utilizing a labeled probe comprising the sequences of the invention may be used.

Immunohistochemistry methods are also suitable for detecting the levels of the biomarkers of the present invention. Samples can be frozen for later preparation or immediately placed in a fixative solution. Tissue samples can be fixed by treatment with a reagent, such as formalin, gluteraldehyde, methanol, or the like and embedded in paraffin. Methods for preparing slides for immunohistochemical analysis from formalin-fixed, paraffin-embedded tissue samples are well known in the art.

In one embodiment, the levels of the biomarkers of the AD or SQ gene expression datasets provided herein, including, for example, Table 1 for an AD lung sample (or subsets thereof, for example 8 to 16, 16 to 32, or 32 to 48 biomarkers) or Table 3 for a SQ lung sample (or subsets thereof, for example 10 to 20, 20 to 40, 40 to 60 or 60 to 80 biomarkers), are normalized against the expression levels of all RNA transcripts or their non-natural cDNA expression products, or protein products in the sample, or of a reference set of RNA transcripts or a reference set of their non-natural cDNA expression products, or a reference set of their protein products in the sample.

As provided throughout, the methods set forth herein provide a method for determining the lung cancer subtype of a patient. Once the biomarker levels are determined, for example by measuring non-natural cDNA biomarker levels or non-natural mRNA-cDNA biomarker complexes, the biomarker levels are compared to reference values or a reference sample, for example with the use of statistical methods or direct comparison of detected levels, to make a determination of the lung cancer molecular subtype. Based on the comparison, the patient's lung cancer sample is classified, e.g., as squamoid (proximal inflammatory), bronchoid (terminal respiratory unit) or magnoid (proximal proliferative) or primitive, classical, secretory, or basal.

In one embodiment, expression level values of the at least five classifier biomarkers of the AD or SQ gene expression datasets provided herein, including, for example, Table 1 for an AD lung sample or Table 3 for a SQ lung sample are compared to reference expression level value(s) from at least one sample training set, wherein the at least one sample training set comprises expression level values from a reference sample(s). In a further embodiment, the at least one sample training set comprises expression level values of the at least five classifier biomarkers of the AD or SQ gene expression datasets provided herein, including, for example, Table 1 for an AD lung sample or Table 3 for a SQ lung sample from an adenocarcinoma sample, a squamous cell carcinoma sample, a neuroendocrine sample, a small cell lung carcinoma sample, a proximal inflammatory (squamoid), proximal proliferative (magnoid), a terminal respiratory unit (bronchioid) sample, a primitive, secretory, classical, basal or a combination thereof.

In a separate embodiment, hybridization values of the at least five classifier biomarkers of the AD or SQ gene expression datasets provided herein, including, for example, Table 1 for an AD lung sample or Table 3 for a SQ lung sample are compared to reference hybridization value(s) from at least one sample training set, wherein the at least one sample training set comprises hybridization values from a reference sample(s). In a further embodiment, the at least one sample training set comprises hybridization values of the at least five classifier biomarkers of the AD or SQ gene expression datasets provided herein, including, for example, Table 1 for an AD lung sample or Table 3 for a SQ lung sample from an adenocarcinoma sample, a squamous cell carcinoma sample, a proximal inflammatory (squamoid), proximal proliferative (magnoid), a terminal respiratory unit (bronchioid) sample, a primitive, secretory, classical, basal or a combination thereof.

TABLE A

Sample training set embodiments of the invention

| At least one sample training set | Origin of reference sample hybridization values | Lung cancer subtyping method |
|---|---|---|
| Embodiment 1 | proximal inflammatory (squamoid) reference sample, proximal proliferative (magnoid), and/or terminal respiratory unit (bronchioid) sample | Assessing whether patient sample is proximal inflammatory (squamoid), proximal proliferative (magnoid), or terminal respiratory unit (bronchioid) |
| Embodiment 2 | primitive reference sample, secretory, classical and/or basal sample | Assessing whether patient sample is primitive, classical, secretory, or basal |

Methods for comparing detected levels of biomarkers to reference values and/or reference samples are provided herein. Based on this comparison, in one embodiment a correlation between the biomarker levels obtained from the subject's sample and the reference values is obtained. An assessment of the lung cancer subtype is then made.

Various statistical methods can be used to aid in the comparison of the biomarker levels obtained from the patient and reference biomarker levels, for example, from at least one sample training set.

In one embodiment, a supervised pattern recognition method is employed. Examples of supervised pattern recognition methods can include, but are not limited to, the nearest centroid methods (Dabney (2005) Bioinformatics 21(22):4148-4154 and Tibshirani et al. (2002) Proc. Natl. Acad. Sci. USA 99(10):6576-6572); soft independent modeling of class analysis (SIMCA) (see, for example, Wold, 1976); partial least squares analysis (PLS) (see, for example, Wold, 1966; Joreskog, 1982; Frank, 1984; Bro, R., 1997); linear descriminant analysis (LDA) (see, for example, Nillson, 1965); K-nearest neighbour analysis (KNN) (sec, for example, Brown et al., 1996); artificial neural networks (ANN) (see, for example, Wasserman, 1989; Anker et al., 1992; Hare, 1994); probabilistic neural networks (PNNs) (see, for example, Parzen, 1962; Bishop, 1995; Speckt, 1990; Broomhead et al., 1988; Patterson, 1996); rule induction (RI) (see, for example, Quinlan, 1986); and, Bayesian methods (see, for example, Bretthorst, 1990a, 1990b, 1988). In one embodiment, the classifier for identifying tumor subtypes based on gene expression data is the centroid based method described in Mullins et al. (2007) Clin Chem. 53(7):1273-9, each of which is herein incorporated by reference in its entirety.

In other embodiments, an unsupervised training approach is employed, and therefore, no training set is used.

Referring to sample training sets for supervised learning approaches again, in some embodiments, a sample training set(s) can include expression data of all of the classifier biomarkers (e.g., all the classifier biomarkers of the AD or SQ gene expression datasets provided herein, including, for example, Table 1 for an AD lung sample or Table 3 for a SQ lung sample) from an adenocarcinoma sample. In some embodiments, a sample training set(s) can include expression data of all of the classifier biomarkers (e.g., all the classifier biomarkers of the AD or SQ gene expression datasets provided herein, including, for example, Table 1 for an AD lung sample or Table 3 for a SQ lung sample) from a squamous cell carcinoma sample, and/or an adenocarcinoma sample. In some embodiments, the sample training set(s) are normalized to remove sample-to-sample variation.

In some embodiments, comparing can include applying a statistical algorithm, such as, for example, any suitable multivariate statistical analysis model, which can be parametric or non-parametric. In some embodiments, applying the statistical algorithm can include determining a correlation between the expression data obtained from the human lung tissue sample and the expression data from the adenocarcinoma and squamous cell carcinoma training set(s). In some embodiments, cross-validation is performed, such as (for example), leave-one-out cross-validation (LOOCV). In some embodiments, integrative correlation is performed. In some embodiments, a Spearman correlation is performed. In some embodiments, a centroid based method is employed for the statistical algorithm as described in Mullins et al. (2007) Clin Chem. 53(7):1273-9, and based on gene expression data, which is herein incorporated by reference in its entirety.

Results of the gene expression performed on a sample from a subject (test sample) may be compared to a biological sample(s) or data derived from a biological sample(s) that is known or suspected to be normal ("reference sample" or "normal sample", e.g., non-adenocarcinoma sample). In some embodiments, a reference sample or reference gene expression data is obtained or derived from an individual known to have a particular molecular subtype of adenocarcimona, i.e., squamoid (proximal inflammatory), bronchoid (terminal respiratory unit) or magnoid (proximal proliferative). In some embodiments, a reference sample or reference gene expression data is obtained or derived from an individual known to have a particular molecular subtype of squamous cell carcinoma, i.e., primitive, classical, secretory, or basal.

The reference sample may be assayed at the same time, or at a different time from the test sample. Alternatively, the biomarker level information from a reference sample may be stored in a database or other means for access at a later date.

The biomarker level results of an assay on the test sample may be compared to the results of the same assay on a reference sample. In some cases, the results of the assay on the reference sample are from a database, or a reference value(s). In some cases, the results of the assay on the reference sample are a known or generally accepted value or range of values by those skilled in the art. In some cases the comparison is qualitative. In other cases the comparison is quantitative. In some cases, qualitative or quantitative comparisons may involve but are not limited to one or more of the following: comparing fluorescence values, spot intensities, absorbance values, chemiluminescent signals, histograms, critical threshold values, statistical significance values, expression levels of the genes described herein, mRNA copy numbers.

In one embodiment, an odds ratio (OR) is calculated for each biomarker level panel measurement. Here, the OR is a measure of association between the measured biomarker values for the patient and an outcome, e.g., lung cancer subtype. For example, see, *J. Can. Acad. Child Adolesc. Psychiatry* 2010; 19(3): 227-229, which is incorporated by reference in its entirety for all purposes.

In one embodiment, a specified statistical confidence level may be determined in order to provide a confidence level regarding the lung cancer subtype. For example, it may be determined that a confidence level of greater than 90% may be a useful predictor of the lung cancer subtype. In other embodiments, more or less stringent confidence levels may be chosen. For example, a confidence level of about or at least about 50%, 60%, 70%, 75%, 80%, 85%, 90%, 95%, 97.5%, 99%, 99.5%, or 99.9% may be chosen. The confidence level provided may in some cases be related to the quality of the sample, the quality of the data, the quality of the analysis, the specific methods used, and/or the number of gene expression values (i.e., the number of genes) analyzed. The specified confidence level for providing the likelihood of response may be chosen on the basis of the expected number of false positives or false negatives. Methods for choosing parameters for achieving a specified confidence level or for identifying markers with diagnostic power include but are not limited to Receiver Operating Characteristic (ROC) curve analysis, binormal ROC, principal component analysis, odds ratio analysis, partial least squares analysis, singular value decomposition, least absolute shrinkage and selection operator analysis, least angle regression, and the threshold gradient directed regularization method.

Determining the lung cancer subtype in some cases can be improved through the application of algorithms designed to normalize and or improve the reliability of the gene expression data. In some embodiments of the present invention, the data analysis utilizes a computer or other device, machine or apparatus for application of the various algorithms described herein due to the large number of individual data points that are processed. A "machine learning algorithm" refers to a computational-based prediction methodology, also known to persons skilled in the art as a "classifier," employed for characterizing a gene expression profile or profiles, e.g., to determine the lung cancer subtype. The biomarker levels, determined by, e.g., microarray-based hybridization assays, sequencing assays, NanoString assays, etc., are in one embodiment subjected to the algorithm in order to classify the profile. Supervised learning generally involves "training" a classifier to recognize the distinctions among classes (e.g., squamoid (proximal inflammatory) positive, bronchoid (terminal respiratory unit) positive or magnoid (proximal proliferative) positive, primitive positive, classical positive, secretory positive, or basal positive) and then "testing" the accuracy of the classifier on an independent test set. For new, unknown samples the classifier can be used to predict, for example, the class (e.g., TRU vs. PP vs. PI or primitive vs. secretory vs. classical vs. basal) in which the samples belong.

In some embodiments, a robust multi-array average (RMA) method may be used to normalize raw data. The RMA method begins by computing background-corrected intensities for each matched cell on a number of microarrays. In one embodiment, the background corrected values are restricted to positive values as described by Irizarry et al. (2003). Biostatistics April 4 (2): 249-64, incorporated by reference in its entirety for all purposes. After background correction, the base-2 logarithm of each background corrected matched-cell intensity is then obtained. The background corrected, log-transformed, matched intensity on each microarray is then normalized using the quantile normalization method in which for each input array and each probe value, the array percentile probe value is replaced with the average of all array percentile points, this method is more completely described by Bolstad et al. Bioinformatics 2003, incorporated by reference in its entirety. Following quantile normalization, the normalized data may then be fit to a linear model to obtain an intensity measure for each probe on each microarray. Tukey's median polish algorithm (Tukey, J. W., Exploratory Data Analysis. 1977, incorporated by reference in its entirety for all purposes) may then be used to determine the log-scale intensity level for the normalized probe set data.

Various other software programs may be implemented. In certain methods, feature selection and model estimation may be performed by logistic regression with lasso penalty using glmnet (Friedman et al. (2010). *Journal of statistical software* 33(1): 1-22, incorporated by reference in its entirety). Raw reads may be aligned using TopHat (Trapnell et al. (2009). *Bioinformatics* 25(9): 1105-11, incorporated by reference in its entirety). In methods, top features (N ranging from 10 to 200) are used to train a linear support vector machine (SVM) (Suykens J A K, Vandewalle J. Least Squares Support Vector Machine Classifiers. *Neural Processing Letters* 1999; 9(3): 293-300, incorporated by reference in its entirety) using the e1071 library (Meyer D. Support vector machines: the interface to libsvm in package e1071. 2014, incorporated by reference in its entirety). Confidence intervals, in one embodiment, are computed using the pROC package (Robin X, Turck N, Hainard A, et al. pROC: an open-source package for R and S+ to analyze and compare ROC curves. *BMC bioinformatics* 2011; 12: 77, incorporated by reference in its entirety).

In addition, data may be filtered to remove data that may be considered suspect. In one embodiment, data derived from microarray probes that have fewer than about 4, 5, 6, 7 or 8 guanosine+cytosine nucleotides may be considered to be unreliable due to their aberrant hybridization propensity or secondary structure issues. Similarly, data deriving from microarray probes that have more than about 12, 13, 14, 15, 16, 17, 18, 19, 20, 21, or 22 guanosine+cytosine nucleotides may in one embodiment be considered unreliable due to their aberrant hybridization propensity or secondary structure issues.

In some embodiments of the present invention, data from probe-sets may be excluded from analysis if they are not identified at a detectable level (above background).

In some embodiments of the present disclosure, probe-sets that exhibit no, or low variance may be excluded from further analysis. Low-variance probe-sets are excluded from the analysis via a Chi-Square test. In one embodiment, a probe-set is considered to be low-variance if its transformed variance is to the left of the 99 percent confidence interval of the Chi-Squared distribution with (N−1) degrees of freedom. (N−1)*Probe-set Variance/(Gene Probe-set Variance). about.Chi-Sq(N−1) where N is the number of input CEL files, (N−1) is the degrees of freedom for the Chi-Squared distribution, and the "probe-set variance for the gene" is the average of probe-set variances across the gene. In some embodiments of the present invention, probe-sets for a given mRNA or group of mRNAs may be excluded from further analysis if they contain less than a minimum number of probes that pass through the previously described filter steps for GC content, reliability, variance and the like. For example in some embodiments, probe-sets for a given gene or transcript cluster may be excluded from further analysis if they contain less than about 1, 2, 3, 4, 5, 6, 7, 8, 9, 10, 11, 12, 13, 14, 15, or less than about 20 probes.

Methods of biomarker level data analysis in one embodiment, further include the use of a feature selection algorithm as provided herein. In some embodiments of the present invention, feature selection is provided by use of the LIMMA software package (Smyth, G. K. (2005). Limma: linear models for microarray data. In: Bioinformatics and Computational Biology Solutions using R and Bioconductor, R. Gentleman, V. Carey, S. Dudoit, R. Irizarry, W. Huber (eds.), Springer, New York, pages 397-420, incorporated by reference in its entirety for all purposes).

Methods of biomarker level data analysis, in one embodiment, include the use of a pre-classifier algorithm. For example, an algorithm may use a specific molecular fingerprint to pre-classify the samples according to their composition and then apply a correction/normalization factor. This data/information may then be fed in to a final classification algorithm which would incorporate that information to aid in the final diagnosis.

Methods of biomarker level data analysis, in one embodiment, further include the use of a classifier algorithm as provided herein. In one embodiment of the present invention, a diagonal linear discriminant analysis, k-nearest neighbor algorithm, support vector machine (SVM) algorithm, linear support vector machine, random forest algorithm, or a probabilistic model-based method or a combination thereof is provided for classification of microarray data. In some embodiments, identified markers that distinguish samples (e.g., of varying biomarker level profiles, varying molecular subtypes of squamous cell carcinoma (e.g., primitive, classical, secretory, basal)) and/or varying molecular subtypes of adenocarcinoma (e.g., squamoid, bronchoid, magnoid)) are selected based on statistical significance of the difference in biomarker levels between classes of interest. In some cases, the statistical significance is adjusted by applying a Benjamin Hochberg or another correction for false discovery rate (FDR).

In some cases, the classifier algorithm may be supplemented with a meta-analysis approach such as that described by Fishel and Kaufman et al. 2007 Bioinformatics 23(13): 1599-606, incorporated by reference in its entirety for all purposes. In some cases, the classifier algorithm may be supplemented with a meta-analysis approach such as a repeatability analysis.

Methods for deriving and applying posterior probabilities to the analysis of biomarker level data are known in the art and have been described for example in Smyth, G. K. 2004 *Stat. Appi. Genet. Mol. Biol.* 3: Article 3, incorporated by reference in its entirety for all purposes. In some cases, the posterior probabilities may be used in the methods of the present invention to rank the markers provided by the classifier algorithm.

A statistical evaluation of the results of the biomarker level profiling may provide a quantitative value or values indicative of one or more of the following: molecular subtype of adenocarcinoma (squamoid, bronchoid or magnoid); molecular subtype of squamous cell carcinoma (primitive, classical, secretory, basal); the likelihood of the success of a particular therapeutic intervention, e.g., PARP inhibitor treatment. In one embodiment, the data is presented directly to the physician in its most useful form to guide patient care, or is used to define patient populations in clinical trials or a patient population for a given medication. The results of the molecular profiling can be statistically evaluated using a number of methods known to the art including, but not limited to: the students T test, the two sided T test, Pearson rank sum analysis, hidden Markov model analysis, analysis of q-q plots, principal component analysis, one way ANOVA, two way ANOVA, LIMMA and the like.

In some cases, accuracy may be determined by tracking the subject over time to determine the accuracy of the original diagnosis. In other cases, accuracy may be established in a deterministic manner or using statistical methods. For example, receiver operator characteristic (ROC) analysis may be used to determine the optimal assay parameters to achieve a specific level of accuracy, specificity, positive predictive value, negative predictive value, and/or false discovery rate.

In some cases the results of the biomarker level profiling assays, are entered into a database for access by representatives or agents of a molecular profiling business, the individual, a medical provider, or insurance provider. In some cases, assay results include sample classification, identification, or diagnosis by a representative, agent or consultant of the business, such as a medical professional. In other cases, a computer or algorithmic analysis of the data is provided automatically. In some cases the molecular profiling business may bill the individual, insurance provider, medical provider, researcher, or government entity for one or more of the following: molecular profiling assays performed, consulting services, data analysis, reporting of results, or database access.

In some embodiments of the present invention, the results of the biomarker level profiling assays are presented as a report on a computer screen or as a paper record. In some embodiments, the report may include, but is not limited to, such information as one or more of the following: the levels of biomarkers (e.g., as reported by copy number or fluorescence intensity, etc.) as compared to the reference sample or reference value(s); the likelihood the subject will respond to a particular therapy, based on the biomarker level values and the lung cancer subtype and proposed therapies.

In one embodiment, the results of the gene expression profiling may be classified into one or more of the following: squamoid (proximal inflammatory) positive, bronchoid (terminal respiratory unit) positive, magnoid (proximal proliferative) positive, squamoid (proximal inflammatory) negative, bronchoid (terminal respiratory unit) negative, magnoid (proximal proliferative) negative, primitive positive, classical positive, secretory positive, basal positive, primitive negative, classical negative, secretory negative, basal negative; likely to respond to PARP inhibitor treatment; unlikely to respond to PARP inhibitor treatment.

In some embodiments of the present invention, results are classified using a trained algorithm. Trained algorithms of the present invention include algorithms that have been developed using a reference set of known gene expression values and/or normal samples, for example, samples from individuals diagnosed with a particular molecular subtype of adenocarcinoma or squamous cell carcinoma. In some cases a reference set of known gene expression values are obtained from individuals who have been diagnosed with a particular molecular subtype of adenocarcinoma or squamous cell carcinoma, and are also known to respond (or not respond) to PARP inhibitor treatment.

Algorithms suitable for categorization of samples include but are not limited to k-nearest neighbor algorithms, support vector machines, linear discriminant analysis, diagonal linear discriminant analysis, updown, naive Bayesian algorithms, neural network algorithms, hidden Markov model algorithms, genetic algorithms, or any combination thereof.

When a binary classifier is compared with actual true values (e.g., values from a biological sample), there are typically four possible outcomes. If the outcome from a prediction is p (where "p" is a positive classifier output, such as the presence of a deletion or duplication syndrome) and the actual value is also p, then it is called a true positive (TP); however if the actual value is n then it is said to be a false positive (FP). Conversely, a true negative has occurred when both the prediction outcome and the actual value are n (where "n" is a negative classifier output, such as no deletion or duplication syndrome), and false negative is when the prediction outcome is n while the actual value is p. In one embodiment, consider a test that seeks to determine whether a person is likely or unlikely to respond to PARP inhibitor treatment. A false positive in this case occurs when the person tests positive, but actually does respond. A false negative, on the other hand, occurs when the person tests negative, suggesting they are unlikely to respond, when they actually are likely to respond. The same holds true for classifying a lung cancer subtype.

The positive predictive value (PPV), or precision rate, or post-test probability of disease, is the proportion of subjects with positive test results who are correctly diagnosed as likely or unlikely to respond, or diagnosed with the correct lung cancer subtype, or a combination thereof. It reflects the probability that a positive test reflects the underlying condition being tested for. Its value does however depend on the prevalence of the disease, which may vary. In one example the following characteristics are provided: FP (false positive); TN (true negative); TP (true positive); FN (false negative). False positive rate (alpha)=FP/(FP+TN)-specificity; False negative rate (beta)=FN/(TP+FN)-sensitivity; Power=sensitivity=1-beta; Likelihood-ratio positive=sensitivity/(1-specificity); Likelihood-ratio negative=(1-sensitivity)/specificity. The negative predictive value (NPV) is the proportion of subjects with negative test results who are correctly diagnosed.

In some embodiments, the results of the biomarker level analysis of the subject methods provide a statistical confidence level that a given diagnosis is correct. In some embodiments, such statistical confidence level is at least about, or more than about 85%, 90%, 91%, 92%, 93%, 94%, 95%, 96%, 97%, 98%, 99% 99.5%, or more.

In some embodiments, the method further includes classifying the lung tissue sample as a particular lung cancer subtype based on the comparison of biomarker levels in the sample and reference biomarker levels, for example present in at least one training set. In some embodiments, the lung tissue sample is classified as a particular subtype if the results of the comparison meet one or more criterion such as, for example, a minimum percent agreement, a value of a statistic calculated based on the percentage agreement such as (for example) a kappa statistic, a minimum correlation (e.g., Pearson's correlation) and/or the like.

It is intended that the methods described herein can be performed by software (stored in memory and/or executed on hardware), hardware, or a combination thereof. Hardware modules may include, for example, a general-purpose processor, a field programmable gate array (FPGA), and/or an application specific integrated circuit (ASIC). Software modules (executed on hardware) can be expressed in a variety of software languages (e.g., computer code), including Unix utilities, C, C++, Java™, Ruby, SQL, SAS®, the R programming language/software environment, Visual Basic™, and other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. Additional examples of computer code include, but are not limited to, control signals, encrypted code, and compressed code.

Some embodiments described herein relate to devices with a non-transitory computer-readable medium (also can be referred to as a non-transitory processor-readable medium or memory) having instructions or computer code thereon for performing various computer-implemented operations and/or methods disclosed herein. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to: magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other embodiments described herein relate to a computer program product, which can include, for example, the instructions and/or computer code discussed herein.

In some embodiments, a single biomarker, or from about 5 to about 10, from about 8 to about 16, from about 10 to about 20, from about 20 to about 30, from about 16 to about 32, from about 20 to about 40, from about 30 to about 40, from about 32 to about 48, from about 40 to about 50, from about 40 to about 60, from about 50 to about 60, from about 60 to about 70, from about 60 to about 80 or from about 70 to about 80 biomarkers (e.g., as disclosed in the AD or SQ gene expression datasets provided herein, including, for example, Table 1 for an AD lung sample or Table 3 for a SQ lung sample) is capable of classifying types and/or subtypes of lung cancer with a predictive success of at least about 70%, at least about 71%, at least about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, up to 100%, and all values in between. In some embodiments, any combination of biomarkers disclosed herein (e.g., in the AD or SQ gene expression datasets provided herein, including, for example, Table 1 for an AD lung sample or Table 3 for a SQ lung sample and sub-combinations thereof) can used to obtain a predictive success of at least about 70%, at least about 71%, at least about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, up to 100%, and all values in between.

In some embodiments, a single biomarker, or from about 5 to about 10, from about 8 to about 16, from about 10 to about 20, from about 20 to about 30, from about 16 to about 32, from about 20 to about 40, from about 30 to about 40, from about 32 to about 48, from about 40 to about 50, from about 40 to about 60, from about 50 to about 60, from about 60 to about 70, from about 60 to about 80 or from about 70 to about 80 biomarkers (e.g., as disclosed in the AD or SQ gene expression datasets provided herein, including, for example, Table 1 for an AD lung sample or Table 3 for a SQ lung sample) is capable of classifying lung cancer types and/or subtypes with a sensitivity or specificity of at least about 70%, at least about 71%, at least about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, up to 100%, and all values in between. In some embodiments, any combination of biomarkers disclosed herein can be used to obtain a sensitivity or specificity of at least about 70%, at least about 71%, at least about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, up to 100%, and all values in between.

In another embodiment, the methods of the invention require the detection of a total of at least 1, at least 2, at least 5, at least 8, at least 10, at least 16, at least 20, at least 30, at least 32, or up to 48 classifier biomarkers out of the 48 gene biomarkers of Table 1 in a lung cancer cell sample (e.g., lung AD sample) obtained from a patient in order to identify a TRU, a PP, or a PI lung adenocarcinoma subtype. The same applies for other classifier gene expression datasets as provided herein.

In one embodiment, at least 1, at least 2, at least 3, at least 4, at least 5, at least 6, at least 7, or up to 8 biomarkers of Table 1 are "up-regulated" in a specific subtype of lung adenocarcinoma. In another embodiment, at least 1, at least 2, at least 3, at least 4, at least 5, at least 6, at least 7, or up to 8 biomarkers are "down-regulated" in a specific subtype of lung adenocarcinoma.

In one embodiment, the expression level of an "up-regulated" biomarker of Table 1 as provided herein is increased by about 0.5-fold, about 1-fold, about 1.5-fold, about 2-fold, about 2.5-fold, about 3-fold, about 3.5-fold, about 4-fold, about 4.5-fold, about 5-fold, and any values in between. In another embodiment, the expression level of a "down-regulated" biomarker of Table 1 as provided herein is decreased by about 0.8-fold, about 1.4-fold, about 2-fold, about 2.6-fold, about 3.2-fold, about 3.6-fold, about 4-fold, and any values in between.

In one embodiment, the methods of the invention require the detection of at least 1, 2, 3, 4, 5, 6, 7 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79 or 80 classifier biomarkers of Table 3 in a lung cancer cell sample (e.g., lung SQ cancer sample) obtained from a patient in order to identify a basal, classical, secretory or primitive lung squamous cell carcinoma subtype.

In another embodiment, the methods of the invention require the detection of a total of at least 20, at least 40, at least 60 or up to 80 classifier biomarkers out of the 80 gene biomarkers of Table 3 in a lung cancer cell sample (e.g., lung SQ cancer sample) obtained from a patient in order to identify a basal, classical, secretory or primitive lung squamous cell carcinoma subtype.

In one embodiment, at least 1, at least 2, at least 3, at least 4, at least 5, at least 6, at least 7, at least 8, at least 9 or up to 10 biomarkers of Table 3 are "up-regulated" in a specific subtype of lung squamous cell carcinoma. In another embodiment, at least 1, at least 2, at least 3, at least 4, at least 5, at least 6, at least 7, at least 8, at least 9 or up to 10 biomarkers are "down-regulated" in a specific subtype of lung squamous cell carcinoma.

In one embodiment, the expression level of an "up-regulated" biomarker of Table 3 as provided herein is increased by about 0.5-fold, about 1-fold, about 1.5-fold, about 2-fold, about 2.5-fold, about 3-fold, about 3.5-fold, about 4-fold, about 4.5-fold, about 5-fold, and any values in between. In another embodiment, the expression level of a "down-regulated" biomarker of Table 3 as provided herein is decreased by about 0.8-fold, about 1.4-fold, about 2-fold, about 2.6-fold, about 3.2-fold, about 3.6-fold, about 4-fold, and any values in between.

It is recognized that additional genes or proteins can be used in the practice of the invention. In general, genes useful in classifying the subtypes of lung squamous cell carcinoma and/or lung adenocarcinoma, include those that are independently capable of distinguishing between normal versus tumor, or between different classes or grades of lung cancer. A gene is considered to be capable of reliably distinguishing between subtypes if the area under the receiver operator characteristic (ROC) curve is approximately 1.

In some embodiments, one or more kits for practicing the methods of the invention are further provided. The kit can encompass any manufacture (e.g., a package or a container) including at least one reagent, e.g., an antibody, a nucleic acid probe or primer, and/or the like, for detecting the biomarker level of a classifier biomarker. The kit can be promoted, distributed, or sold as a unit for performing the methods of the present invention. Additionally, the kits can contain a package insert describing the kit and methods for its use.

In one embodiment, a method is provided herein for determining a disease outcome or prognosis for a patient suffering from cancer. In some cases, the cancer is lung cancer. The disease outcome or prognosis can be measured by examining the overall survival for a period of time or intervals (e.g., 0 to 36 months or 0 to 60 months). In one embodiment, survival is analyzed as a function of subtype (e.g., for lung cancer, adenocarcinoma (TRU, PI, and PP), or squamous (primitive, classical, secretory, basal). Relapse-free and overall survival can be assessed using standard Kaplan-Meier plots as well as Cox proportional hazards modeling.

In one embodiment, upon determining a patient's lung cancer subtype, the patient is selected for suitable therapy, for example PARP inhibitor treatment. In one embodiment, upon determining a patient's lung cancer subtype, the patient is administered a suitable therapeutic agent, for example, a PARP inhibitor. Each lung cancer AD or SQ subtype may show a differential response to PARP inhibitor treatment. In some cases, the suitable therapy can further comprise using one or more chemotherapeutic agents in addition to or in combination with the PARP inhibitor treatment.

The methods provided herein are also useful for determining whether a subject is likely to respond to one or more of the PARP inhibitors provided herein and known in the art. In one embodiment, the method comprises determining a subtype of a lung cancer AD or SQ sample and subsequently determining a level of activation of homologous recombination (HR) and/or DNA damage pathways of said sub-type. In one embodiment, the subtype is determined by determining the expression levels of one or more classifier biomarkers using sequencing (e.g., RNASeq), amplification (e.g., qRT-PCR) or hybridization assays (e.g., microarray analysis) as described herein. The one or more biomarkers can be selected from a publically available database (e.g., TCGA lung AD and SQ RNASeq gene expression datasets or any other publically available AD or SQ gene expression datasets provided herein). In some embodiments, the biomarkers of Table 1 can be used to specifically determine the subtype of an AD lung sample obtained from a patient. In some embodiments, the biomarkers of Table 3 can be used to specifically determine the subtype of a SQ lung sample obtained from a patient. The level of activation of HR and/or DNA damage pathways can be ascertained by determining the expression of one or a plurality of genes from said HR and/or DNA damage repair pathways. In one embodiment, the level of homologous recombination and DNA damage gene expression is determined by measuring gene expression signatures of DNA damage genes and genes involved in homologous recombination. (HR). The HR and DNA damage markers can be measured in the same and/or different sample used to subtype the lung cancer sample as described herein. The HR and DNA damage genes can be any such genes known in the art or provided herein.

A change in expression of one or a plurality of HR and/or DNA damage related genes can be indicative of the state or level of activation of HR related and/or DNA damage repair pathways in a subject. The change in expression can be a change in the expression level or abundance of the one or plurality of HR and/or DNA damage repair related genes. In some cases, the lowering of the expression level or abundance of the one or plurality of HR/DNA damage repair related genes can affect the subsequent activity level or functioning of the one or plurality of HR/DNA damage repair related genes. In some cases, a reduction in or lowering of the expression of one or a plurality of HR/DNA damage repair related genes in a subject may indicate that one or more of said subject's HR/DNA damage repair related pathways has a reduced level of activity or function or is HR-deficient or DNA damage repair deficient. A subject with one or more deficient HR/DNA damage repair related pathways or with one or more HR/DNA damage repair related pathways with reduced activity or function may be indicative of said subject showing an increase likelihood for responding favorably to treatment with a PARP inhibitor. The PARP inhibitor can be any PARP inhibitor known in the art and/or provided herein.

In some cases, specific lung cancer AD subtypes can show levels of expression of one or a plurality of HR/DNA damage repair related genes that differ as compared to other lung cancer AD subtypes or a control. In some cases, specific lung cancer SQ subtypes can show levels of expression of one or a plurality of HR/DNA damage repair related genes that differ as compared to other lung cancer SQ subtypes or a control. The control can be a sample from a healthy subject or a subject that is not suffering from lung cancer. In one embodiment, the TRU subtype of AD shows reduced expression of one or a plurality of HR/DNA damage repair related genes. A subject with a TRU subtype of AD may be a candidate for PARP inhibitor treatment. In a separate embodiment, the basal or secretory subtypes of SQ show reduced expression of one or a plurality of HR/DNA damage repair related genes. A subject with a basal or secretory subtype of SQ may be a candidate for PARP inhibitor treatment.

EXAMPLES

The present invention is further illustrated by reference to the following Examples. However, it should be noted that these Examples, like the embodiments described above, are illustrative and are not to be construed as restricting the scope of the invention in any way.

Example 1—Differences in Homologous Recombination Gene Expression Across Lung Adenocarcinoma and Squamous Cell Carcinoma Gene Expression Subtypes Suggesting Potential for Differential Response to PARP Inhibitors Introduction Gene expression-based subtyping in lung Adenocarcinoma (AD) and lung Squamous Cell Carcinoma (SQ) classifies AD and SQ tumors into distinct subtypes with variable expression of underlying biology and DNA damage response genes potentially impacting response to therapeutics including PARP inhibitors. These subtypes are linked to differences in chemotherapy sensitivity, and may impact response to therapeutics like PARP inhibitors.

Methods

Using the TCCA lung cancer gene expression datasets (AD n=515, and SQ n=501; Table 5), AD subtypes (Terminal Respiratory Unit (TRU), Proximal Proliferative (PP), and Proximal Inflammatory (PI)) and SQ subtypes (Primitive, Classical, Secretory, and Basal) were defined using gene expression signatures. To determine AD subtype (TRU, PP, and PI), the published 506-gene nearest centroid classifier as described previously in Wilkerson et al [1] was used. To determine the SQ subtype (basal, classical, primitive, secretory), the published 208-gene nearest centroid classifier as described previously in Wilkerson et al [2] was used. After median centering of genes in the signature, each sample was assigned the subtype corresponding to the centroid with which it was maximally correlated. (Pearson). Association between AD and SQ gene expression subtypes and the expression of 15 recognized homologous recombination (HR) related genes ATM, ATR, BRCA1, BRCA2, BRIP1 (FANCJ), CDK12, CHEK1, CHEK2, FANCA FANCI, FANCD2, MRE11A, RAD51L1 (RAD51B), RAD51C, and PTEN was examined using linear regression models. Association tests included adjustment for 3 published BRCAness/PARP inhibitor response signatures developed in ovarian and/or breast cancer (Konstantinopoulos et al. PMID 20547991, Daemen et al, PMID 22875744 and McGrail et al, PMID 28649435) and a proliferation score.

TABLE 5

TCGA lung AD and SQ datasets

TCGAAD

| | |
|---|---|
| Total # of samples | 515 |
| GeneCentric Subtype | |
| TRU (Bronchioid) | 196 |
| PP (Magnoid) | 134 |
| PI (Squamoid) | 185 |
| Stage | |
| StageI | 276 |
| StageII | 123 |
| StageIII | 84 |
| StageIV | 27 |
| StageNA | 5 |

TCGA SQ

| | |
|---|---|
| Total # of samples | 501 |
| GeneCentric Subtype | |
| Basal | 149 |
| Classical | 178 |
| Primitive | 70 |
| Secretory | 104 |
| Stage | |
| StageI | 241 |
| StageII | 152 |
| StageIII | 85 |
| Stage IV | 7 |
| Stage NA | 16 |

Results

Figure 2:
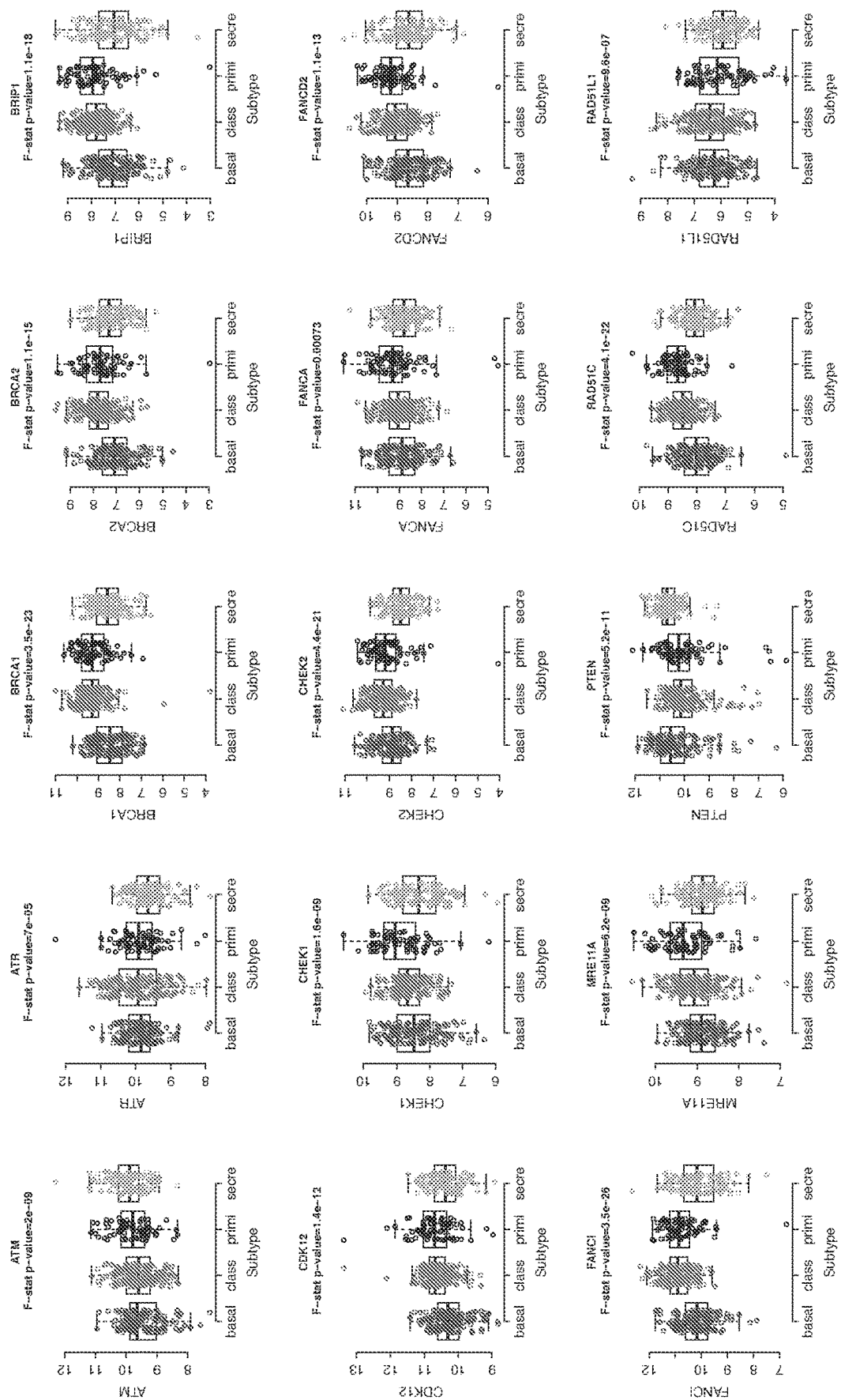
FIG. 2 illustrates marked differences in gene expression patterns of 15 recognized HR-related genes for SQ subtypes. SQ subtyping was performed using the 208 gene gold standard sub-typer described in Example 1.
Figure 3:
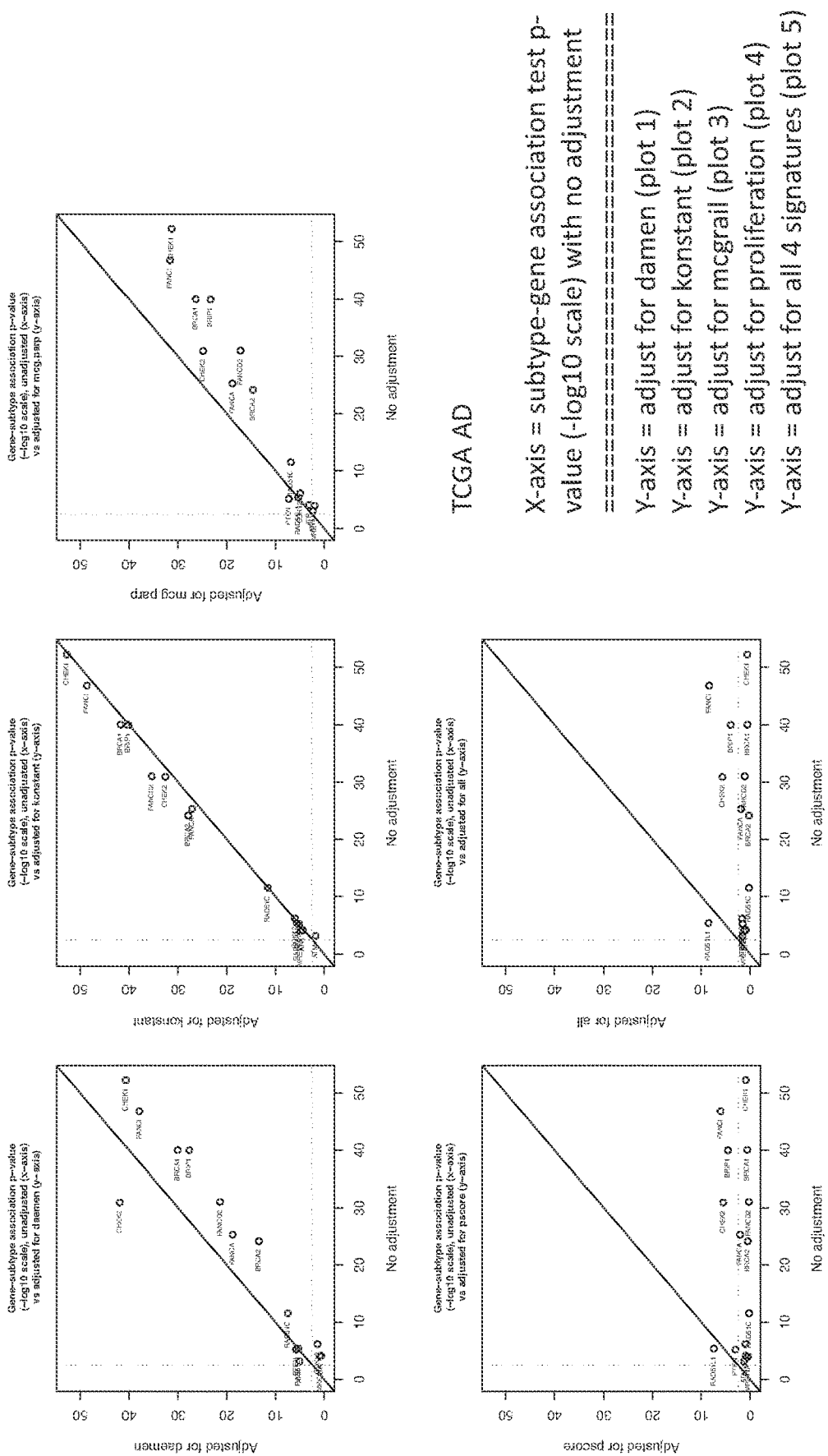
FIG. 3 illustrates subtype-gene association tests with and without adjustment for the TCGA AD dataset.
Figure 4:
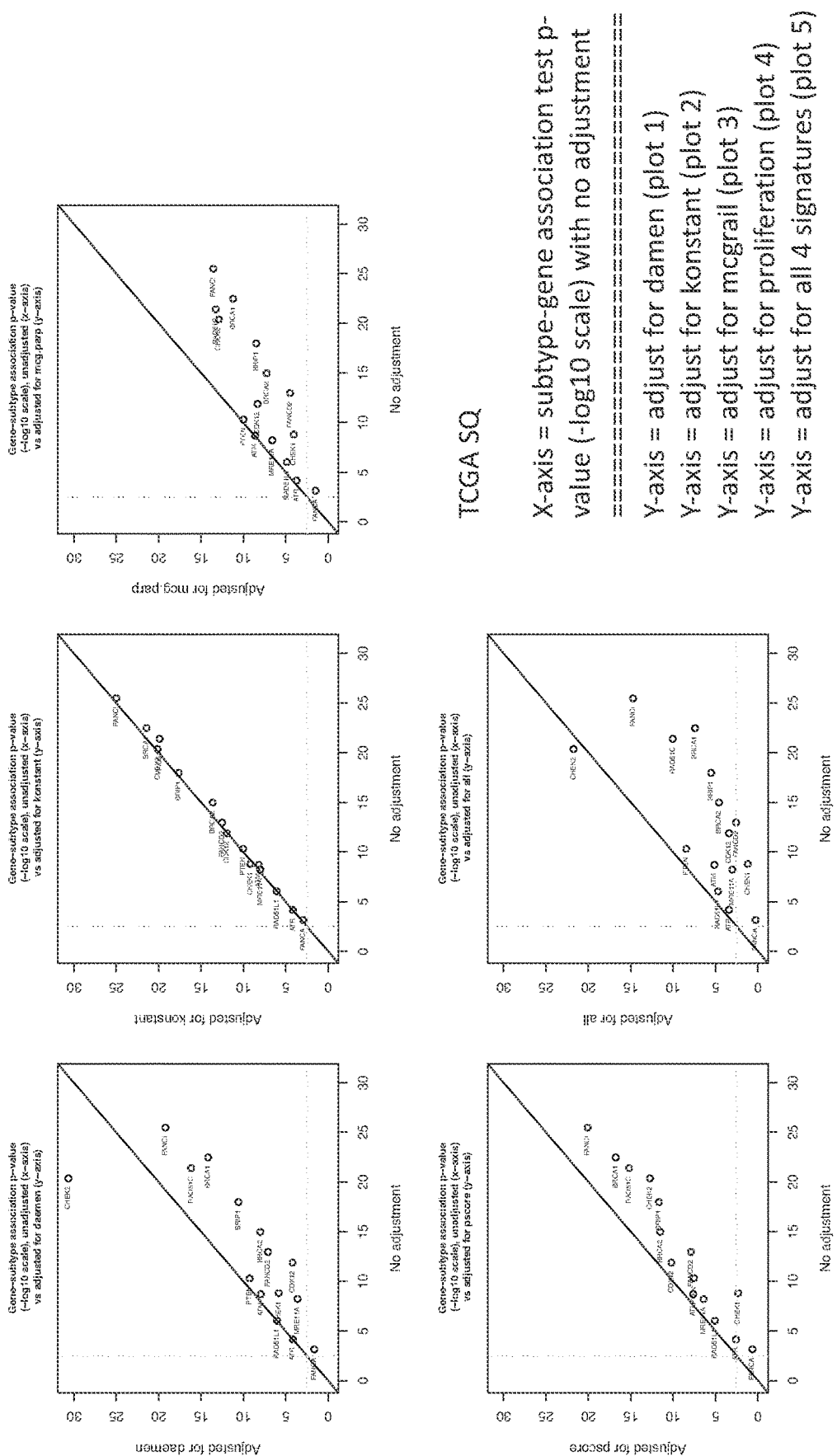
FIG. 4 illustrates subtype-gene association tests with and without adjustment for the TCGA SQ dataset.
Figure 5:
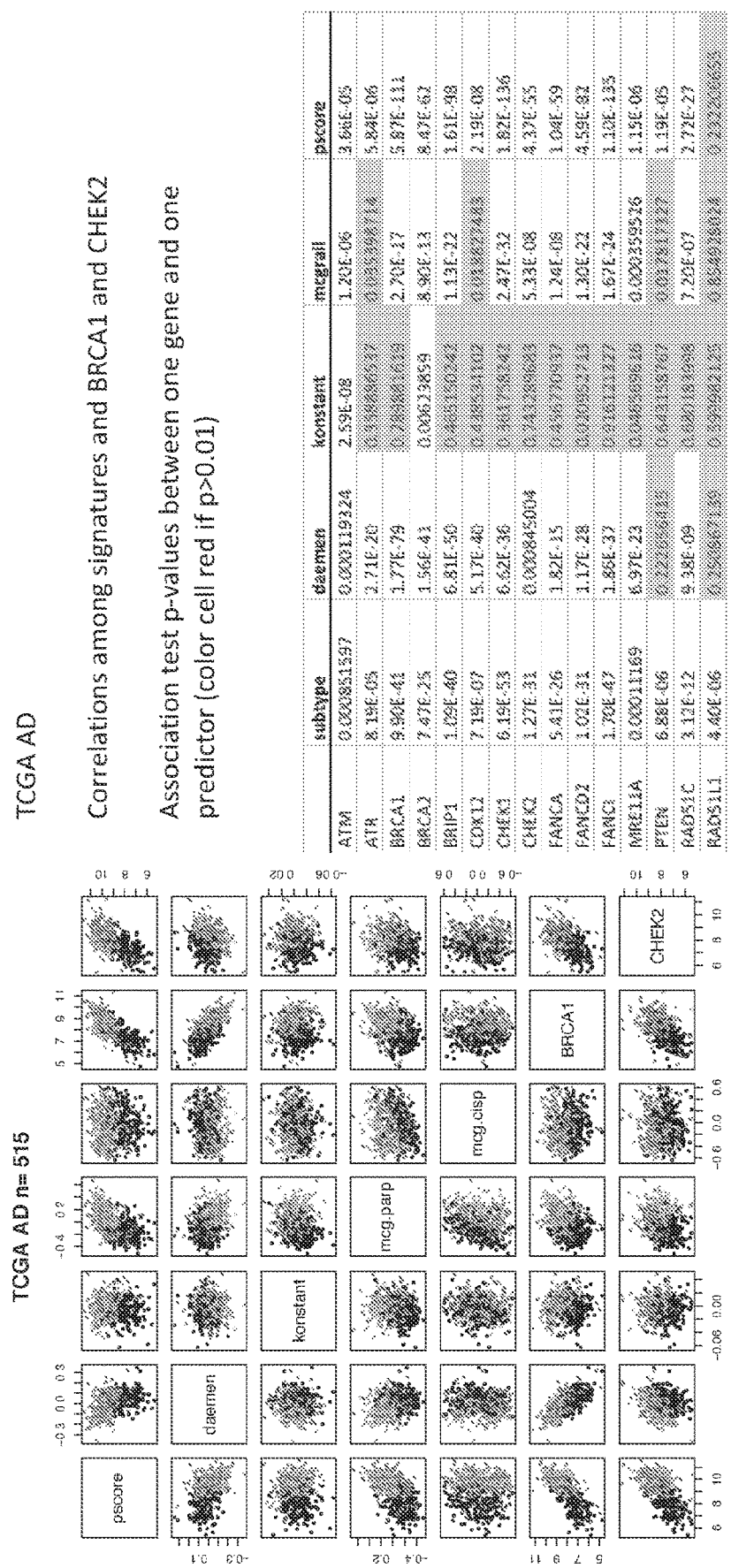
FIG. 5 illustrates correlations among signatures and BRCA1 and CHEK2 for the TCGA AD dataset.
Figure 6:
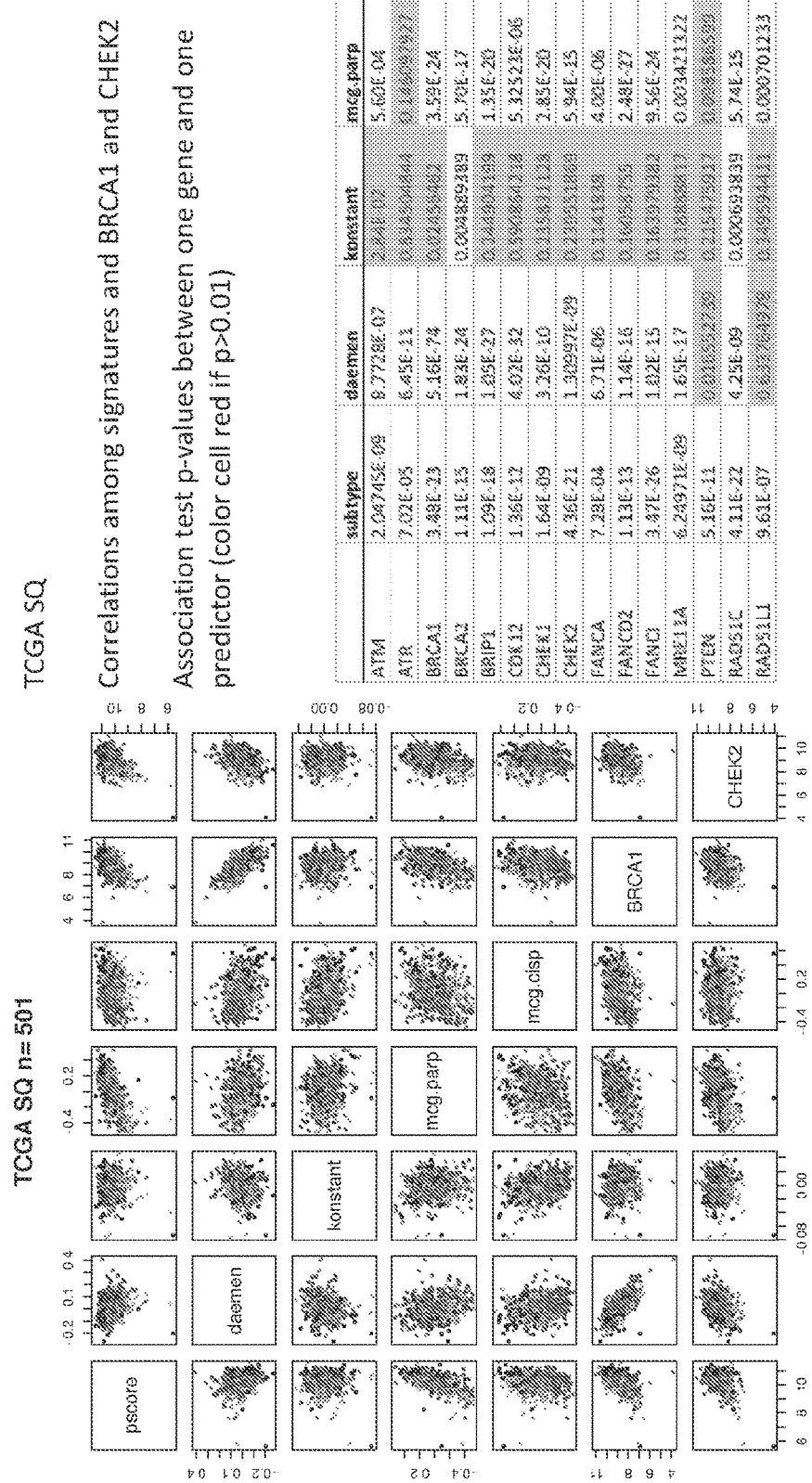
FIG. 6 illustrates correlations among signatures and BRCA1 and CHEK2 for the TCGA SQ dataset.
Figure 7:
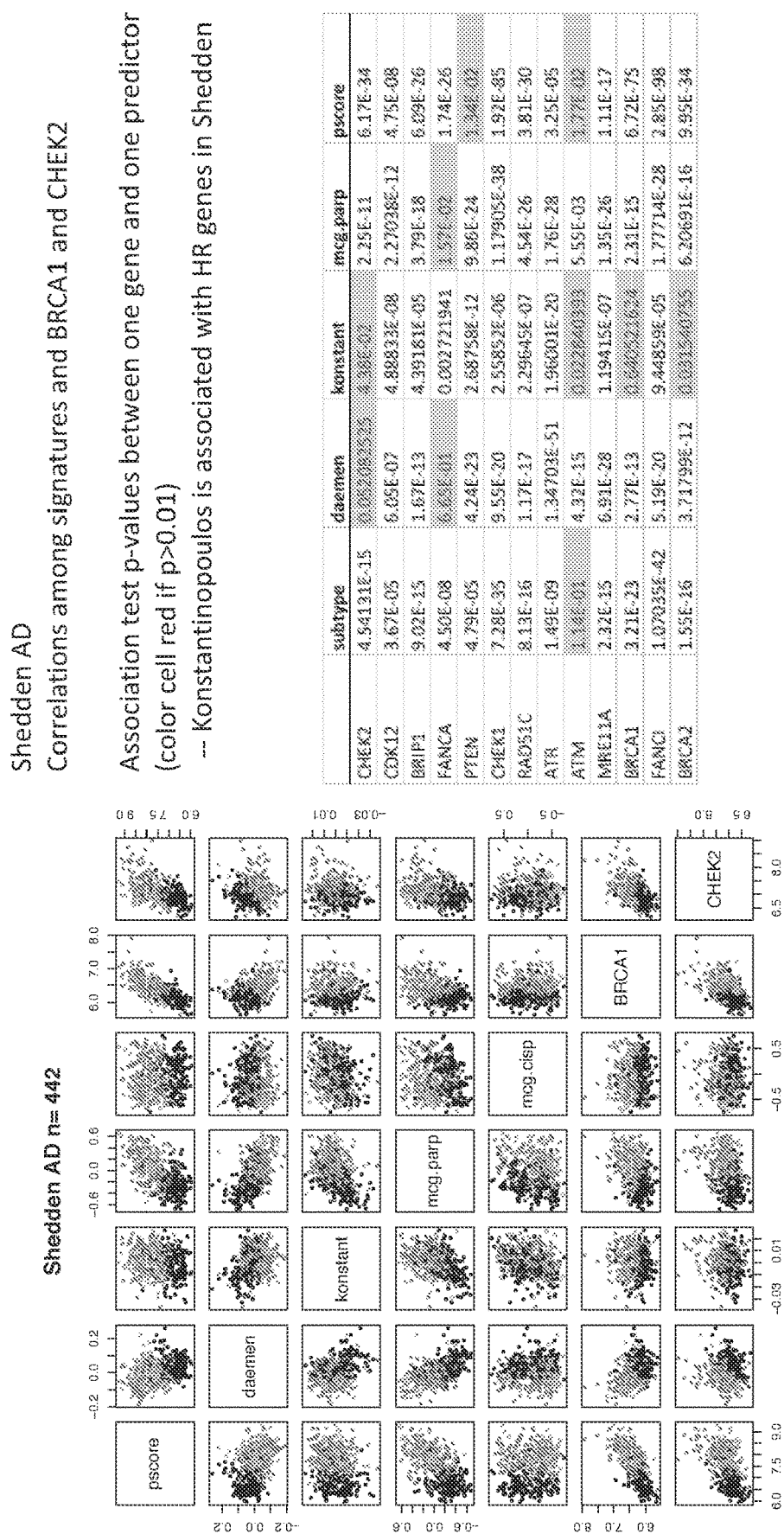
FIG. 7 illustrates correlations among signatures and BRCA1 and CHEK2 for the Shedden AD dataset.

AD and SQ subtypes showed strong association with the 15 HR genes (max and median F-test p-values were 8.5e-04 and 7.5e-25 in AD, and 7.3e-04 and 1.4e-12 in SQ: FIGS. 1 and 2). The TRU subtype in AD showed low expression relative to the other AD subtypes for a majority of the HR genes, including BRCA1 and CHEK2 (FIG. 1). In SQ, the same was true for basal and secretory subtypes (FIG. 2). Simultaneous adjustment for 3 published BRCAness/PARP inhibitor response signatures as well as proliferation reduced the association strength between subtype and HR gene expression in AD and less so in SQ (see FIGS. 3-6). In AD, association between subtype and gene expression remained significant for 4 HR genes (using Bonferroni correction for 15 tests), including CHEK2, FANCI, BRIP1, and RAD51L1 (RAD51B) (FIGS. 3 and 5). In SQ, association between subtype and gene expression remained significant for all except 2 HR genes, CHEK1 and FANCA, (median and min Bonferroni-adjusted p-value 2.9e-04 and 2.6e-21) (FIGS. 4 and 6).

CONCLUSIONS

Intrinsic biologic subtypes of lung AD and SQ reveal differential expression of several HR-related genes.

REFERENCES

1.) Wilkerson M D, et al. PLoS One 2012; 7(5): e36530. PMID 22590557
2.) Wilkerson M D, et al. Clin Cancer Res 2010; 16(19): 4864-75. PMID 20643781

Figure 8:
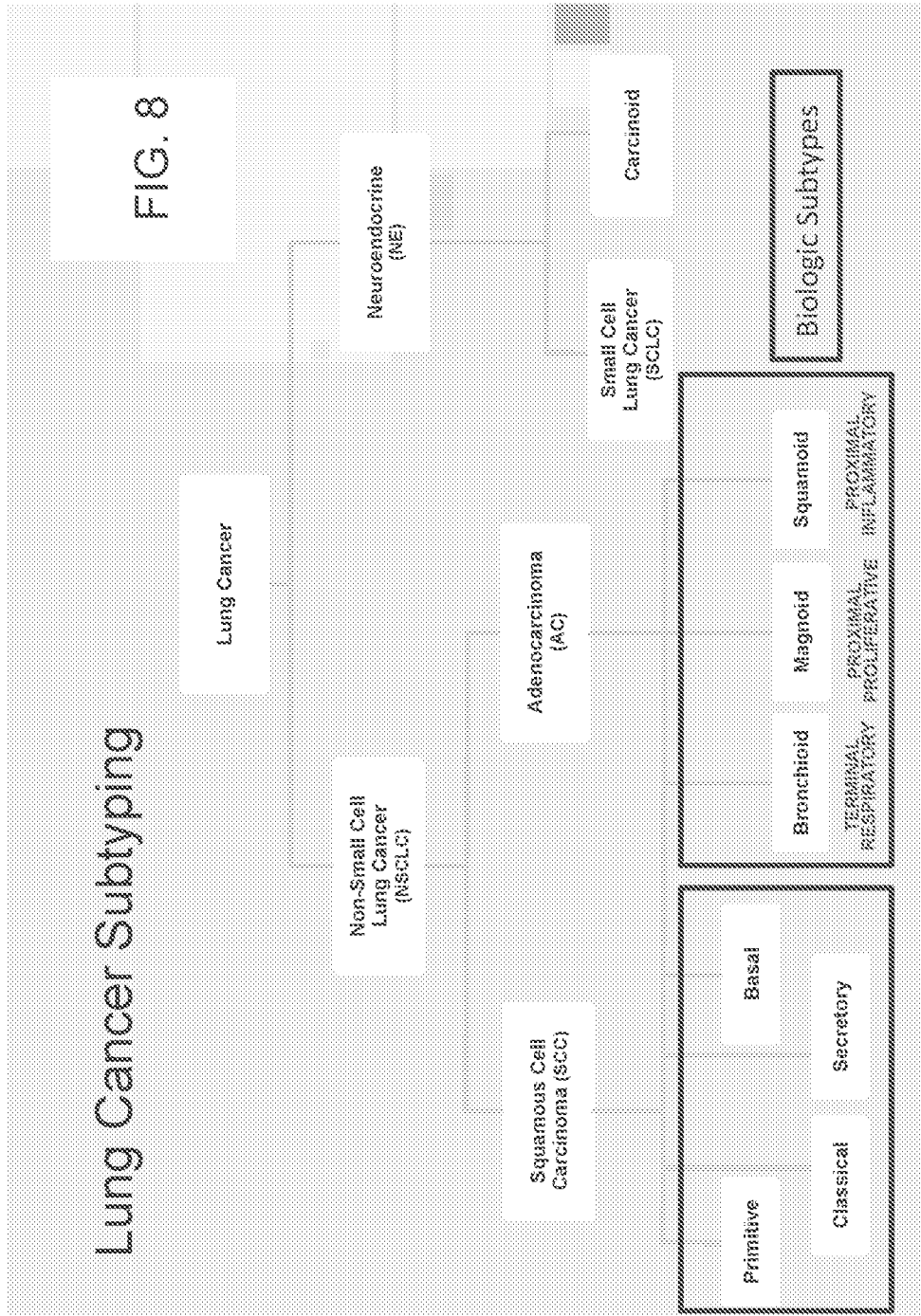
FIG. 8 illustrates lung cancer subtyping and the biologic subtypes of squamous cell carcinoma (SCC or SQ) and Adenocarcinoma (AC or AD).

Example 2—Differences in Homologous Recombination Gene Expression Across Lung Adenocarcinoma and Squamous Cell Carcinoma Gene Expression Subtypes Suggesting Potential for Differential Response to PARP Inhibitors-Use of Table 1 Classifier Biomarkers for Lung AD Subtyping and Table 3 Classifier Biomarkers for Lung SQ Subtyping Introduction Gene expression based subtyping has consistently identified 3 distinct biologic subtypes in Lung Adenocarcinoma (AD), Terminal Respiratory Unit (TRU) formerly Bronchioid, Proximal Proliferative (PP) formerly Magnoid, and Proximal Inflammatory (PI) formerly Squamoid1, 2 and 4 subtypes within lung SQ, Primitive, Classical, Basal and Secretory[3,4] (See FIG. 8). AD and SQ subtypes demonstrate key differences in genomic alterations, tumor drivers, prognosis, and likely response to various therapies.[1-4]

Methods

Figure 13:
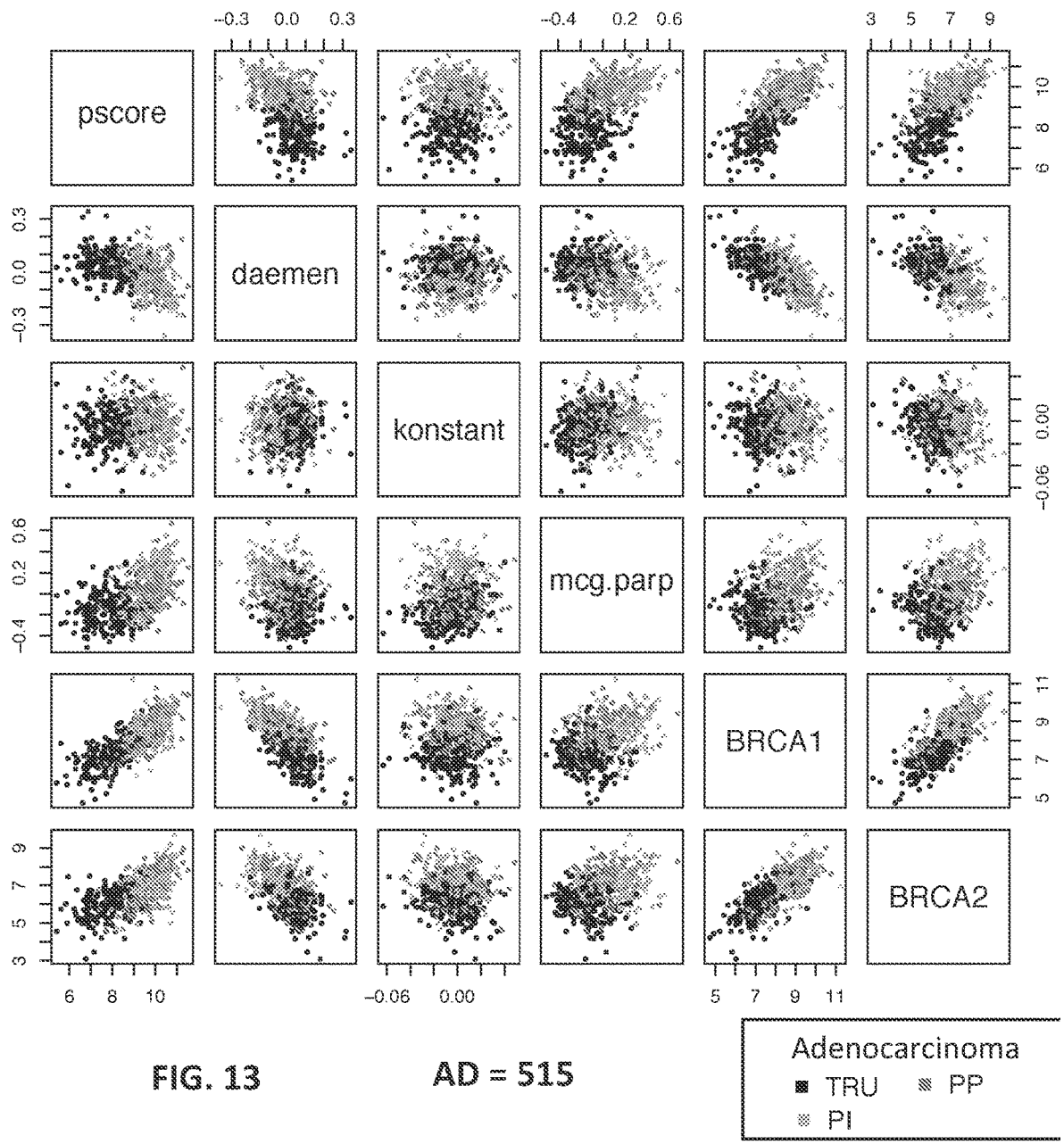
FIG. 13 illustrates scatterplots of proliferation (pscore), BRCAness/PARP inhibitor signatures, BRCA1, and BRCA2 for AD subtypes.
Figure 14:
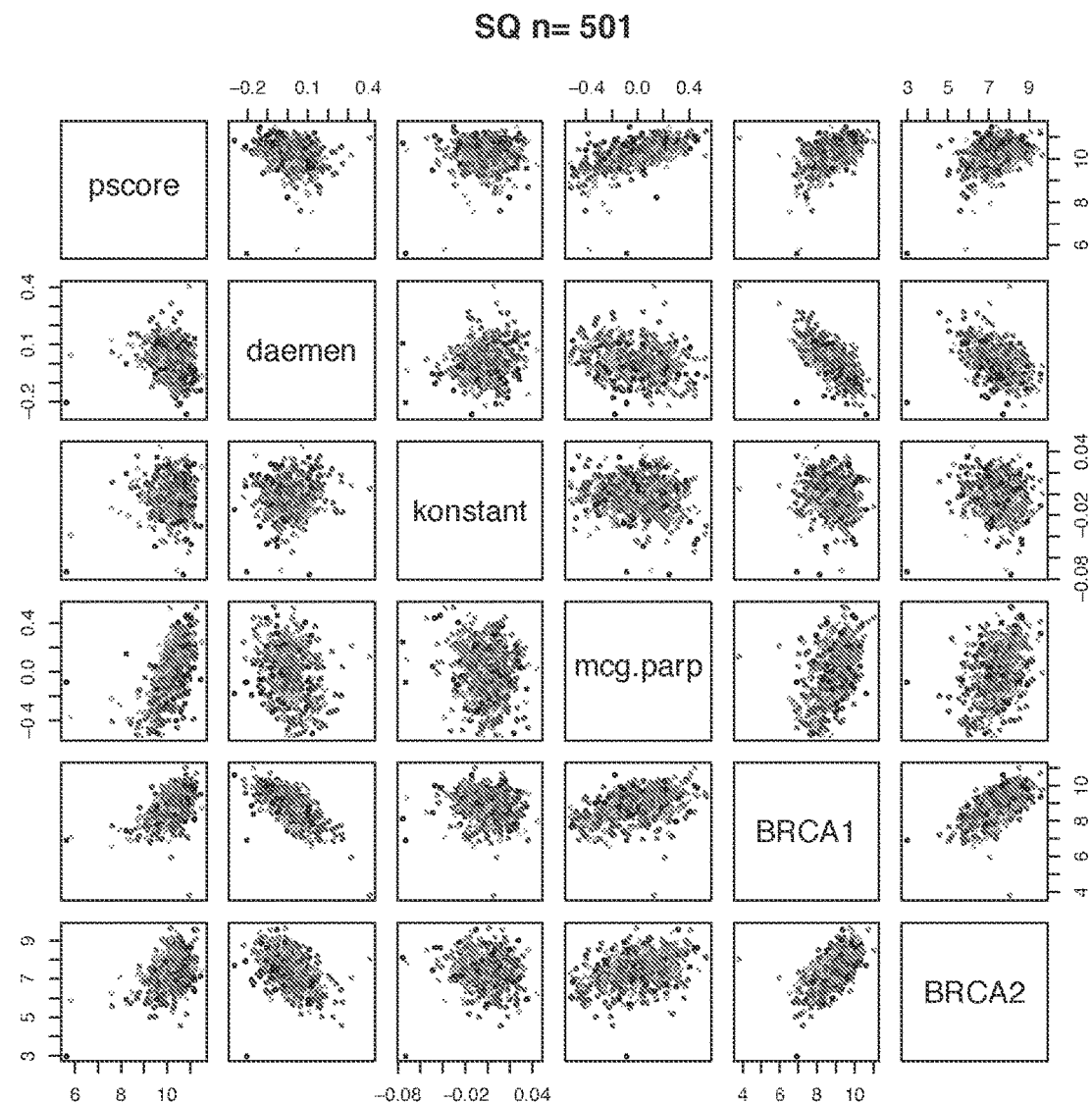
FIG. 14 illustrates scatterplots of proliferation (pscore), BRCAness/PARP inhibitor signatures, BRCA1, and BRCA2 for SQ subtypes.

Using the TCGA lung cancer gene expression datasets (AD n=515, and SQ n=501; Table 5), AD subtypes (Terminal Respiratory Unit (TRU), Proximal Proliferative (PP), and Proximal Inflammatory (PI)) and SQ subtypes (Primitive, Classical, Secretory, and Basal) were defined using gene expression signatures. To determine AD subtype (TRU, PP, and PI), the 48 gene classifier of Table 1 was used. To determine SQ subtype (Primitive, Classical, Secretory, and Basal), the 80 gene classifier of Table 3 was used. Association between subtype and BRCAness/PARP inhibitor response signatures was evaluated separately in AD and SQ using linear regression. Correlations between proliferation,[5] BRCA1, BRCA2, and research versions of 3 published BRCAness/PARP inhibitor response signatures developed in ovarian and/or breast cancer (Konstantinopoulos et al.[6], Daemen et al.[7], and McGrail et al.[8]) were analyzed using scatterplots (see FIGS. 13 and 14). Expression patterns of 15 recognized homologous recombination (HR) related genes (ATM, ATR, BRCA1, BRCA2, BRIP1, CDK12, CHEK1, CHEK2, FANCA, FANCI, FANCD2, MRE11A, RAD51L1, RAD51C, PTEN) among AD and SQ subtypes were examined using heatmaps. Association between subtype and HR gene expression was evaluated using linear regression, with and without adjustment for proliferation and BRCAness/PARP inhibitor response signatures (Tables 6-8).

Results

Figure 9:
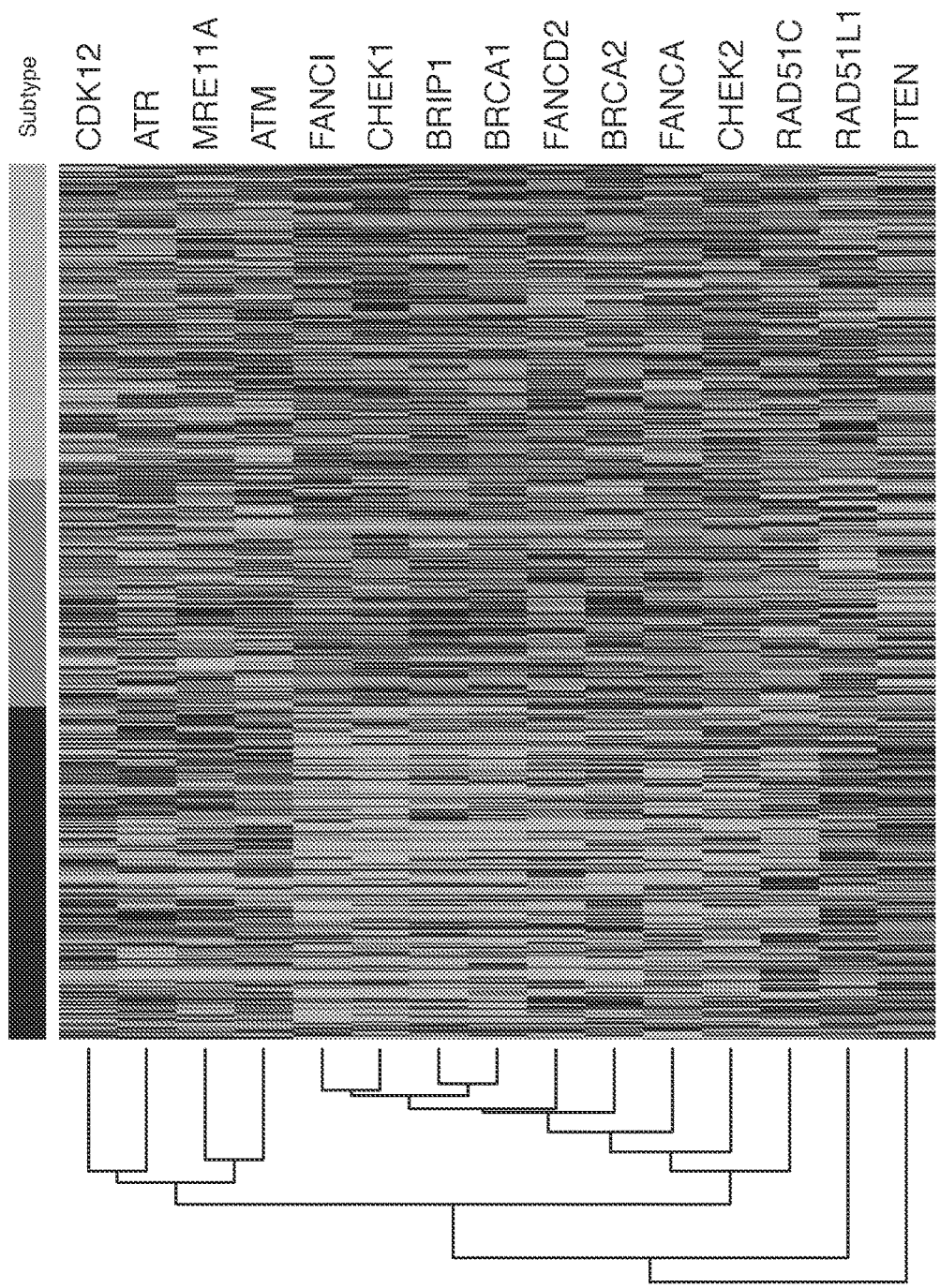
FIG. 9 illustrates marked differences in gene expression patterns of 15 recognized HR-related genes for AD subtypes. AD subtyping was performed using the classifiers shown in Table 1.
Figure 10:
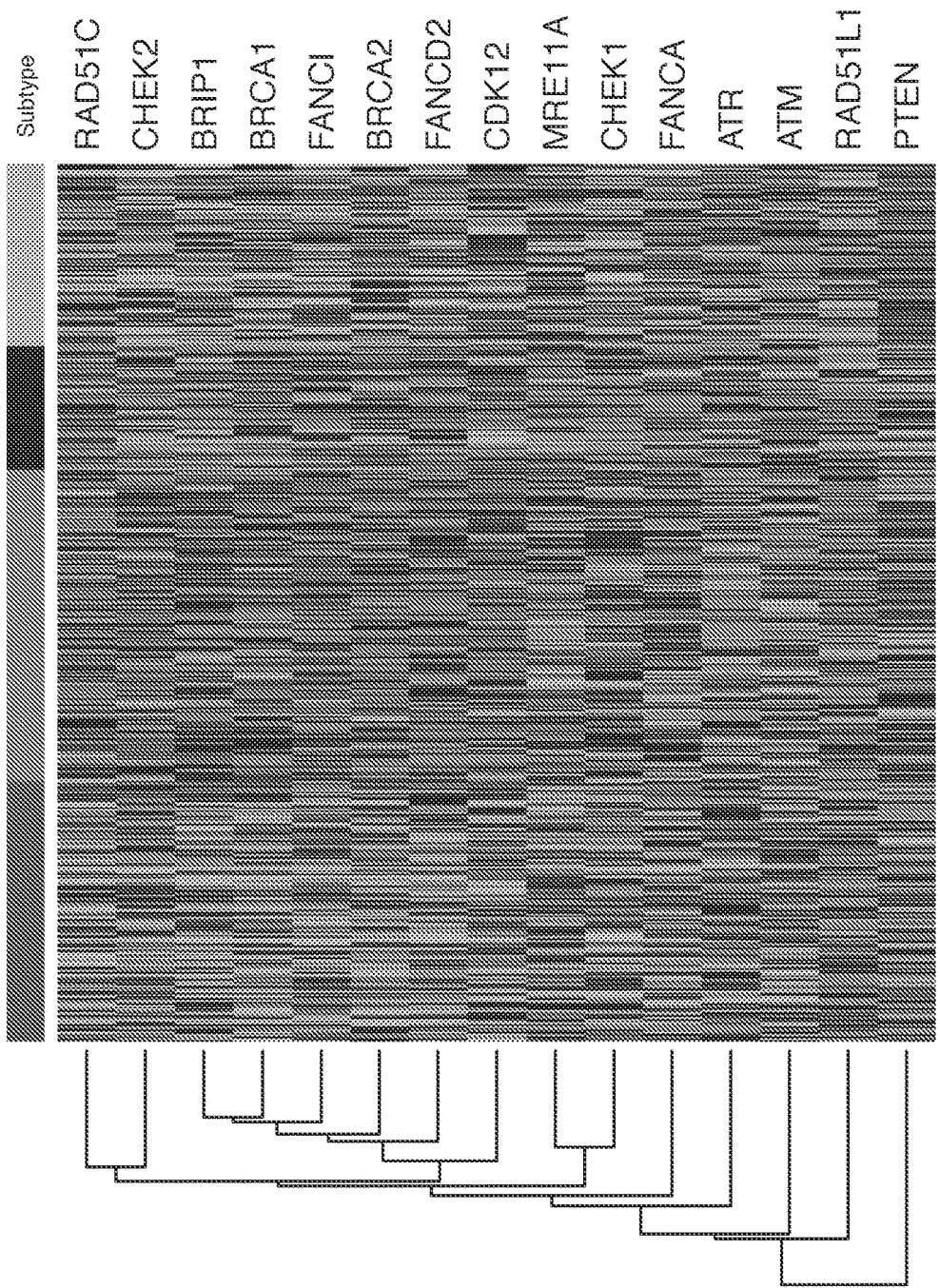
FIG. 10 illustrates marked differences in gene expression patterns of 15 recognized HR-related genes for SQ subtypes. SQ subtyping was performed using the classifiers shown in Table 3.
Figure 11:
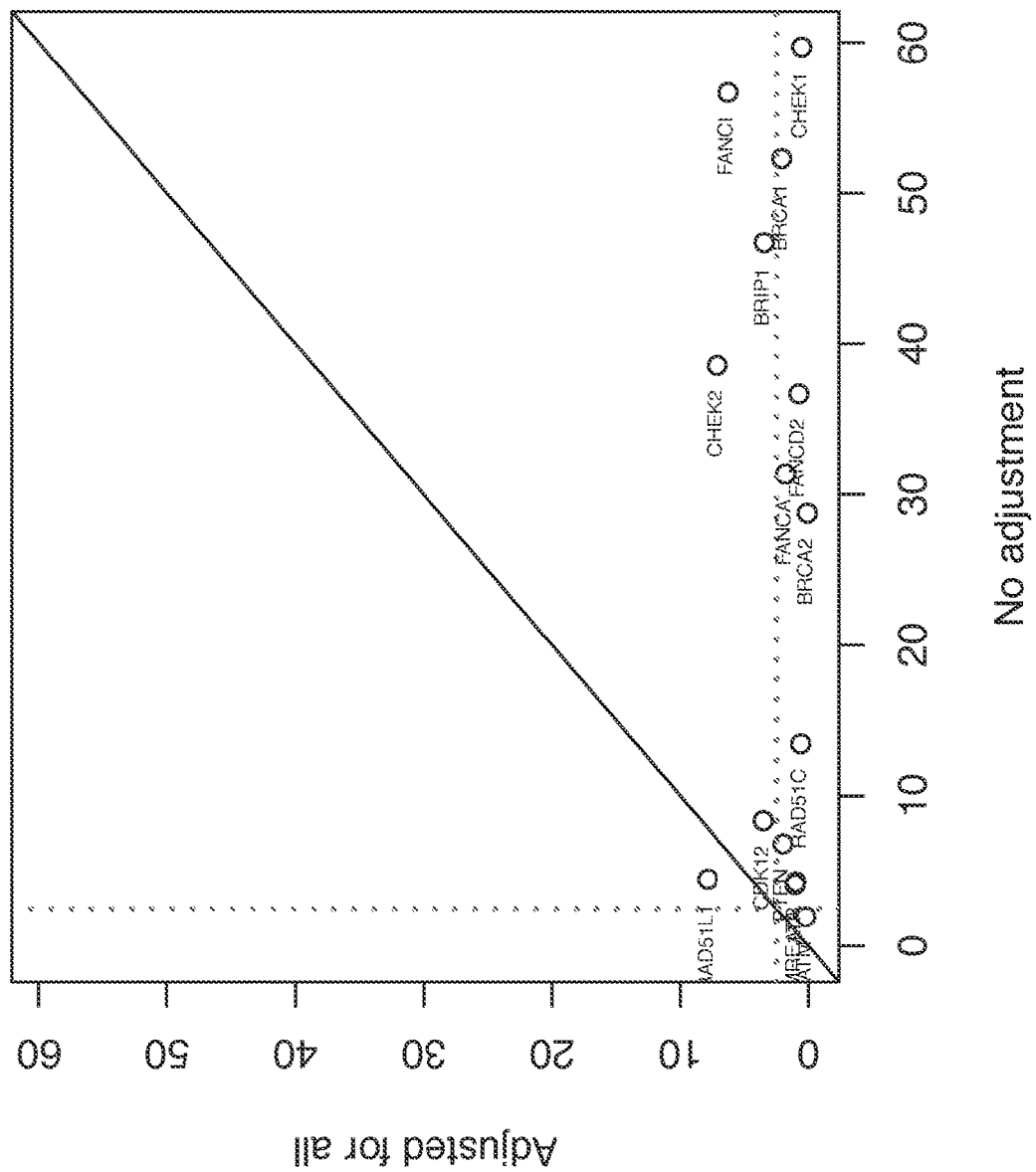
FIG. 11 illustrates AD subtype-HR gene association test p-values (−log 10 scale) without adjustment (x-axis) and with adjustment for 3 BRCAness/PARP inhibitor signatures and proliferation (y-axis). Dotted red lines shows bonferroni threshold for 15 tests and alpha=0.05.
Figure 12:
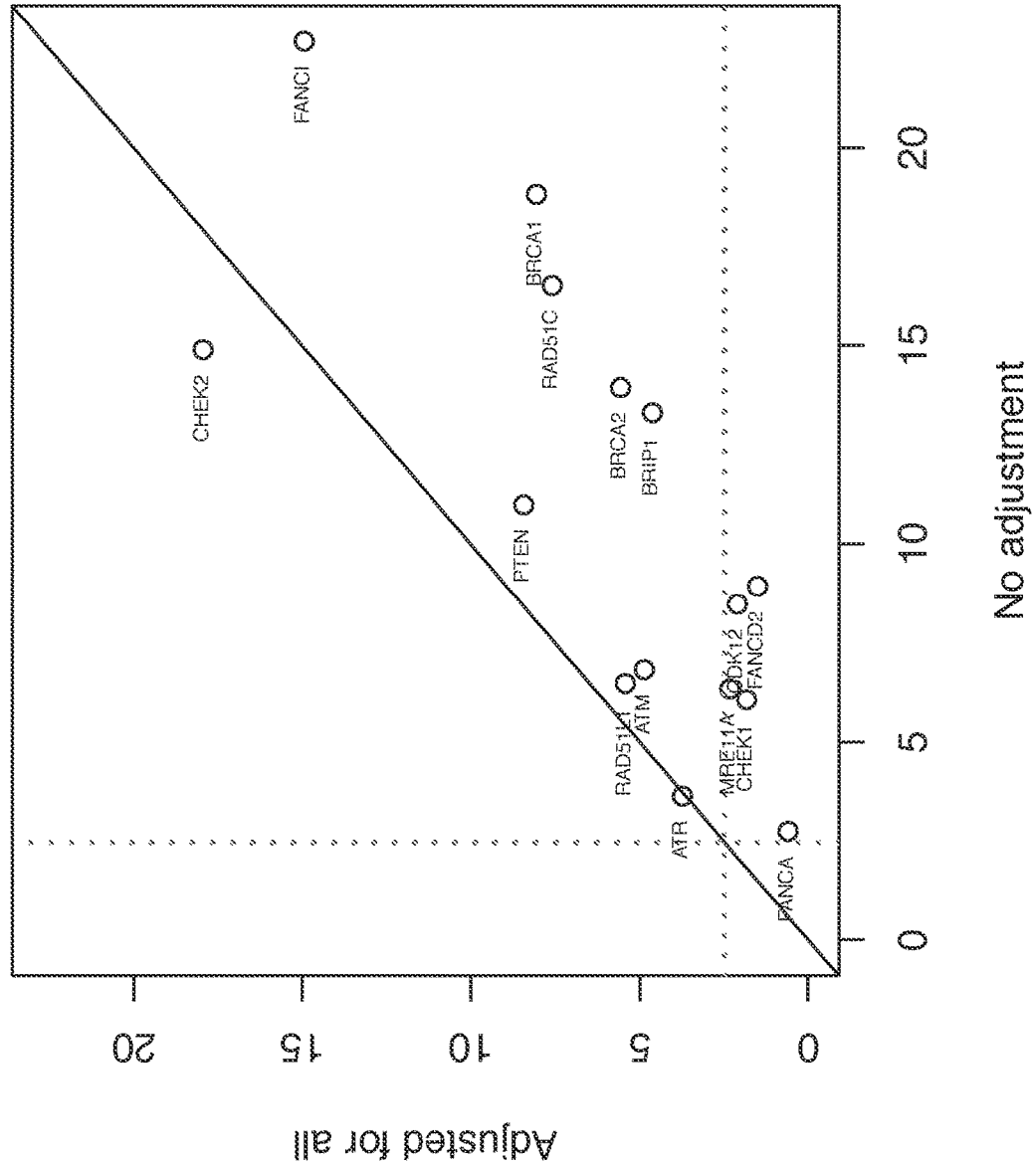
FIG. 12 illustrates SQ subtype-HR gene association test p-values (−log 10 scale) without adjustment (x-axis) and with adjustment for 3 BRCAness/PARP inhibitor signatures and proliferation (y-axis). Dotted red lines shows bonferroni threshold for 15 tests and alpha=0.05.

AD and SQ subtypes showed strong association with the 15 HR genes (see FIGS. 9 and 10). The TRU subtype in AD showed low expression relative to the other AD subtypes for a majority of the HR genes, including BRCA1 and CHEK2. In SQ, the same was true for basal and secretory subtypes. Simultaneous adjustment for 3 published BRCAness/PARP inhibitor response signatures as well as proliferation reduced the association strength between subtype and HR gene expression in AD and less so in SQ (see FIGS. 11-14). In AD, association between subtype and gene expression remained significant for 5 HR genes (using Bonferroni correction for 15 tests), including CHEK2, FANCI, BRIP1, and RAD51L1 (RAD51B) (see FIGS. 11 and 13). In SQ, association between subtype and gene expression remained significant for all except 5 HR genes, CHEK1 and FANCA, (see FIGS. 12 and 14).

TABLE 6

Association test p values of BRCAness/PARP inhibitor signatures and proliferation in AD and SQ gene expression subtypes

|  | AD n = 515 | SQ n = 501 |
| --- | --- | --- |
| daemen | 1.06E−13 | 8.17E−11 |
| konstant | 0.022172835 | 5.23E−06 |
| mcg.parp | 9.60E−31 | 5.40E−14 |
| pscore | 8.47E−89 | 4.93E−06 |

TABLE 7

Association test p-values between homologous recombination (HR) genes and subtype, BRCAness/PARP inhibitor signatures, and proliferation (pscore) in AD (n = 515).

|  | subtype | daemen | konstant | mcg.parp | pscore |
| --- | --- | --- | --- | --- | --- |
| ATM | 0.01152349 | 0.000119324 | 2.59E−08 | 1.20E−06 | 3.66E−05 |
| ATR | 5.44E−05 | 2.71E−20 | 0.358886537 | 0.035398714 | 5.84E−06 |
| BRCA1 | 5.62E−53 | 1.77E−79 | 0.789881619 | 2.70E−17 | 5.87E−111 |
| BRCA2 | 1.84E−29 | 1.56E−41 | 0.00623859 | 8.90E−13 | 8.47E−62 |
| BRIP1 | 2.05E−47 | 6.81E−50 | 0.465150242 | 1.13E−22 | 1.61E−98 |
| CDK12 | 4.61E−09 | 5.17E−40 | 0.438534102 | 0.018827483 | 2.19E−08 |
| CHEK1 | 2.09E−60 | 6.62E−36 | 0.361758242 | 2.47E−32 | 1.82E−136 |
| CHEK2 | 3.01E−39 | 0.000845004 | 0.743289683 | 5.33E−08 | 4.37E−55 |
| FANCA | 4.76E−32 | 1.82E−15 | 0.456770937 | 1.24E−08 | 1.04E−59 |
| FANCD2 | 2.32E−37 | 1.17E−28 | 0.020952713 | 1.30E−22 | 4.59E−82 |
| FANCI | 2.20E−57 | 1.86E−37 | 0.916121327 | 1.67E−24 | 1.10E−135 |
| MRE11A | 7.97747E−05 | 6.97E−23 | 0.046569616 | 0.000359526 | 1.15E−06 |
| PTEN | 1.64E−07 | 0.222656415 | 0.643158767 | 0.017817327 | 1.19E−05 |
| RAD51C | 3.91E−14 | 9.38E−09 | 0.680183998 | 7.20E−07 | 2.72E−27 |
| RAD51L1 | 3.57E−05 | 0.250867139 | 0.599982125 | 0.854928024 | 0.232206655 |

TABLE 8

Association test p-values between homologous recombination (HR) genes and subtype, BRCAness/PARP inhibitor signatures, and proliferation (pscore) in SQ (n = 501).

|  | subtype | daemen | konstant | mcg.parp | pscore |
| --- | --- | --- | --- | --- | --- |
| ATM | 1.52E−07 | 8.77E−07 | 0.028359508 | 0.000560081 | 3.02E−08 |
| ATR | 0.000235452 | 6.45E−11 | 0.834504844 | 0.146097927 | 0.000167912 |
| BRCA1 | 1.52E−19 | 5.16E−74 | 0.02456462 | 3.59E−24 | 1.19E−33 |
| BRCA2 | 1.15E−14 | 1.83E−24 | 0.004889389 | 5.70E−17 | 3.55E−24 |
| BRIP1 | 4.97E−14 | 1.05E−27 | 0.244904199 | 1.35E−20 | 1.11E−45 |
| CDK12 | 3.73E−09 | 4.02E−32 | 0.590864218 | 5.33E−06 | 0.000575991 |
| CHEK1 | 8.73E−07 | 3.26E−10 | 0.235831128 | 2.85E−20 | 4.32E−54 |
| CHEK2 | 1.29E−15 | 1.31E−09 | 0.239551869 | 5.94E−15 | 6.19E−34 |
| FANCA | 0.001800972 | 6.71E−06 | 0.1141838 | 4.00E−06 | 1.53E−32 |
| FANCD2 | 1.18E−09 | 1.14E−16 | 0.16058755 | 2.48E−27 | 5.38E−54 |
| FANCI | 2.06E−23 | 1.02E−15 | 0.163979382 | 9.56E−24 | 7.57E−59 |
| MRE11A | 4.66E−07 | 1.65E−17 | 0.318888817 | 0.003421322 | 0.000187893 |
| PTEN | 1.04E−11 | 0.016552739 | 0.215475917 | 0.098586599 | 1.10E−05 |
| RAD51C | 2.97E−17 | 4.25E−09 | 0.000693839 | 5.74E−15 | 2.94E−24 |
| RAD51L1 | 3.42E−07 | 0.633764978 | 0.349594411 | 0.000701233 | 0.002547001 |

Molecular subtypes of lung AD and SQ vary in expression of several BRCAness/PARP inhibitor response signatures. Subtypes reveal differential expression of HR-related genes. Adjustment for proliferation and 3 BRCAness/PARP inhibitor signatures reduced association strength in AD to 5 significant HR genes, whereas in SQ 10/15 HR genes remained significant. Evaluation of subtypes as potential biomarkers for PARP inhibitor drug response, particularly in SQ is warranted.

REFERENCES

1. Wilkerson M D, et al. PLoS One 2012; 7(5): e36530. PMID 22590557
2. TCGA Lung A D. Nature 2014: 511(7511): 543-550. PMID 25079552
3. Wilkerson M D, et al. Clin Cancer Res 2010; 16(19): 4864-75. PMID 20643781
4. TCGA Lung SQCC. Nature 2012; 489(7417): 519-525. PMID 22960745
5. Neilson T O, et al. Clin Cancer Res 2010; 16(21):5222-5232. PMID 20837693
6. Konstantinopoulos P A, et al. J Clin Oncol 2010; 28:3555-3561. PMID 20547991
7. Daemen A, et al. Breast Cancer Res Treat 2012; 135:505-517. PMID 22875744
8. McGrail D J. et al. npj Systems Biol Applications 2017; 3:8. PMID 28649435

NUMBERED EMBODIMENTS OF THE DISCLOSURE

Other subject matter contemplated by the present disclosure is set out in the following numbered embodiments:

1. A method of determining whether an adenocarcinoma or squamous cell carcinoma patient is likely to respond to PARP inhibitor treatment, the method comprising,
determining the adenocarcinoma subtype or the squamous cell carcinoma subtype of a lung tissue sample from the patient, wherein the adenocarcinoma subtype is selected from the group consisting of squamoid (proximal inflammatory), bronchoid (terminal respiratory unit) and magnoid (proximal proliferative), and the squamous cell carcinoma subtype is selected from the group consisting of primitive, classical, secretory and basal; and
based on the subtype, assessing whether the patient is likely to respond to PARP inhibitor treatment.

2. A method for selecting an adenocarcinoma or squamous cell carcinoma patient for PARP inhibitor treatment, the method comprising, determining an adenocarcinoma subtype or squamous cell carcinoma subtype of a lung tissue sample from the patient, based on the subtype; and selecting the patient for PARP inhibitor treatment.

3. The method of embodiment 1 or 2, wherein the patient is initially determined to have adenocarcinoma or squamous cell carcinoma via a histological analysis of a sample.

4. The method of any one of embodiments 1-3, wherein the patient's adenocarcinoma molecular subtype is selected from squamoid (proximal inflammatory), bronchoid (terminal respiratory unit) or magnoid (proximal proliferative), and is determined via a histological analysis of a sample obtained from the patient.

5. The method of any one of embodiments 1-3, wherein the patient's squamous cell carcinoma subtype is selected from primitive, classical, secretory or basal, and is determined via a histological analysis of a sample obtained from the patient.

6. The method of any one of the above embodiments, wherein the sample is a formalin-fixed, paraffin-embedded (FFPE) lung tissue sample, fresh or a frozen tissue sample, an exosome, or a bodily fluid obtained from the patient.

7. The method of embodiment 6, wherein the bodily fluid is blood or fractions thereof, urine, saliva, or sputum.

8. The method of any one of the above embodiments, wherein the determining the adenocarcinoma subtype or the squamous cell carcinoma subtype comprises determining expression levels of a plurality of classifier biomarkers.

9. The method of embodiment 8, wherein the determining the expression levels of the plurality of classifier biomarkers is at a nucleic acid level by performing RNA sequencing, reverse transcriptase polymerase chain reaction (RT-PCR) or hybridization based analyses.

10. The method of embodiment 8 or 9, wherein the plurality of classifier biomarkers for determining the adenocarcinoma subtype is selected from a publically available lung adenocarcinoma dataset.

11. The method of embodiment 10, wherein the publically available lung adenocarcinoma dataset is TCGA Lung AD RNAseq dataset.

12. The method of embodiment 8 or 9, wherein the plurality of classifier biomarkers for determining the squamous cell carcinoma subtype is selected from a publically available lung squamous cell carcinoma dataset.

13. The method of embodiment 12, wherein the publically available lung squamous cell carcinoma dataset is TCGA Lung SQ RNAseq dataset.

14. The method of embodiment 8 or 9, wherein the plurality of classifier biomarkers for determining the adenocarcinoma subtype is selected from Table 1.

15. The method of embodiment 14, wherein the RT-PCR is quantitative real time reverse transcriptase polymerase chain reaction (qRT-PCR).

16. The method of embodiment 15, wherein the RT-PCR is performed with primers specific to the plurality of classifier biomarkers of Table 1; comparing the detected levels of expression of the plurality of classifier biomarkers of Table 1 to the expression of the plurality of classifier biomarkers of Table 1 in at least one sample training set(s), wherein the at least one sample training set comprises expression data of the plurality of classifier biomarkers of Table 1 from a reference adenocarcinoma TRU sample, expression data of the plurality of classifier biomarkers of Table 1 from a reference adenocarcinoma PP sample, expression data of the plurality of classifier biomarkers of Table 1 from a reference adenocarcinoma PI sample, or a combination thereof; and classifying the first sample as TRU, PP, or PI based on the results of the comparing step.

17. The method of embodiment 16, wherein the comparing step comprises applying a statistical algorithm which comprises determining a correlation between the expression data obtained from the sample and the expression data from the at least one training set(s); and classifying the sample as a TRU, PP, or PI subtype based on the results of the statistical algorithm.

18. The method of any of embodiments 14-17, wherein the plurality of the classifier biomarkers comprise each of the classifier biomarkers set forth in Table 1.

19. The method of embodiment 8 or 9, wherein the plurality of classifier biomarkers for determining the squamous cell carcinoma subtype is selected from Table 3.

20. The method of embodiment 19, wherein the RT-PCR is quantitative real time reverse transcriptase polymerase chain reaction (qRT-PCR).

21. The method of embodiment 20, wherein the RT-PCR is performed with primers specific to the plurality of classifier biomarkers of Table 3; comparing the detected levels of expression of the plurality of classifier biomarkers of Table 3 to the expression of the plurality of classifier biomarkers of Table 3 in at least one sample training set(s), wherein the at least one sample training set comprises expression data of the plurality of classifier biomarkers of Table 3 from a reference squamous cell carcinoma basal sample, expression data of the plurality of classifier biomarkers of Table 3 from a reference squamous cell carcinoma classical sample, expression data of the plurality of classifier biomarkers of Table 3 from a reference squamous cell carcinoma primitive sample, expression data of the plurality of classifier biomarkers of Table 3 from a reference squamous cell carcinoma secretory sample or a combination thereof; and classifying the first sample as basal, classical, primitive or secretory based on the results of the comparing step.

22. The method of embodiment 21, wherein the comparing step comprises applying a statistical algorithm which comprises determining a correlation between the expression data obtained from the sample and the expression data from the at least one training set(s); and classifying the sample as a basal, classical, primitive or secretory subtype based on the results of the statistical algorithm.

23. The method of any of embodiments 19-22, wherein the plurality of the classifier biomarkers comprise each of the classifier biomarkers set forth in Table 3.

24. A method of treating lung cancer in a subject, the method comprising:
measuring the expression level of at least one biomarker nucleic acid in a lung cancer sample obtained from the subject, wherein the at least one biomarker nucleic acid is selected from a set of biomarkers listed in Table 1 or Table 3, wherein the presence, absence and/or level of the at least one biomarker indicates a subtype of the lung cancer; and
administering a PARP inhibitor treatment based on the subtype of the lung cancer.

25. The method of embodiment 24, wherein the lung cancer sample is an adenocarcinoma lung cancer sample, and wherein the set of biomarkers is Table 1.

26. The method of embodiment 25, wherein the at least one biomarker nucleic acid selected from the set of biomarkers comprises, consists essentially of or consists of at least two biomarker nucleic acids, at least 8 biomarker nucleic acids, at least 16 biomarker nucleic acids, at least 32 biomarker nucleic acids, or all 48 biomarker nucleic acids of Table 1.

27. The method of any of embodiments 25-26, wherein the lung tissue sample was previously diagnosed as being adenocarcinoma.

28. The method of embodiment 24, wherein the lung cancer sample is a squamous cell carcinoma sample, and wherein the set of biomarkers is Table 3.

29. The method of embodiment 28, wherein the at least one biomarker nucleic acid selected from the set of biomarkers comprises, consists essentially of or consists of at least two biomarker nucleic acids, at least 10 biomarker nucleic acids, at least 20 biomarker nucleic acids, at least 30 biomarker nucleic acids, at least 40 biomarker nucleic acids, at least 50 biomarker nucleic acids, at least 60 biomarker nucleic acids, at least 70 biomarker nucleic acids or all of the biomarker nucleic acids of Table 3.

30. The method of any of embodiments 28-29, wherein the lung tissue sample was previously diagnosed as being squamous cell carcinoma.

31. The method of embodiment 27 or 30, wherein the previous diagnosis was by histological examination.

32. The method of any one of embodiments 24-31, further comprising measuring the expression of at least one biomarker from an additional set of biomarkers.

33. The method of embodiment 32, wherein the additional set of biomarkers comprise one or more homologous recombination (HR) related genes.

34. The method of embodiment 33, wherein the one or more HR-related genes are selected from ATM, ATR, BRCA1, BRCA2, BRIP1 (FANCJ), CDK12, CHEK1, CHEK2, FANCA, FANCI, FANCD2, MRE11A, RAD51L1 (RAD51B), RAD51C, PTEN or a combination thereof.

35. The method of any of embodiments 24-34, wherein the measuring the expression level is conducted using an amplification, hybridization and/or sequencing assay.

36. The method of embodiment 35, wherein the amplification, hybridization and/or sequencing assay comprises performing quantitative real time reverse transcriptase polymerase chain reaction (qRT-PCR), RNAseq, microarrays, gene chips, nCounter Gene Expression Assay, Serial Analysis of Gene Expression (SAGE), Rapid Analysis of Gene Expression (RAGE), nuclease protection assays, Northern blotting, or any other equivalent gene expression detection techniques.

37. The method of embodiment 36, wherein the expression level is detected by performing qRT-PCR.

38. The method of any of embodiments 24-37, wherein the sample is a formalin-fixed, paraffin-embedded (FFPE) lung tissue sample, fresh or a frozen tissue sample, an exosome, wash fluids, cell pellets, or a bodily fluid obtained from the patient.

39. The method of embodiment 38, wherein the bodily fluid is blood or fractions thereof, urine, saliva, or sputum.

40. The method of any one of embodiments 25-27, wherein the patient's adenocarcinoma subtype is selected from squamoid (proximal inflammatory), bronchoid (terminal respiratory unit) or magnoid (proximal proliferative).

41. The method of any one of embodiments 28-30, wherein the patient's squamous cell carcinoma subtype is selected from primitive, classical, secretory or basal.

42. A method for determining regulation of homologous recombination (HR) in an adenocarcinoma (AD) or squamous cell carcinoma (SQ) lung cancer patient comprising detecting the expression of one or a plurality of homologous recombination (HR) related genes in a sample obtained from the lung AD or SQ lung cancer patient.

43. The method of embodiment 42, wherein the one or more HR-related genes are selected from ATM, ATR, BRCA1, BRCA2, BRIP1 (FANCJ), CDK12, CHEK1, CHEK2, FANCA, FANCI, FANCD2, MRE11A, RAD51L1 (RAD51B), RAD51C, PTEN or a combination thereof.

44. The method of embodiments 42 or 43, further comprising determining the lung AD or SQ subtype of the sample obtained from the patient.

45. The method of embodiment 44, further comprising determining an association between the expression of the one or plurality of HR-related genes to the lung AD or SQ subtype.

The various embodiments described above can be combined to provide further embodiments. All of the U.S. patents, U.S. patent application publications, U.S. patent application, foreign patents, foreign patent application and non-patent publications referred to in this specification and/or listed in the Application Data Sheet are incorporated herein by reference, in their entirety. Aspects of the embodiments can be modified, if necessary to employ concepts of the various patents, application and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A method of treating lung cancer in a human subject, the method comprising:
   (a) measuring a nucleic acid expression level of every biomarker in a plurality of biomarkers in a sample obtained from a lung of a human subject suffering from lung adenocarcinoma, wherein the plurality of biomarkers consists of C-fos-induced growth factor (FIGF), Cathepsin H (CTSH), Secretin receptor (SCTR), Cytochrome P450 family 4 subfamily B member 1 (CYP4B1), G protein-coupled receptor 116 (GPR116), Alcohol dehydrogenase 1B (class I) (ADH1B), Chromobox 7 (CBX7), Hepatic leukemia factor (HLF), Centrosomal protein 55 (CEP55), Tpx2, Microtubule-associated (TPX2), BUB1 mitotic checkpoint serine/threonine kinase B (BUB1B), Kinesin family member 4A (KIF4A), Cyclin B2 (CCNB2), Kinesin family member 14 (KIF14), Maternal embryonic leucine zipper kinase (MELK), and Kinesin family member 11 (KIF11);
   (b) comparing the measured nucleic acid expression level of every biomarker in the plurality of the biomarkers of (a) in at least one sample training set(s), wherein the at least one sample training set is a reference human lung adenocarcinoma bronchioid sample, a reference human lung adenocarcinoma magnoid sample, a reference human lung adenocarcinoma squamoid sample or a combination thereof;
   (c) classifying the subtype of lung adenocarcinoma as bronchioid, magnoid or squamoid based on the results of the comparing step; and
   (d) administering a PARP inhibitor to the human subject when the subtype of the lung adenocarcinoma is determined to be a bronchioid subtype, or one or more chemotherapeutic agents without use of a PARP inhibitor when the subtype of the lung adenocarcinoma is a magnoid subtype or a sqaumoid subtype.

2. The method of claim 1, further comprising measuring the expression of at least one biomarker from an additional set of biomarkers.

3. The method of claim 2, wherein the additional set of biomarkers comprise one or more homologous recombination (HR) related genes.

4. The method of claim 1, wherein the measuring the expression level is conducted using an amplification, hybridization and/or sequencing assay.

5. The method of claim 4, wherein the amplification, hybridization and/or sequencing assay comprises performing quantitative real time reverse transcriptase polymerase chain reaction (qRT-PCR), RNAseq, microarrays, gene chips, nCounter Gene Expression Assay, Serial Analysis of Gene Expression (SAGE), Rapid Analysis of Gene Expression (RAGE), nuclease protection assays, Northern blotting, or any other equivalent gene expression detection techniques.

6. The method of claim 5, wherein the expression level is detected by performing qRT-PCR.

7. The method of claim 1, wherein the sample obtained from the lung is a formalin-fixed, paraffin-embedded (FFPE) lung tissue sample, fresh or a frozen lung tissue sample, an exosome, wash fluids, cell pellets, or a bodily fluid obtained from the subject.

8. The method of claim 7, wherein the bodily fluid is blood or fractions thereof, urine, saliva, or sputum.

9. The method of claim 1, wherein the comparing step comprises applying a statistical algorithm which comprises determining a correlation between the nucleic acid expression data obtained from the sample and the nucleic acid expression data from the at least one training set(s); and classifying the sample as a bronchioid, magnoid or squamoid subtype based on the results of the statistical algorithm.

* * * * *